(12) United States Patent
Huang

(10) Patent No.: US 9,174,212 B2
(45) Date of Patent: Nov. 3, 2015

(54) SYSTEM AND METHOD FOR PARTICLE FILTRATION

(71) Applicant: CYTOVERA INC., Chestnut Hill, MA (US)

(72) Inventor: Lotien R. Huang, Chestnut Hill, MA (US)

(73) Assignee: CYTOVERA INC., Chestnut Hill, MA (US)

( * ) Notice: Subject to any disclaimer, the term of this patent is extended or adjusted under 35 U.S.C. 154(b) by 0 days.

(21) Appl. No.: 14/209,046

(22) Filed: Mar. 13, 2014

(65) Prior Publication Data

US 2014/0190903 A1 Jul. 10, 2014

Related U.S. Application Data

(63) Continuation of application No. 13/518,514, filed as application No. PCT/US2010/061866 on Dec. 22, 2010, now Pat. No. 8,679,751.

(60) Provisional application No. 61/294,611, filed on Jan. 13, 2010, provisional application No. 61/289,730, filed on Dec. 23, 2009.

(51) Int. Cl.
*C12M 1/00* (2006.01)
*C12Q 1/00* (2006.01)
*C12Q 1/68* (2006.01)
(Continued)

(52) U.S. Cl.
CPC ......... *B01L 3/502753* (2013.01); *B01L 3/5021* (2013.01); *B01L 3/50255* (2013.01); *C12M 47/04* (2013.01); *B01L 2300/042* (2013.01); *B01L 2300/0681* (2013.01); *B01L 2300/0829* (2013.01); *B01L 2400/0409* (2013.01); *B01L 2400/049* (2013.01); *G01N 2015/1006* (2013.01); *G01N 2015/1081* (2013.01); *G01N 2015/1087* (2013.01)

(58) Field of Classification Search
USPC ........ 435/4, 6.1, 7.24, 34, 40.5, 283.1, 288.5; 422/68.1, 82.05, 82.08; 210/323.1, 210/435, 467
See application file for complete search history.

(56) References Cited

U.S. PATENT DOCUMENTS 4,422,939 A 12/1983 Sharp et al.
4,797,211 A 1/1989 Ehrfeld et al.
(Continued)

FOREIGN PATENT DOCUMENTS

CN 2411833 Y 12/2000
JP 2004-354364 A 12/2004
(Continued)

OTHER PUBLICATIONS

Chinese Search Report from corresponding Chinese Patent Application No. 201080064293.X dated Aug. 5, 2014.
(Continued)

*Primary Examiner* — Narayan Bhat
(74) *Attorney, Agent, or Firm* — Lando & Anastasi, LLP

(57) ABSTRACT

Embodiments of the present disclosure feature a filtration system comprising a filtration module for particle filtration and methods of using the device for the isolation of particles (e.g., viable cells). Advantageously, embodiments of the device provide for the high throughput filtration of large volumes of sample while preserving cell viability and providing high yields.

44 Claims, 47 Drawing Sheets

(51) Int. Cl.
*G01N 33/00* (2006.01)
*C12Q 1/04* (2006.01)
*G01N 1/30* (2006.01)
*G01N 33/48* (2006.01)
*C12M 1/34* (2006.01)
*G01N 15/06* (2006.01)
*G01N 21/00* (2006.01)
*B01D 24/00* (2006.01)
*B01L 3/00* (2006.01)
*G01N 15/10* (2006.01)

(56) References Cited

U.S. PATENT DOCUMENTS

| | | | |
|---|---|---|---|
| 5,427,663 | A | 6/1995 | Austin et al. |
| 5,601,711 | A | 2/1997 | Sklar et al. |
| 5,715,946 | A | 2/1998 | Reichenbach |
| 5,837,115 | A | 11/1998 | Austin et al. |
| 6,881,317 | B2 | 4/2005 | Huang et al. |
| 7,150,812 | B2 | 12/2006 | Huang et al. |
| 7,276,170 | B2 | 10/2007 | Oakey et al. |
| 7,318,902 | B2 | 1/2008 | Oakey et al. |
| 7,472,794 | B2 | 1/2009 | Oakey et al. |
| 7,597,791 | B2 | 10/2009 | Huang et al. |
| 7,735,652 | B2 | 6/2010 | Inglis et al. |
| 8,679,751 | B2 | 3/2014 | Huang |
| 2003/0124715 | A1 | 7/2003 | Tortorella |
| 2005/0092662 | A1 | 5/2005 | Gilbert et al. |
| 2005/0161331 | A1 | 7/2005 | Huang et al. |
| 2005/0189297 | A1 | 9/2005 | Bosch et al. |
| 2006/0046305 | A1 | 3/2006 | Liu et al. |
| 2006/0204400 | A1 | 9/2006 | Blattert et al. |
| 2007/0026381 | A1 | 2/2007 | Huang et al. |
| 2007/0059774 | A1 | 3/2007 | Grisham et al. |
| 2007/0160503 | A1 | 7/2007 | Sethu et al. |
| 2007/0172903 | A1 | 7/2007 | Toner et al. |
| 2008/0071033 | A1 | 3/2008 | Sugiyama |
| 2008/0081033 | A1 | 4/2008 | Sowemimo-Coker et al. |
| 2008/0085551 | A1 | 4/2008 | Kim et al. |
| 2008/0135502 | A1 | 6/2008 | Pyo et al. |
| 2008/0290037 | A1 | 11/2008 | Liu |
| 2009/0183871 | A1 | 7/2009 | Salamitou et al. |
| 2010/0120077 | A1 | 5/2010 | Daridon |

FOREIGN PATENT DOCUMENTS

| | | |
|---|---|---|
| JP | 2005-205387 A | 8/2005 |
| JP | 2006-263693 A | 10/2006 |
| JP | 2007-021465 A | 2/2007 |
| JP | 2007-175684 A | 7/2007 |
| JP | 2009-291783 A | 12/2009 |
| RU | 87084 U1 | 9/2009 |
| WO | 2008024070 A1 | 2/2008 |

OTHER PUBLICATIONS

Examiner's Report from corresponding Canadian Patent Application No. 2,785,390 dated Dec. 30, 2014.

Huang et al., "A DNA prism for high-speed continuous fractionation of large DNA molecules", Nature Biotechnology, vol. 20, No. 10, Oct. 1, 2002, pp. 1048-1051.

Huang et al., "Continuous Particle Separation Through Deterministic Lateral Displacement", Sicence, American Association for bthe Advancement of Science, US, vol. 304, May 14, 2004, pp. 987-990.

J.A. Davis et al.: "Deterministic hydrodynamics: Taking blood apart", Proceedings of the National Academy of Sciences, vol. 103, No. 40, Sep. 25, 2006, pp. 14779-14784, XP055103226, ISSN: 0027-8424, DOI: 10.1073/pnas.0605967103, p. 14780, col. 2, paragraph 3-p. 14782, col. 2, paragraph 3; figure 2A.

Supplementary European Search Report from corresponding European Patent Office Application No. 10840134.0 dated Feb. 2, 2015.

International Search Report and Written Opinion from PCT/US2010/61866 dated May 19, 2011.

Lu et al., "Enrichment, Characterization, and a Responsiveness of Single Primitive CD34 +++ Human Umbilical Cord Blood Hematopoietic Progenitors With High Proliferative and Replating Potential," 1993, Blood, 81, 41-48.

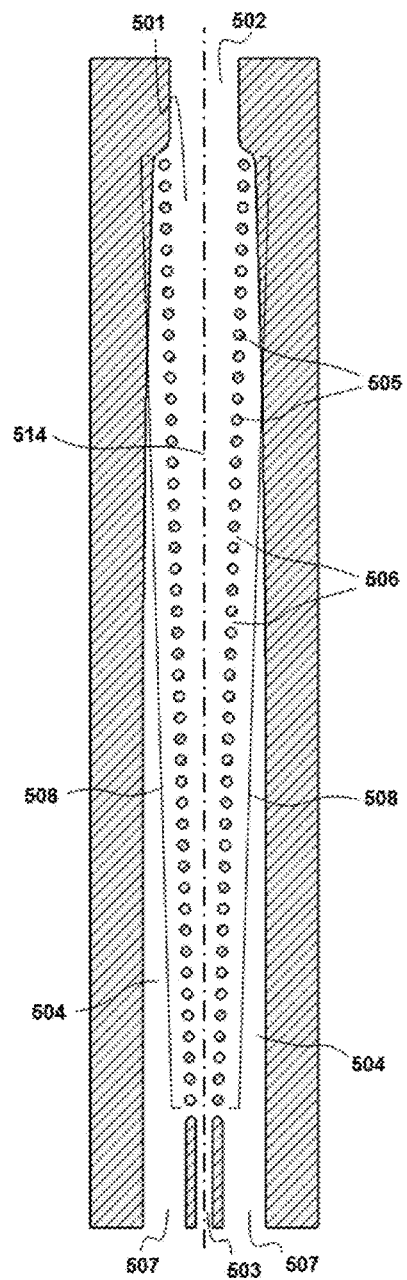
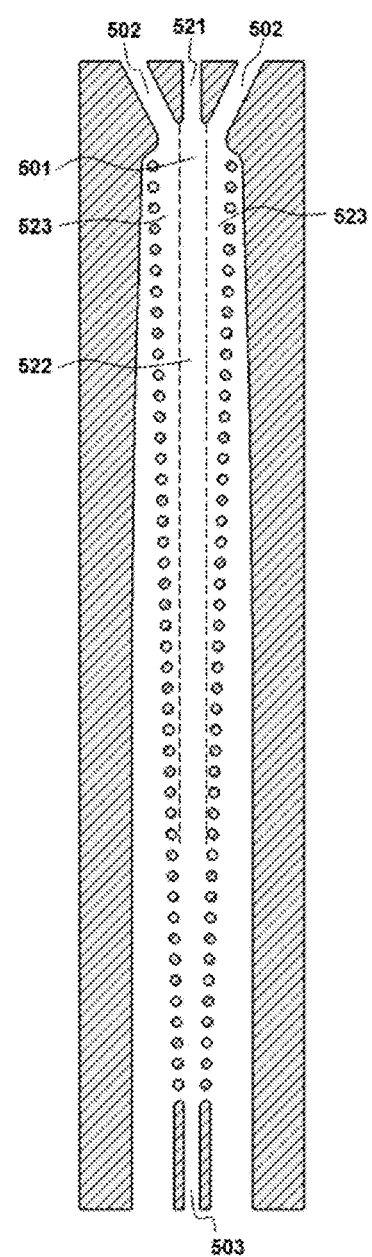
Fig. 14A
Fig. 14B

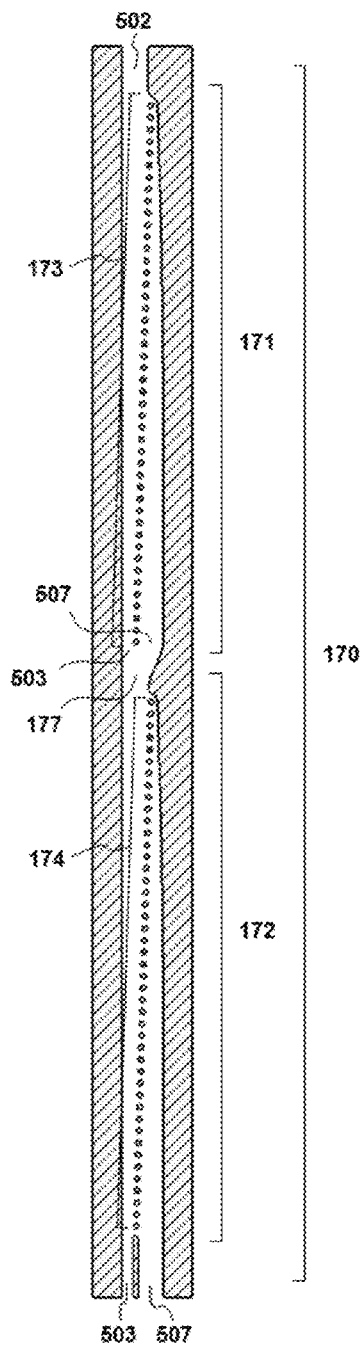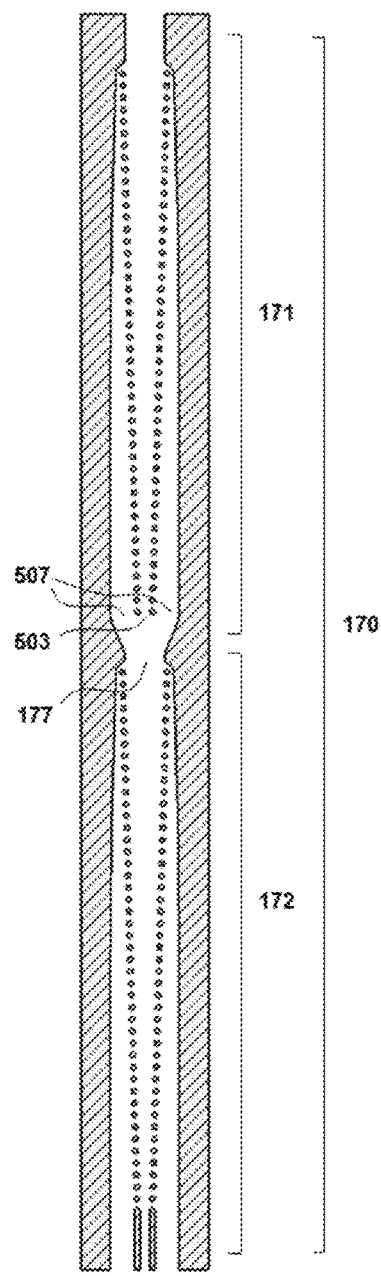

Fig. 21A
Fig. 21B
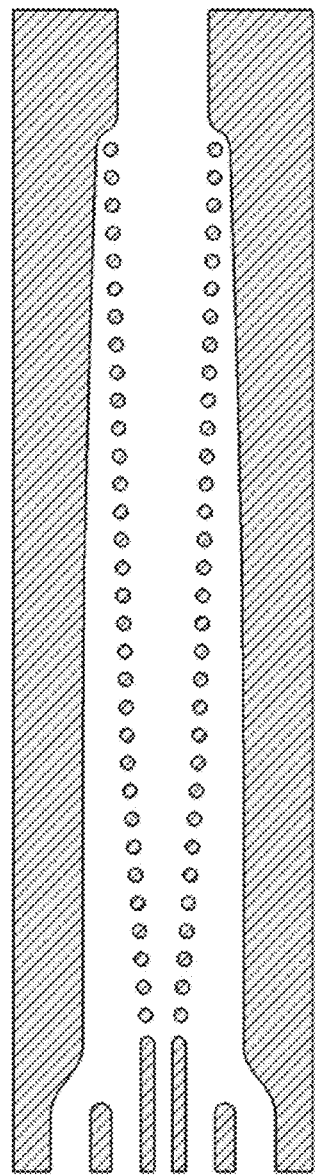
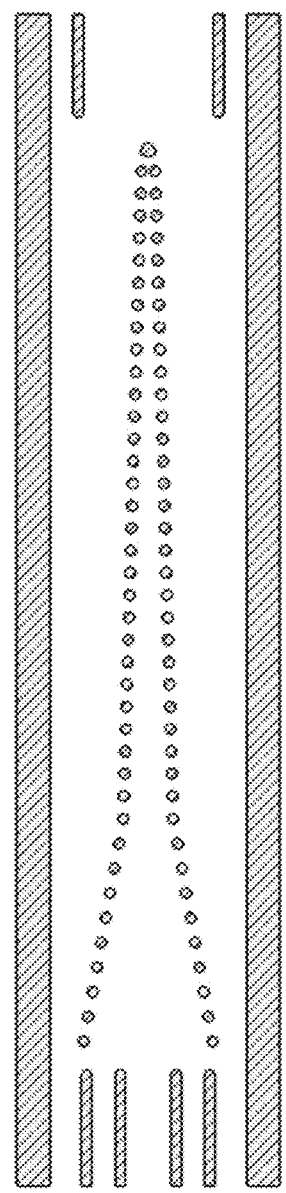

Fig. 23A
Fig. 23B
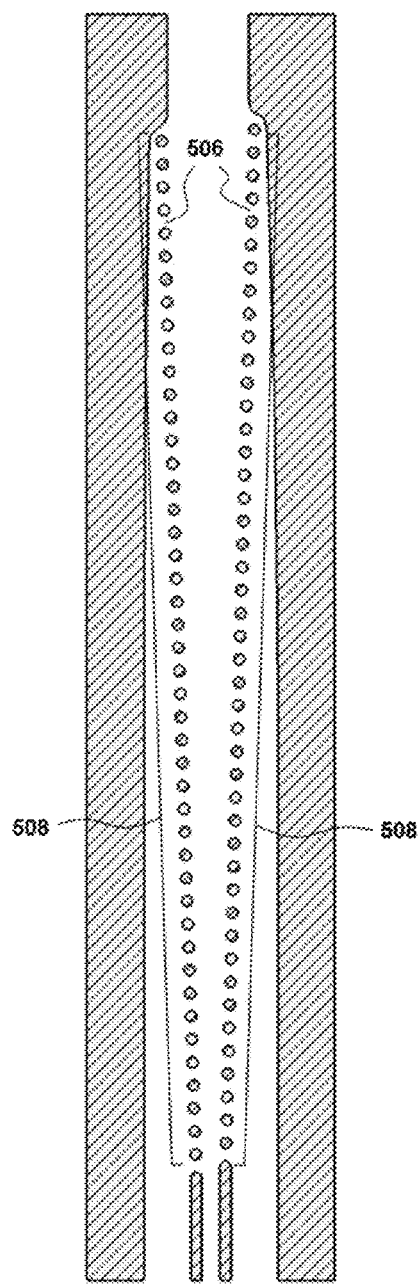
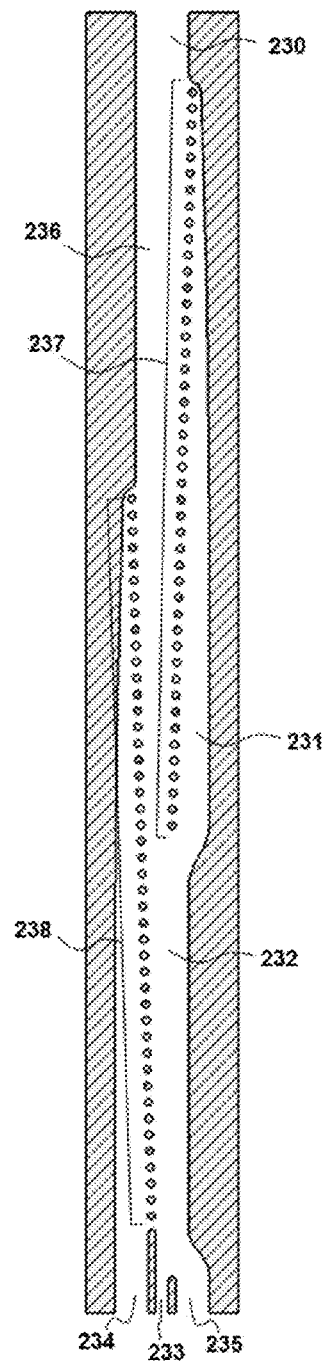

Fig. 29A
Fig. 29B
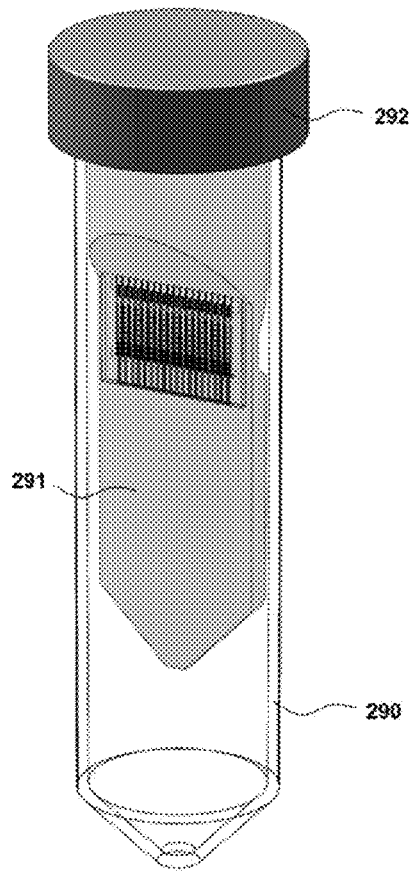
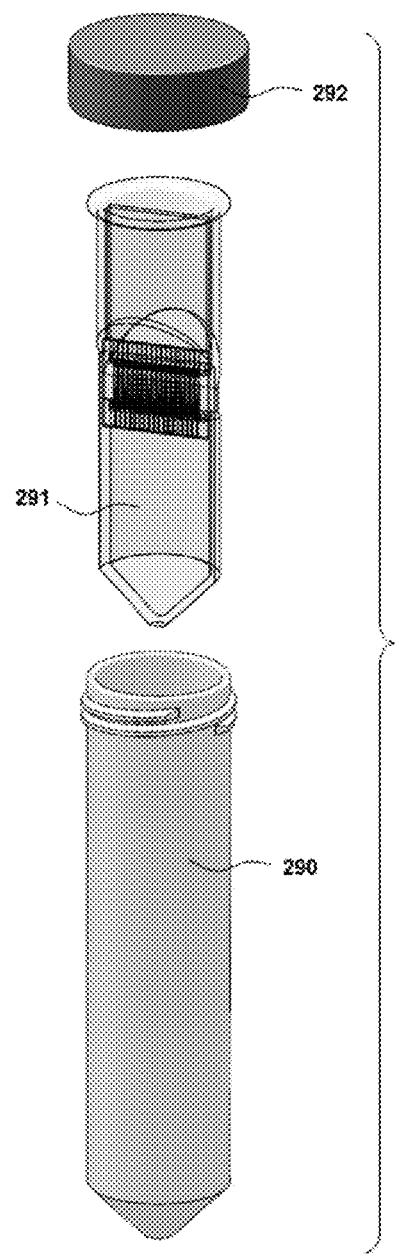

Fig. 30C
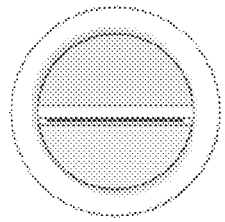
Fig. 30D    Fig. 30E    Fig. 30F
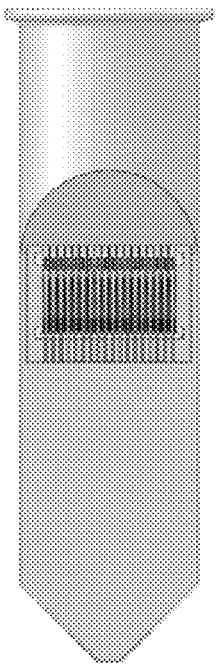 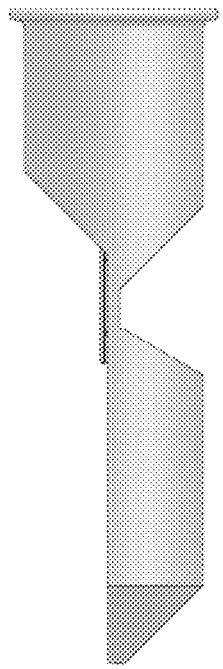 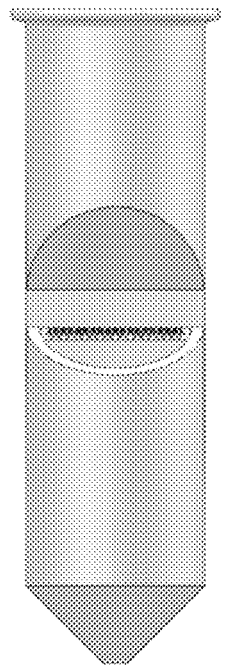
Fig. 30G
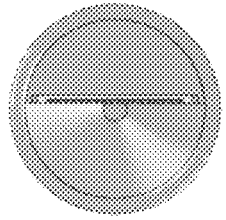

Fig. 33
| Sample | Processing Throughput | Leukocyte Retention | Erythrocyte Carryover | Platelet Carryover | Leukocyte Viability Before Isolation | Leukocyte Viability After Isolation |
|---|---|---|---|---|---|---|
| 1 | 5.5 ml/hr | 96% | 2.1% | <1% | 99.6% | 99.7% |
| 2 | 5.3 ml/hr | 93% | 1.8% | <1% | 99.5% | 99.3% |
| Average | 5.4 ml/hr | 94% | 2.0% | <1% | 99.6% | 99.5% |
Fig. 34A
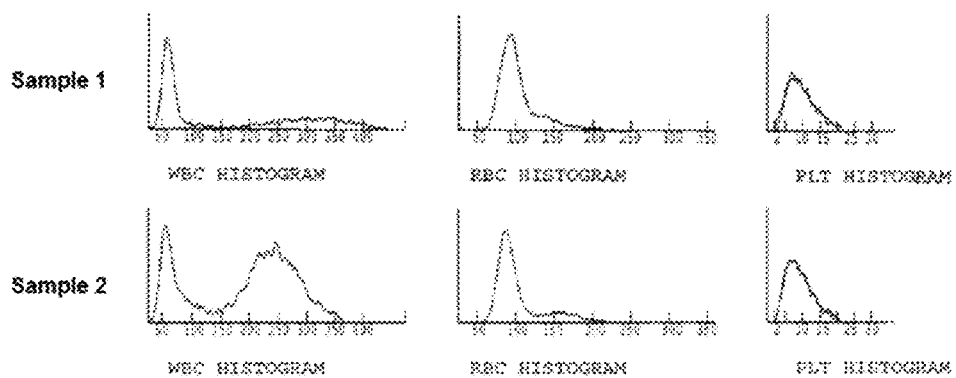
Fig. 34B
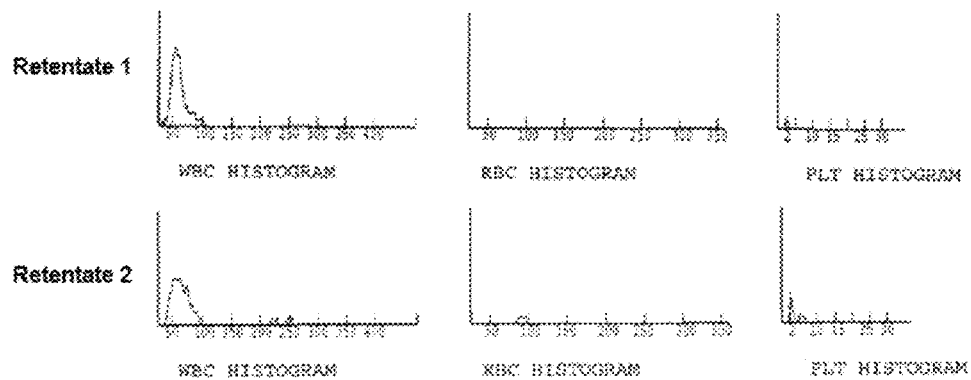

Fig. 34C

| | Lymphocyte (10³/µl) | Monocyte (10³/µl) | Granulocyte (10³/µl) | Erythrocyte (10⁶/µl) | Platelet (10³/µl) |
|---|---|---|---|---|---|
| Blood Sample 1 | 1.2 | 0.1 | 1.1 | 2.08 | 81 |
| Blood Sample 2 | 0.9 | 0.1 | 2.2 | 2.45 | 93 |
| Retentate 1 | 0.6 | 0.0 | 0.0 | 0.00 | 0 |
| Retentate 2 | 0.7 | 0.0 | 0.0 | 0.00 | 0 |

Fig. 34D

| Sample | Processing Throughput | Lymphocyte Purity | Erythrocyte Carryover | Platelet Carryover |
|---|---|---|---|---|
| 1 | 8.7 ml/hr | >90% | <0.5% | <1% |
| 2 | 9.6 ml/hr | >90% | <0.5% | <1% |
| Average | 9.2 ml/hr | >90% | <0.5% | <1% |

Fig. 35A

| Sample | Throughput (ml/hr) | Volume Reduction Factor | Leukocyte Recovery Yield | Viability Before Processing | Viability After Processing |
|---|---|---|---|---|---|
| 1 | 12.0 | 5.7 | 86% | 99.5% | 99.4% |
| 2 | 10.2 | 5.6 | 91% | 99.8% | 99.6% |
| 3 | 12.8 | 5.3 | 87% | 99.1% | 99.2% |
| 4 | 11.4 | 5.3 | 87% | 98.7% | 99.6% |
| 5 | 11.6 | 5.1 | 84% | 99.5% | 99.7% |
| 6 | 9.8 | 5.6 | 89% | 99.4% | 99.3% |
| 7 | 12.0 | 5.2 | 89% | 99.4% | 99.3% |
| 8 | 11.2 | 5.5 | 83% | 99.8% | 99.9% |
| 9 | 12.0 | 4.8 | 93% | 99.6% | 99.7% |
| Average | 11.4 | 5.3 | 88% | 99.4% | 99.6% |

Fig. 35B

| Sample | Cord Blood CD34+ Cell Frequency | Retentate CD34+ Cell Frequency | CD34+ Cell Recovery Yield |
|---|---|---|---|
| 10 | 0.22% | 0.22% | 87% |
| 11 | 0.38% | 0.38% | 89% |
| 12 | 0.68% | 0.74% | 85% |
| Average | | | 87% |

Fig. 35C

| Sample | Cord Blood CFC-GM Frequency | Retentate CFC-GM Frequency | CFC-GM Recovery Yield |
|---|---|---|---|
| 13 | 0.06% | 0.06% | 92% |
| 14 | 0.17% | 0.21% | 87% |
| 15 | 0.17% | 0.20% | 98% |
| Average | | | 92% |

SYSTEM AND METHOD FOR PARTICLE FILTRATION

RELATED APPLICATIONS

This application claims the benefit under 35 U.S.C. §120 as a continuation of U.S. application Ser. No. 13/518,514, titled "SYSTEM AND METHOD FOR PARTICLE FILTRATION," filed on Jun. 22, 2012, which is a national stage application under 35 U.S.C. §371 of PCT Application No. PCT/US10/61866, titled "A SYSTEM AND METHOD FOR PARTICLE FILTRATION," filed on Dec. 22, 2010, which claims priority to U.S. Provisional Application Ser. No. 61/294,611, titled "SYSTEM FOR PARTICLE FILTRATION," filed on Jan. 13, 2010 and to U.S. Provisional Application Ser. No. 61/289,730, titled "DEVICE FOR PARTICLE FILTRATION AND METHODS OF USE THEREFOR," filed on Dec. 23, 2009, each of which is herein incorporated by reference in its entirety.

BACKGROUND

Methods for separating cells from biological samples are important to many clinical procedures and to scientific research methods. In cord blood banking, umbilical cord blood may be volume reduced using a cell separation process before entering cryopreservation to reduce the long term storage cost. In cellular therapy, certain cell types may be enriched before transfusing into a patient to increase engraftment. Current filtration technologies for cell separation often fail to preserve cell viability and typically have low yields. For example, cell separation techniques that rely on size exclusion subject fragile cells to shear stress causing cell damage or lysis. The accumulation of cellular debris accelerates device fouling and clogging. Often cells isolated using such methods are activated, altered, damaged, or killed. Microfluidic devices are limited by the volume of sample that they can process. Simply increasing flow rate through such devices is unsuccessful because as flow rate increases, the shear stress of cell moving through the device also increases. Thus, shear stress limits the volumetric throughput. It is thus desirable to provide a method and device for particle filtration that does not use size exclusion as the filtration mechanism. In particular, it is desirable to provide a method and device for cell filtration that does not easily clog, that has high volumetric throughput, that is physically compact, and that does not damage or activate the cells.

SUMMARY

As described below, the present disclosure features a device for particle filtration and methods of using the device for the enrichment of viable cells. In particular, the present disclosure features the use of such devices for isolation of blood cell types, volume reduction of umbilical cord bloods, and preparation of stromal vascular fractions.

Advantageously, the device may provide for the high throughput filtration of large volumes of sample while preserving cell viability and providing high yields. Some embodiments of the present disclosure may comprise devices suitable for automation and high throughput processing, and some embodiments of the present disclosure may comprise systems that enable processing clinical samples in closed systems. Further, the method for using the device may provide for high performance, high recovery, and in some cases high purity. In addition, the method for using the device as applied to clinical sample processing, e.g. cord blood volume reduction, bone marrow stem cell enrichment, peripheral blood stem cell processing, and stromal vascular fraction preparation, may provide for maintaining a high degree of post-separation cell viability, ease of use, safety, and cost efficiency.

In one embodiment, the disclosure provides a particle filtration device that provides for the high-throughput separation of viable cells. Because the particle filtration device provides for particle separation with minimal shear force at least about 50%, 75%, 85%, 95%, 98%, 99%, 99.5% or more of the separated cells are viable and suitable for research and medical use. In various embodiments, the filtration system features one or more containers suitable for holding a sample and/or carrier fluid for delivery to one or more filter unit devices, and one or more additional containers suitable for holding retentate or filtrate flowing out of the device. In one embodiment, the containers are flexible bags suitable for holding liquids. In another embodiment, the containers are connected to the filter unit by flexible tubing suitable for carrying fluids. If desired, the tubing is connected to the container and/or filter unit housing by an adapter.

Aspects and embodiments of the disclosure are directed to a system for particle filtration containing a cartridge containing a housing and a plurality (for example, about 5, 10, 15, 20, 25, 30, 35, 40, 50, 75, 100, 200, 250, 500, 750, 1,000, 2,000, or 5,000) of filtration units, where the housing contains a feed sample inlet, a retentate outlet, and a filtrate outlet; and each filtration unit contains a retentate chamber having proximal and distal ends, a filtrate chamber, and a row of pillars positioned between the retentate chamber and the filtrate chamber, the pillars defining a plurality of pores permitting fluid communication between the retentate chamber and the filtrate chamber, where the width of the retentate chamber decreases from the proximal end to the distal end, the width of the filtrate chamber increases from the proximal end to the distal end, and the filtration unit is configured such that the effective pore size of the pores is smaller than, for example, about 30%, 50%, 60%, 70%, 80%, 90%, 95%, or 98% of the physical pore size of the pores; the feed sample inlet is in fluid connection with the proximal end of the retentate chamber present in each filtration unit; the filtrate outlet is in fluid connection with the filtrate chamber present in each filtration unit; and the retentate outlet is in fluid connection with the distal end of the retentate chamber present in each of the plurality of filtration units.

In another aspect, the disclosure provides a system for particle filtration containing a cartridge comprising a housing and a plurality of filtration units, where the housing contains a feed sample inlet, a retentate outlet, and a filtrate outlet; and each filtration unit contains a retentate chamber having proximal and distal ends, a filtrate chamber containing at least one distal end, and a filter containing a plurality of pores positioned between the retentate chamber and the filtrate chamber, the pores permitting fluid communication between the retentate chamber and the filtrate chamber, where the filtrate chamber, the filter and the retentate chamber are configured such that the effective pore size of the pores is smaller than the physical pore size of the pores; the feed sample inlet is in fluid connection with the proximal end of the retentate chamber present in each filtration unit; the filtrate outlet is in fluid connection with the filtrate chamber present in each filtration unit; and the retentate outlet is in fluid connection with the distal end of the retentate chamber present in each of the plurality of filtration units.

In another aspect, the disclosure provides a system for particle filtration containing a cartridge containing a housing and a plurality of filtration units, where the housing contains a feed sample inlet, a retentate outlet, and a filtrate outlet; and each filtration unit contains a first flow chamber, a second flow chamber, and a filter containing about 3, 5, 6, 7, 8, 9, 10, 15, 20, 25, 30, 40, 50, 100, 200, 250, 300, 500, 1,000, 2,000, 5,000 or more pores having a physical pore size between about 100 nm and about 3 mm (for example, about 100 nm, 200 nm, 300 nm, 400 nm, 500 nm, 750 nm, 1 µm, 2 µm, 3 µm, 5 µm, 7.5 µm, 10 µm, 20 µm, 30 µm, 50 µm, 75 µm, 100 µm, 200 µm, 300 µm, 500 µm, 1 mm, 2 mm, or 3 mm) where the filter is disposed between the first flow chamber and the second flow chamber; and the first flow chamber and second flow chamber are configured such that the retentate particles are retained by the filter without physical restriction; the feed sample inlet is in fluid connection with the proximal end of the first flow chamber present in each filtration unit; the filtrate outlet is in fluid connection with the distal end of the second chamber present in each filtration unit; and the retentate outlet is in fluid connection with the distal end of the first flow chamber present in each of the plurality of filtration units.

In another aspect, the disclosure provides a system for particle filtration containing a cartridge containing a housing and a plurality of filtration units, where the housing contains a feed sample inlet, a retentate outlet, and a filtrate outlet; and each filtration unit contains a first flow chamber having proximal and distal ends, a second flow chamber, and a filter disposed between the first flow chamber and the second flow chamber containing pores having a physical pore size between about 10 nm and 10 mm, where the first flow chamber and second flow chamber are configured such that the retention size of the filter is smaller than the physical pore size; the feed sample inlet is in fluid connection with the proximal end of the first flow chamber present in each filtration unit; the filtrate outlet is in fluid connection with the distal end of the second flow chamber present in each filtration unit; and the retentate outlet is in fluid connection with the distal end of the first flow chamber present in each of the plurality of filtration units.

In another aspect, the disclosure provides a system for particle filtration containing a cartridge containing a housing and a plurality of filtration units, where the housing contains a feed sample inlet, a retentate outlet, a filtrate outlet, and optionally a carrier fluid inlet. Each filtration unit may include a first input port, a first output port, a second output port, and optionally a second input port in fluid connection with the carrier fluid inlet. Each filtration unit may have a design efficiency index of greater than about 0.3 $mm^{-2}$. The feed sample inlet may be in fluid connection with the first input port present in each filtration unit. The filtrate outlet may be in fluid communication with the first output port present in each filtration unit. The retentate outlet may be in fluid connection with the second output port present in each of the plurality of filtration units.

In another aspect, the disclosure provides a tube filter system containing a centrifuge tube, a tube insert, and a cap, where the tube insert contains at least one filtration unit according to any of the previous aspects, a feed sample reservoir and optionally a carrier fluid reservoir, each of which is in fluid connection with the first flow chamber or the proximal end of the retentate chamber, and an output reservoir in fluid communication with the distal end of the retentate chamber or the second flow chamber, where the output reservoir is adapted to receive the retentate or filtrate from the filtration unit.

In another aspect, the disclosure provides a plate filter system containing one or more of a sample well and optionally a carrier fluid well in fluid connection with a filtration unit according to any previous aspect or any other aspect of the disclosure delineated herein; and a filtrate well and a retentate well in fluid connection with the filtration unit, where the filtrate well and a retentate well are configured to receive filtrate and retentate from the filtration unit.

In another aspect, the disclosure provides a plate filter system containing one or more of a sample well and optionally a carrier fluid well in fluid connection with a filtration unit according to any previous aspect or any other aspect of the disclosure delineated herein; and a filtrate well and a retentate well, where the filtrate well and a retentate well are configured to receive filtrate and retentate from the filtration unit. In one embodiment, the filtrate well or the retentate well is not on the same plate as the sample well.

In various embodiments of any of the above aspects or any other aspect of the disclosure delineated herein the feed sample inlet has a proximal end connected to an adaptor via a tubing line, the retentate outlet is connected to a retentate collection bag via a tubing line, and the filtrate outlet is connected to a filtrate collection bag via a tubing line. In other embodiments of the above aspects, the feed sample inlet is connected to a sample collection bag having proximal and distal ends, where the proximal end contains a membrane adapted to receive a needle and the distal end contains a port where an adaptor can be attached. In other embodiments of the above aspects, the feed sample inlet has a proximal end connected to a sample collection bag via a tubing line, the retentate outlet is connected to a retentate collection bag via a tubing line, and the filtrate outlet is connected to a filtrate collection bag via a tubing line. In still other embodiments of the above aspects, the sample collection bag contains a needle for drawing sample into the sample collection bag.

Compositions and articles defined by the disclosure were isolated or otherwise manufactured in connection with the examples provided below. Other features and advantages of the disclosure will be apparent from the detailed description, and from the claims.

In accordance with an aspect of the present disclosure, there is provided a filtration device. The filtration device comprises a first flow chamber. The first flow chamber includes at least one inlet configured to receive a feed comprising particles and a fluid, and at least one retentate outlet. The filtration device comprises a second flow chamber including a distal end having at least one filtrate outlet, and a filter positioned between the first flow chamber and the second flow chamber. The filter includes a first row of pillars and a plurality of pores defined by spacings between adjacent pillars. Each pore of the plurality of pores includes a physical pore size defined by a distance between the adjacent pillars which define the pore and an effective pore size smaller than the physical pore size. The filtration device further comprises means for moving the feed through the filtration device. The first flow chamber, the second flow chamber, the filter, and the means for moving the feed through the filtration device are configured to retain a substantial fraction of particles having a size greater than the effective pore sizes of the pores and smaller than the physical pore sizes of the pores as retentate in the first flow chamber, and pass a substantial fraction of the fluid as filtrate into the second flow chamber.

In accordance with some embodiments, the first flow chamber comprises a first substantially constant depth. In accordance with some embodiments, the second flow chamber comprises a second substantially constant depth. In accordance with some embodiments, a distance between the filter and a sidewall of the first flow chamber decreases along a length from the at least one inlet to the at least one retentate outlet. In accordance with some embodiments, a distance between the filter and a sidewall of the second flow chamber increases along a length from a proximal end of the second flow chamber to the distal end.

In accordance with some embodiments, an angle between a line tangent to a sidewall of the second flow chamber and a line tangent to the row of pillars is less than about 5 degrees.

In accordance with some embodiments, a subset of the pores has substantially identical physical pore sizes.

In accordance with some embodiments, a subset of the pores has substantially identical effective pore sizes.

In accordance with some embodiments, the first row of pillars comprises more than about 10 percent of all the pillars present in the filtration device.

In accordance with some embodiments, the filtration device of claim has a device length defined by the greater of a length of the first flow chamber and a length of the second flow chamber and a device width defined by a sum of a width of the first flow chamber and a width of the second flow chamber at a point of the greatest sum of a width of the first flow chamber and a width of the second flow chamber, the device length to the device width having a ratio of more than about 6.

In accordance with some embodiments, each pore has an effective pore size that is less than about 80 percent of the physical pore size of the pore.

In accordance with some embodiments, the first chamber comprises at least one carrier fluid inlet distinct from the at least one inlet.

In accordance with some embodiments, the at least one carrier fluid comprises at least one of nucleic acid stains, fixatives, freezing solutions, alkylating agents, antibodies, magnetic beads, enzymes, collagenase, lipase, DNase, substrates of certain enzymes, active derivatives of cyclophosphamide, growth factors, detergents, and lysis solutions.

In accordance with some embodiments, each of the first flow chamber and the filter are free of any leading edge having a radius of curvature smaller than about 1 µm, in a flow path through the device.

In accordance with some embodiments, a first subset of the pores has a different effective pore size than a second subset of the pores. In some embodiments, the at least one filtrate outlet of the second flow chamber is configured to collect the filtrate passed through the first subset of pores and wherein the second flow chamber comprises a second filtrate outlet configured to collect filtrate passed through the second subset of pores.

In accordance with some embodiments, the filtration device further comprises a second filter and a third flow chamber. The second filter may be disposed between the first flow chamber and the third flow chamber. The third flow chamber may include a proximal end and a distal end, the distal end having at least one outlet. The third chamber may widens along a length from the proximal end to distal end.

In accordance with some embodiments, the filtration device has a device length defined by a length of the first flow chamber and a device width defined by a sum of a width of the first flow chamber, a width of the second flow chamber and a width of the third flow chamber at a point of the greatest sum of a width of the first flow chamber, a width of the second flow chamber and a width of the third flow chamber, the device length to the device width having a ratio of more than about 5.

In accordance with some embodiments, the filtration device has fewer than about 5,000 pillars.

In accordance with some embodiments, the first filter and the second filter comprise more than about 15 percent of all pillars included in the filtration device.

In accordance with some embodiments, the filtration device is substantially symmetric about a mirror plane through a center line of the first flow chamber.

In accordance with some embodiments, a tangent line defined by the first row of pillars and a tangent line defined by the second row of pillars are non-parallel.

In accordance with some embodiments, the filtration device further comprises a second filter, a third flow chamber, and a fourth flow chamber. The second filter may be disposed between the third flow chamber and the fourth flow chamber. The third flow chamber may comprise at least one inlet and at least one outlet. The fourth flow chamber may comprise at least one outlet.

In accordance with some embodiments, the at least one outlet of the third flow chamber is configured to collect a retentate from the first filter. The third flow chamber may further comprise a second outlet distinct from the at least one outlet, wherein the second outlet of the third flow chamber is configured to collect a retentate from the second filter.

In accordance with some embodiments, the at least one outlet of the third flow chamber is configured to collect a retentate from the first filter and a retentate from the second filter.

In accordance with some embodiments, the at least one outlet of the third flow chamber is configured to collect a retentate from the first filter and a retentate from the second filter. The third flow chamber may further comprises a second outlet distinct from the at least one outlet, wherein the second outlet of the third flow chamber is configured to collect a filtrate from the first filter.

In accordance with some embodiments, the filtration device of claim has a device length defined by a sum of a length of the first flow chamber and a length of the third flow chamber and a device width defined by the greater of a sum of a width of the first flow chamber and a width of the second flow chamber at a point of the greatest sum of a width of the first flow chamber and a width of the second flow chamber and a sum of a width of the third flow chamber and a width of the fourth flow chamber at a point of the greatest sum of a width of the third flow chamber and a width of the fourth flow chamber, the device length to the device width having a ratio of more than about 10.

In accordance with some embodiments, the first filter and the second filter comprise no fewer than 10 percent of all pillars included in the filter device.

In accordance with some embodiments, the at least one inlet of the third flow chamber is in fluid connection with the at least one filtrate outlet of the second flow chamber.

In accordance with some embodiments, the at least one inlet of the third flow chamber is in fluid connection with the at least one retentate outlet of the first flow chamber.

In accordance with some embodiments, the at least one inlet of the third flow chamber is in fluid connection with the at least one outlet of the first flow chamber and with the at least one outlet of the second flow chamber.

In accordance with some embodiments, the third flow chamber further comprises at least one carrier fluid inlet distinct from the at least one inlet.

In accordance with some embodiments, the filtration device is configured to satisfy the "filtrate chamber expansion criterion."

In accordance with some embodiments, the filtration device is configured to satisfy the "minimum pore number criterion."

In accordance with some embodiments, the filtration device is configured to flow a fluid through each pore at a volumetric flow rate of less than about 3 percent of a volumetric flow rate at the proximal end of the first flow chamber.

In accordance with some embodiments, the filtration device is configured to flow a fluid through the first chamber at a substantially constant flow speed.

In accordance with some embodiments, the filtration device is configured to flow a fluid through the second chamber at a substantially constant flow speed.

In accordance with some embodiments, the filtration device is configured to flow a fluid through essentially all of the pores at a substantially identical flow rate.

In accordance with some embodiments, the pillars have egg-shaped cross sections.

In accordance with some embodiments, the filtration device further comprises a second filter, a third filter, a fourth filter, a third flow chamber, a fourth flow chamber, a fifth flow chamber, and a sixth flow chamber. The second filter may be disposed between the first flow chamber and the third flow chamber. The third filter may be disposed between the fourth flow chamber and the fifth flow chamber. The fourth filter may be disposed between the fourth flow chamber and the sixth flow chamber. The third flow chamber may comprise a first end and at least one outlet. The third flow chamber may widen along a length from the first end of the third flow chamber towards the at least one outlet of the third flow chamber. The fifth flow chamber may comprise a first end and at least one outlet. The fifth flow chamber may widen along a length from the first end of the fifth flow chamber towards the at least one outlet of the fifth flow chamber. The sixth flow chamber may comprise a first end and at least one outlet. The sixth flow chamber may widen along a length from the first end of the sixth flow chamber towards the at least one outlet of the sixth flow chamber. The fourth flow chamber may comprise at least one inlet and at least one outlet. The at least one inlet of the fourth flow chamber may be in fluid connection with the at least one retentate outlet of the first flow chamber, the at least one filtrate outlet of the second flow chamber, and the at least one outlet of the third flow chamber.

In accordance with some embodiments, the filtration device further comprises a second filter and a third flow chamber. The second filter may be disposed between the second flow chamber and the third flow chamber. The third flow chamber may comprise at least one inlet and at least one outlet.

In accordance with some embodiments, the device is substantially symmetric about a minor plane through the first flow chamber and the fourth flow chamber.

In accordance with some embodiments, the fourth chamber further comprises a carrier fluid inlet distinct from the at least one inlet of the fourth flow chamber.

In accordance with another aspect of the present disclosure, there is provided a method for particle filtration. The method comprises providing a filtration device. The filtration device includes at least one filtration unit. Each filtration unit includes a first flow chamber including a feed inlet and a retentate outlet, a second flow chamber including a filtrate outlet, and a filter including a plurality of pores having physical pore sizes, the filter being disposed between the first flow chamber and the second flow chamber. The method further comprises introducing a feed including a feed fluid and at least one population of particles having sizes smaller than the physical pore sizes immersed the feed fluid into the device through the feed inlet, applying a driving force to drive the feed through the filtration device, passing the feed through the filtration device such that a substantial fraction of the particles of the at least one population are retained as retentate in the first flow chamber, and a substantial fraction of the feed fluid pass through the filter as filtrate into the second flow chamber, collecting the retentate at the retentate outlet, and collecting the filtrate at the filtrate outlet.

In accordance with some embodiments, providing a filtration device comprises providing a filtration device which includes more than 10 filtration units.

In accordance with some embodiments, introducing the feed into the device comprises introducing a liquid suspension of cells into the first flow chamber.

In accordance with some embodiments, the feed comprises viable cells, and the method further comprises separating cells from the feed, wherein at least about 90% of the viable cells remain viable after separation.

In accordance with some embodiments, the method further comprises separating the cells from the feed, and wherein less than about 0.03 percent of the cells are lysed by the filtration device.

In accordance with some embodiments, less than about 0.03% of the cells are trapped in the filtration device.

In accordance with some embodiments, passing the feed through the filtration device comprises passing more than $10^5$ cells per second through the filtration device.

In accordance with some embodiments, passing the feed through the filtration device comprises passing more than $10^6$ cells per second through the filtration device.

In accordance with some embodiments, passing the feed through the filtration device comprises passing more than $10^7$ cells per second through the filtration device.

In accordance with some embodiments, providing the filtration device comprises providing a filtration device comprising at least one filtration unit having a hold up volume of smaller than 0.8 microliter.

In accordance with some embodiments, providing the filtration device comprises providing a filtration device having a footprint area and a substantially constant chamber depth, and wherein passing the feed through the filtration device comprises passing cells through the filtration device at a normalized processing speed, defined as the number of cells passing through the filtration device per second divided by the product of the substantially constant chamber depth and the footprint area, of greater than 10,000 cells per second per cubic millimeter.

In accordance with some embodiments, providing the filtration device comprises providing a filtration device having a footprint area and a substantially constant chamber depth, and wherein passing the feed through the filtration device comprises passing cells through the filtration device at a normalized processing speed, defined as the number of cells passing through the filtration device per second divided by the product of the substantially constant chamber depth and the footprint area, of greater than 100,000 cells per second per cubic millimeter.

In accordance with some embodiments, providing the filtration device comprises providing a filtration device having a characteristic chamber depth, a footprint area, and a filtration unit density, defined as the number of filtration modules included in the module divided by the product of the characteristic chamber depth and the footprint area, wherein the filtration unit density is greater than 400 filtration units per cubic centimeter.

In accordance with some embodiments, introducing the feed into the device comprises introducing a feed liquid including bone marrow into the first flow chamber.

In accordance with some embodiments, introducing the feed into the device comprises introducing a feed liquid including blood into the first flow chamber.

In accordance with some embodiments, introducing the feed comprises introducing a feed liquid including umbilical cord blood into the first flow chamber.

In accordance with some embodiments, introducing the feed comprises introducing a feed liquid including stem cells into the first flow chamber.

In accordance with some embodiments, introducing the feed comprises introducing a feed liquid including colony forming cells into the first flow chamber. In accordance with some embodiments, introducing the feed comprises introducing a feed liquid including immune cells into the first flow chamber.

In accordance with some embodiments, introducing the feed into the device comprises introducing amniotic fluid into the first flow chamber.

In accordance with some embodiments, introducing the feed into the device comprises introducing digested adipose tissue into the first flow chamber.

In accordance with some embodiments, introducing the feed into the device comprises introducing one of cells, blood cells, cord blood cells, bone marrow cells, erythrocytes, leukocytes, lymphocytes, epithelial cells, stem cells, cancer cells, tumor cells, circulating tumor cells, progenitor cells, cell precursors, cord blood stem cells, hematopoietic stem cells, mesenchymal stem cells, adipose stem cells, pluripotent stem cells, induced pluripotent stem cells, embryonic stem cells, cells derived from umbilical cord, cells derived from fat tissues, cells in stromal vascular fractions (SVF), cells in amniotic fluids, cells in menstrual blood, cells in cerebral spinal fluid, cells in urine, bone marrow stem cells, peripheral blood stem cells, CD34+ cells, colony forming cells, T cells, B cells, neural cells, immuno cells, dendritic cells, megakaryocytes, immobilized bone marrow cells, platelets, sperms, eggs, oocytes, microbes, microorganisms, bacteria, fungi, yeasts, protozoans, viruses, organelles, nuclei, nucleic acids, mitochondria, micelles, lipids, proteins, protein complexes, cell debris, parasites, fat droplets, multicellular organisms, spores, algae, clusters, aggregates of the above, industrial powders, polymers, powders, emulsions, droplets, dusts, microspheres, particles, and colloids into the first flow chamber.

In accordance with some embodiments, the feed comprises particles having sizes between about 5 μm and about 30 μm.

In accordance with some embodiments, the method further comprising collecting retentate particles including one of cells, CD34+ cells, a stromal vascular fraction, stem cells, progenitor cells, colony forming cells, hematopoietic stem cells, adipose stem cells, mesenchymal stem cells, amniotic stem cells, nucleated cells, leukocytes, lymphocytes, cancer cells, tumor cells, dendritic cells, dead cells, live cells, dividing cells, reticulocytes, red blood cells, fat cell, and fat droplets.

In accordance with some embodiments, collecting retentate particles comprises collecting cells and wherein greater than about 95% of the cells in the retentate are viable.

In accordance with some embodiments the method further comprises collecting filtrate including one of cells, CD34+ cells, a stromal vascular fraction, stem cells, progenitor cells, colony forming cells, hematopoietic stem cells, adipose stem cells, mesenchymal stem cells, amniotic stem cells, plasma, platelets, red blood cells, nucleated cells, leukocytes, lymphocytes, cancer cells, tumor cells, dendritic cells, dead cells, live cells, dividing cells, reticulocytes, red blood cells, fat cell, and fat droplets.

In accordance with some embodiments, collecting the filtrate comprises collecting cells and wherein greater than about 95% of the cells in the filtrate are viable.

In accordance with some embodiments, the method further comprises providing a filtration device having a retention size significantly smaller than the physical pore sizes.

In accordance with another aspect of the present disclosure there is provided a method for cord blood volume reduction. The method comprises procuring a sample comprising umbilical cord blood having at least one population of nucleated cells, the sample having a sample volume. The method further comprises providing a filtration device. The filtration device includes a first collection receptacle, a second collection receptacle, a feed access means, and at least three filtration units. Each filtration unit has a microfluidic flow chamber including a feed inlet, a retentate outlet, and a filtrate outlet. The microfluidic flow chambers include at least one dimension which is perpendicular to a length thereof which is smaller than about 1 millimeter. The feed inlet is in fluid communication with the feed access means. The retentate outlet is in fluid connection with the first collection receptacle. The filtrate outlet is in fluid connection with the second collection receptacle. The method further comprises introducing the sample to the feed inlets of the filtration units using the feed access means, applying a driving force to the sample, passing the sample through the microfluidic flow chambers of the filtration device, creating laminar flow conditions that direct a substantial fraction of the sample volume to the filtrate outlet and a substantial fraction of the at least one population of nucleated cells to the retentate outlet, collecting a fluid output from the retentate outlet in the first collection receptacle, and collecting a fluid output from the filtrate outlet in the second collection receptacle.

In accordance with some embodiments, collecting the fluid output from the retentate outlet comprises collecting greater than 70% of the nucleated cells from the sample in a volume of less than 25% of the sample volume in the first collection receptacle.

In accordance with some embodiments, the at least one population of nucleated cells comprises CD34+ cells and collecting the fluid output from the retentate outlet comprises collecting greater than 75% of the CD34+ cells from the sample into the first collection receptacle.

In accordance with some embodiments, the method further comprises separating viable cells from the sample, and wherein at least about 95% of the viable cells remain viable after separation.

In accordance with some embodiments, procuring a sample comprises procuring a sample comprising umbilical cord blood nucleated cells of greater than about 95% viability, and wherein collecting the fluid output from the retentate outlet comprises collecting nucleated cells of greater than about 95% viability.

In accordance with some embodiments, passing the sample through the microfluidic flow chambers comprises passing more than 10,000,000 blood cells per second through the filtration device.

In accordance with another aspect of the present disclosure, there is provided a particle filtration apparatus. The particle filtration apparatus comprises a common feed inlet, a common filtrate outlet, a common retentate outlet, and at least one high module density device. The at least one high module density device includes a plurality of filtration units. Each of the filtration units includes a first flow chamber includes at least one inlet configured to receive a feed comprising feed particles in a feed fluid, and at least one retentate outlet, a second flow chamber including a proximal end, a distal end having at least one filtrate outlet, and a first filter positioned between the first flow chamber and the second flow chamber. The first filter includes a first row of pillars, and a plurality of pores defined by spacings between adjacent pillars of the row of pillars. Each pore of plurality of pores includes a physical pore size defined by a distance between the adjacent pillars which define the pore. The particle filtration apparatus further comprises means for moving the feed through the plurality of filtration units. The first flow chamber, the second flow chamber, the filter, and the means for moving the feed through the plurality of filtration units are configured to have a retention size smaller than the effective pore sizes of the pores, and to retain a substantial fraction of the feed particles having a size greater than the retention size as retentate in the first flow chamber, and pass a substantial fraction of the feed fluid as filtrate into the second flow chamber. Each of the at least one inlets of the plurality of filtration units is in fluid communication with the common feed inlet. Each of the at least one filtrate outlets of the plurality of filtration units is in fluid communication with the common filtrate outlet. Each of the at least one retentate outlets of the plurality of filtration units is in fluid communication with the common retentate outlet.

In accordance with some embodiments, the particle filtration apparatus further comprises a tube, a tube cap, and a tube insert. The high module density device may be configured to be mounted within the tube insert. The tube may be configured to accommodate the tube insert. The tube insert may include a feed reservoir in fluid connection with the common feed inlet. The tube cap may be configured to cover the tube and the tube insert.

In accordance with some embodiments, the tube is configured to receive retentate from the high module density device. The tube insert may further include a filtrate reservoir configured to receive filtrate from the high module density device.

In accordance with some embodiments, the tube is configured to receive filtrate from the high module density device. The tube insert may further include a retentate reservoir configured to receive retentate from the high module density device.

In accordance with some embodiments, the tube insert further includes a carrier fluid reservoir configured to supply a carrier fluid to an inlet of at least one first flow chamber.

In accordance with some embodiments, the particle filtration apparatus further comprises a retentate collection bag in fluid connection with the common retentate outlet and a filtrate collection bag in fluid connection with to the common filtrate outlet.

In accordance with some embodiments, the particle filtration apparatus further comprises a common carrier fluid inlet in fluid connection with an inlet of at least one first flow chamber.

In accordance with some embodiments, the particle filtration apparatus further comprises a carrier fluid receptacle configured to supply a carrier fluid to the carrier fluid common inlet.

In accordance with some embodiments, the particle filtration apparatus further comprises an adaptor configured to establish a fluid connection between a feed collection bag and the common feed inlet.

In accordance with some embodiments, the particle filtration apparatus further comprises a feed collection bag in fluid connection with the common feed inlet.

In accordance with some embodiments, the feed collection bag comprises at least one needle configured to draw feed into the feed collection bag.

In accordance with some embodiments, the feed collection bag contains an anticoagulant.

In accordance with some embodiments, the feed collection bag contains a fluid.

In accordance with some embodiments, the particle filtration apparatus further comprises a first well in fluid communication with the common feed inlet and configured as a fluid reservoir, a second well in fluid communication with the common retentate outlet and configured as a fluid reservoir, and a third well in fluid communication with the common filtrate outlet and configured as a fluid reservoir.

In accordance with some embodiments, the first well, the second well, and the third well are configured in a multi-well plate format.

In accordance with some embodiments, the particle filtration apparatus further comprises a fourth well in fluid communication with the inlet of at least one first flow chamber and configured to supply a carrier fluid to at least one first flow chamber.

In accordance with some embodiments, the particle filtration apparatus further comprises a cap configured to enclose at least one of the first well, the second well, and the third well.

In accordance with some embodiments, the cap comprises a foil substantially impermeable to air and vapor and configured to seal the at least one of the first well, the second well, and the third well.

In accordance with some embodiments, at least one of the first well, the second well, and the third well contains a fluid.

In accordance with some embodiments, each filtration unit of the plurality of filtration units has a hold up volume of smaller than 1 microliter.

In accordance with some embodiments, the high module density device has a filtration unit density of greater than 500 filtration units per cubic centimeter.

In accordance with some embodiments, the high module density device includes more than 30 filtration units.

In accordance with some embodiments, the high module density device has a design efficiency index of greater than about $0.5$ $mm^{-2}$.

In accordance with some embodiments, the high module density device has a design efficiency index of greater than about 5 $mm^{-2}$.

In accordance with another aspect of the present disclosure there is provided a filter device. The filter device comprises a first flow chamber including at least one inlet configured to introduce a feed comprising particles and at least one retentate outlet configured to collect a retentate of the feed. The filter device further comprises a second flow chamber including a first end and at least one filtrate outlet, the at least one filtrate outlet configured to collect a filtrate. The filter device further comprises a first filter. The first filter includes a plurality of pores having a physical pore size and a retention size which is smaller than the physical pore size. The first filter is disposed between the first flow chamber and the second flow chamber. The first flow chamber, the second flow chamber and the first filter are configured to facilitate flow conditions that substantially increase a retention rate of particles smaller than the physical pore size and larger than a retention size.

In accordance with some embodiments, the filter device is configured to satisfy the "filtrate chamber expansion criterion."

In accordance with some embodiments, an angle between a tangent line of a sidewall of the second flow chamber and a tangent line of the first filter is less than about 5 degrees.

In accordance with some embodiments, the retention size is smaller than about 90 percent of the physical pore size of the pores.

In accordance with some embodiments, the filter device is configured to flow a fluid through each pore at a volumetric flow rate of less than about 3 percent of a volumetric flow rate at the at least one inlet of the first flow chamber.

In accordance with some embodiments, the filter device has a length to width ratio of more than about 10.

In accordance with some embodiments, the first flow chamber has substantially a first constant depth. The second flow chamber may have a substantially a second constant depth, and the second flow chamber may expand in width from the first end of the second flow chamber towards the at least one filtrate outlet of the second flow chamber.

In accordance with some embodiments, the filter device is configured to flow a fluid through the first chamber at a substantially constant flow speed.

In accordance with some embodiments, the filter device is configured to flow a fluid through the second chamber at a substantially constant flow speed.

In accordance with some embodiments, the filter device is configured to flow a fluid through substantially all of the pores at a substantially identical flow rate.

In accordance with some embodiments, the first filter comprises a row of pillars, wherein the pores of the first filter comprise fluid passages between adjacent pillars of the row of pillars, and wherein the row of pillars comprises no fewer than 10 percent of all the pillars present in the device.

In accordance with some embodiments the first chamber comprises at least one carrier fluid inlet distinct from the at least one inlet and configured to introduce a carrier fluid into the first flow chamber.

In accordance with some embodiments, the filter device is free of any leading edge having a radius of curvature smaller than 0.5 µm, along a flow path through the device.

In accordance with some embodiments a first subset of the pores has a different physical pore size than a second subset of the pores.

In accordance with some embodiments, the at least one filtrate outlet of the second flow chamber is configured to collect the filtrate passed through the first subset of pores and wherein the second flow chamber comprises a second filtrate outlet configured to collect filtrate passed through the second subset of pores.

In accordance with some embodiments, the filter device further comprises a second filter and a third flow chamber, wherein the second filter is disposed between the first flow chamber and the third flow chamber, and wherein the third flow chamber comprises at least one outlet.

In accordance with some embodiments, the filter device has a length to width ratio of greater than about 5.

In accordance with some embodiments, the first filter comprises a first row of pillars. The pores of the first filter may comprise fluid passages between adjacent pillars of the first row of pillars. The second filter may comprise a second row of pillars. The pores of the second filter may comprise fluid passages between adjacent pillars of the second row of pillars. The first row of pillars and the second row of pillars may comprise no fewer than 10 percent of all the pores present in the filter device.

In accordance with some embodiments the filter device is substantially symmetric about a minor plane going through a center of the first flow chamber.

In accordance with some embodiments the filter device further comprises a second filter and a third flow chamber, wherein the second filter is disposed between the second flow chamber and the third flow chamber, and wherein the third flow chamber comprises at least one inlet and at least one outlet.

In accordance with some embodiments, the filter device further comprises a second filter, a third flow chamber, and a fourth flow chamber, wherein the second filter is disposed between the third flow chamber and the fourth flow chamber, wherein the third flow chamber comprises at least one inlet and at least one outlet, and wherein the fourth flow chamber comprises at least one outlet.

In accordance with some embodiments, the filter device has less than about 6,000 pillars.

In accordance with some embodiments, the first filter and the second filter comprise no fewer than 10 percent of the pores included in the device.

In accordance with some embodiments, the at least one inlet of the third flow chamber is in fluid connection with the at least one filtrate outlet of the second flow chamber.

In accordance with some embodiments, the at least one inlet of the third flow chamber is in fluid connection with the at least one retentate outlet of the first flow chamber.

In accordance with some embodiments, the at least one inlet of the third flow chamber is in fluid connection with the at least one outlet of the first flow chamber and with the at least one outlet of the second flow chamber.

In accordance with some embodiments, the third flow chamber further comprises at least one carrier fluid inlet distinct from the at least one inlet and configured to introduce a carrier fluid.

In accordance with some embodiments, the at least one outlet of the third flow chamber is configured to collect a retentate from the first filter. The third flow chamber may further comprise a second outlet distinct from the at least one outlet. The second outlet of the third flow chamber may be configured to collect a retentate from the second filter.

In accordance with some embodiments, the at least one outlet of the third flow chamber is configured to collect a retentate from the first filter and a retentate from the second filter.

In accordance with some embodiments, the at least one outlet of the third flow chamber is configured to collect a retentate from the first filter and a retentate from the second filter. The third flow chamber may further comprise a second outlet distinct from the at least one outlet. The second outlet of the third flow chamber may be configured to collect a filtrate from the first filter.

BRIEF DESCRIPTION OF THE DRAWINGS

The accompanying drawings are not intended to be drawn to scale and the number of elements (for example, the number of pillars) may be reduced from what would be present in an actual embodiment for the sake of legibility. In the drawings, each identical or nearly identical component that is illustrated in various figures is represented by a like numeral. For purposes of clarity, not every component may be labeled in every drawing. In the drawings:

FIG. 1A illustrates the exclusion of a large particle from a small pore. FIG. 1B illustrates the deformation of a large particle, which partially enters a pore, but is unable to squeeze through the pore. FIG. 1C shows a particle entering a narrowing opening, and getting trapped within the pore. FIG. 1D shows particles trapped in pores. FIG. 1E shows the failure of size exclusion. In this diagram, a particle goes through a pore because the particle is smaller than the pore. FIG. 1F shows another failure in size exclusion. In this case, the particle goes through a pore because it may deform and squeeze through the pore. FIG. 1G illustrates another failure in size exclusion. In this case, particles fail to be filtered because their flow path does not provide for them to encounter physically restricting pores.

FIG. 2A shows the flow exclusion effect observed in microcapillaries of blood circulation. FIG. 2B shows a possible mechanism for flow exclusion.

FIG. 5A illustrates a top view schematic diagram. FIG. 5B provides a three dimensional assembled view. FIG. 5C provides a three dimensional exploded view. FIG. 5D provides a three dimensional view showing pillars with an aspect ratio smaller than one. The lid of the filter module embodiment is not shown. FIG. 5E provides a three dimensional view showing pillars with an aspect ratio greater than one. The lid of the embodiment is not shown. FIG. 5F provides a three dimensional view showing tapered pillars. The lid of the embodiment is not shown.

FIG. 7A provides a top view of a filter module embodiment. FIG. 7B provides a top view of a filter module embodiment.

FIG. 9A illustrates a wavy filtrate chamber. FIGS. 9B-9H show various cross sectional shapes of pillars.

FIGS. 10A and 10B are a top view and a three dimensional view, respectively. The lid of the module is not shown. FIG. 10C illustrates a particle moving in the module.

FIGS. 14A and 14B are schematic diagrams showing top views of two dual filter modules.

FIGS. 17A-17D are schematic diagrams. FIG. 17A provides a top view of a filter cascade module comprising two substantially identical filter modules. FIG. 17B provides a top view of a filter cascade module comprising two substantially identical dual filter modules. FIGS. 17C and 17D provide top views of two filter cascade modules each comprising two dual filter modules.

FIG. 20A provides a top view of a filter cascade module comprising two different filter modules. FIG. 20B provides a top view of a simplified filter cascade module.

FIGS. 21A and 21B are schematic diagrams that provide top views of two dual filter modules.

FIGS. 23A-23C are schematic diagrams that provide top views of three dual filter module configurations.

FIGS. 24A-24D and 24F provide top views of high module density devices. FIG. 24E provides a three dimensional view of a high module density device. The lid of the device is not shown.

FIG. 26A is a schematic diagram showing a three dimensional assembled view of the cartridge. FIG. 26B is a schematic diagram showing a front view of the cartridge. FIG. 26C is a schematic diagram showing a side view of the cartridge. FIG. 26D is a schematic diagram showing a three dimensional exploded view of the cartridge. FIG. 26E is a schematic diagram showing a side exploded view of the cartridge.

FIGS. 29A and 29B are schematic diagrams showing respectively a three dimensional assembled view and a three dimensional exploded view of a tube system.

FIGS. 30A-30G are schematic diagrams of a tube insert. FIG. 30A is a schematic diagram showing a three dimensional view of the tube insert. FIG. 30B is a schematic diagram showing a cross-sectional view of the tube insert. FIGS. 30C, 30D, 30E, 30F, and 30G are schematic diagrams showing respectively a top view, a front view, a side view, a rear view, and a bottom view of the tube insert.

FIG. 31A is a schematic diagram showing a three dimensional view of the plate system. FIG. 31B is a schematic diagram showing a three dimensional exploded view of the plate system. FIG. 31C is a schematic diagram showing a side view of the plate system.

FIG. 32A is a schematic diagram showing a three dimensional view of the plate system. FIGS. 32B, 32C, and 32D are schematic diagrams showing respectively a top view, a side view, and a front view of the plate system.

FIG. 33 is a table showing experimental results of leukocyte isolation from whole peripheral blood using a high module density device.

FIGS. 34A-34B are histograms showing leukocyte (WBC), erythrocyte (RBC) and platelet (PLT) size distributions in the blood samples and in the retentates used in an experiment where lymphocytes are isolated from peripheral blood. FIG. 34C is a table showing counts of various cell types. FIG. 34D is a table showing the performance of a high module density device.

FIGS. 35A-35C are tables showing experimental results of umbilical cord blood volume reduction using a high module density device.

DETAILED DESCRIPTION

Figure 1A:
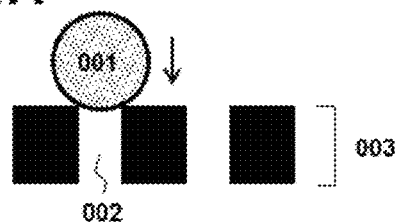
FIGS. 1A-1G are schematic diagrams showing various methods for particle isolation.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Aspects and embodiments of the present disclosure are directed to filtration systems that may be useful for particle filtration and to methods of operating such filtration systems.

Aspects and embodiments of the disclosure are based, at least in part, on the discovery of a device that employs flow exclusion and that provides high capacity, high throughput, low particle damage, low shear, and clogging resistant filtration of particles and biological samples. Further, the present disclosure provides a method and device that can be easily manufactured as a compact device, using inexpensive materials including, but not limited to, silicon and plastics.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example, within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The term "particles" as use herein includes, but is not limited to, cells, blood cells, cord blood cells, bone marrow cells, erythrocytes, leukocytes, lymphocytes, epithelial cells, stem cells, cancer cells, tumor cells, circulating tumor cells, progenitor cells, cell precursors, cord blood stem cells, hematopoietic stem cells, mesenchymal stem cells, adipose stem cells, pluripotent stem cells, induced pluripotent stem cells, embryonic stem cells, cells derived from umbilical cord, cells derived from fat tissues, cells in stromal vascular fractions (SVF), cells in amniotic fluids, cells in menstrual blood, cells in cerebral spinal fluid, cells in urine, bone marrow stem cells, peripheral blood stem cells, CD34+ cells, colony forming cells, T cells, B cells, neural cells, immuno cells, dendritic cells, megakaryocytes, immobilized bone marrow cells, Wharton's jelly stem cells, eukaryotic cells, prokaryotic cells, animal cells, platelets, sperms, eggs, oocytes, microbes, microorganisms, bacteria, fungi, yeasts, protozoans, viruses, organelles, nuclei, nucleic acids, mitochondria, micelles, lipids, proteins, protein complexes, cell debris, parasites, fat droplets, multi-cellular organisms, spores, algae, clusters or aggregates of the above, as well as other non-biological particles suspended in fluid, such as industrial powders, polymers, powders, emulsions, droplets, dusts, microspheres, and colloids. The particles may be rigid or deformable, and could have a variety of sizes and shapes. The particles may range in size, e.g. may have a maximum dimension, from about 50 nm to about 1 mm. The shape of particles may be, but are not limited to, oblong, spherical, disc-like, box-like, rod-like, spiral, or chains or aggregates of the above. Embodiments of the present disclosure may be useful for the filtration of particles that are deformable, fragile, or vulnerable to large shear stress.

"Mechanical properties" include, but are not limited to, physical dimensions, size, shape, deformability, flexibility, elasticity, density, viscosity, rigidity, and the spatial distributions or time response of the above characters.

The term "size exclusion" as used herein comprises preventing or restricting entrance or passage by physical blocking. An embodiment of size exclusion is to use small pores 002 to prevent large non-deformable particles 001 from entering the pores and from passing through the filter 003 (FIG. 1A). Another embodiment of size exclusion is to use a small opening to prevent a deformable particle 001 from squeezing into and pass through the opening 002 (FIG. 1B). Yet another embodiment of size exclusion is shown in FIG. 1C, where a particle 001 may enter, a wide opening of a pore 002, and get stuck at the narrow part of the pore 002. Yet another embodiment of size exclusion is shown in FIG. 1D. A particle 001 may enter a pore 002, and get trapped inside the filter 003.

Figure 1E:
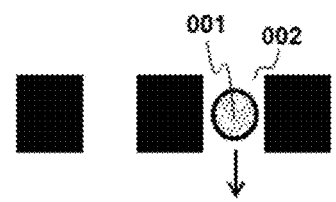
Figure 1B:
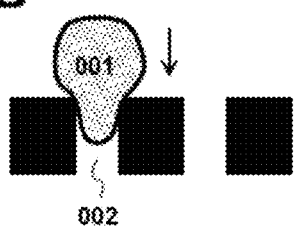
Figure 1F:
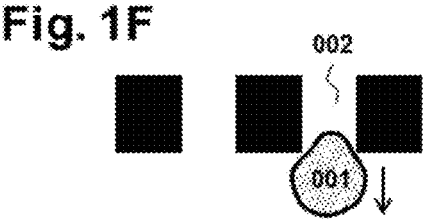
Figure 1C:
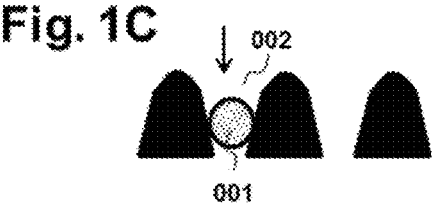
Figure 1G:
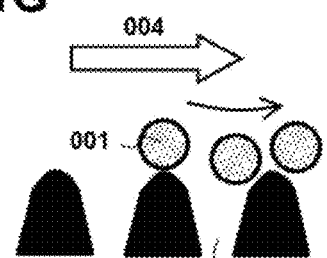
Figure 1D:
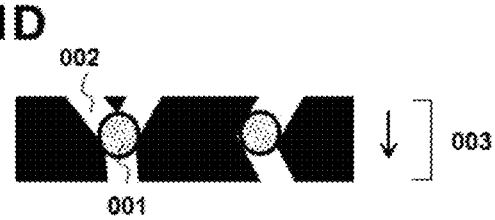

The term "size exclusion" as used herein also comprises "physical restriction." FIGS. 1E, 1F and 1G show examples where particles are not size excluded or physically restricted by a filter. A particle 001 may be too small to be excluded by the pores 002 (FIG. 1E). A particle 001 may also be so deformable that it squeezes through a pore 002 under a driving force (FIG. 1F). In FIG. 1G, particles 001 are driven by a tangential force 004 so that they do not move into the narrow parts of the pores 002 which may otherwise trap the particles. Particles in FIGS. 1E, 1F and 1G are not considered to be size excluded or physically restricted by the filter.

The term "filtration" as used herein generally comprises, but is not limited to, particle separation, fractionation, particle isolation, washing, concentration, enrichment, purification and/or buffer exchange, in a particle separation device with or without the use of a filter. "Filtration" is also used to refer to partial or complete removal or retention of one or more particle populations. The term "filtration" as used herein also includes specific applications such as cell separation, stem cell isolation, leuko-reduction, leukocyte isolation, cancer cell isolation, cord blood volume reduction, plasma skimming, and generation of stromal vascular fractions (SVF).

A "filter" as used herein refers to, but is not limited to, a structure comprising multiple openings or fluid passages, called "pores." The term "pore" as used herein comprises an opening or a fluid passage, for example on or in a filter. The cross sectional shape of a pore may be, but is not limited to, circular, rectangular, round, polygonal, irregular, long and narrow, or slit-like. The term "pore" as used herein includes, but is not limited to, the space between pillars. As used herein, one embodiment of a pore is the space between two adjacent pillars in a fluidic channel. Another embodiment of a "pore" is a gap between a weir structure in and a ceiling of a fluidic channel.

A filter may be used to partially or completely allow passage of certain particles, and/or disallow passage or reduce a flux of other particles. As the term is used herein, "filters" are not limited to sieves where particles are blocked or separated based on size exclusion. As used herein, one embodiment of a filter comprises a physical structure, including obstacles and pores. Another embodiment of a filter comprises a physical structure that separates particles using bifurcating flows and pores larger than retentate particles. Yet another embodiment of a filter comprises a physical structure that retains particles smaller than the pore openings of the physical structure using flow forces or fluid dynamic forces. Yet another embodiment of a filter comprises a hydrophilic pattern on a hydrophobic surface to create "pores" or avenues of fluid passage for aqueous solutions.

To "filter," as used herein, means to perform filtration using a filter.

The term "retentate" as used herein comprises particles that are retained by a filter or that do not pass through a filter. "Retentate" as used herein may also include the fluid that comprises retained particles. "Retentate" as used herein may also refer to the fluid and particle output that comprises particles retained by a filter in an embodiment of the present disclosure. "Retentate" as used herein may also refer to the fluid output comprising particles of interest, using a separation device, which may or may not comprise a filter structure.

The term "filtrate" as used herein comprises particles that pass through a filter. "Filtrate" as used herein may also comprise the fluid that contains the particles that pass through the filter. "Filtrate" as used herein may also refer to the fluid and particle output that comprises particles that pass through a filter in an embodiment of the present disclosure. "Filtrate" as used herein may also refer to the fluid output comprising a fluid in which particles of interest are partially or fully removed, using a separation device, which may or may not comprise a filter structure.

The term "feed" as used herein comprises particles that are to be processed by a filtration process, or particles that are entering a filtration device. The term "feed" may also comprise a fluid that contains the particles to be processed by the filtration process. The term "feed" as used herein may include, but is not limited to, particles, bloods, umbilical cord bloods, serums, fat tissues, digested fat tissues, stromal vascular fractions, amniotic fluids, menstrual bloods, cerebral spinal fluids, milk, bone marrows, urines and other bodily fluids.

The term "retention rate" of a particle as used herein refers to the probability that the particle is retained by a filter incorporated in a device. The term "retention rate" of a particle population as used herein refers to the proportion of the particle population that is collected as the retentate of a device. The term "retention rate" of a fluid as used herein also refers to the proportion of the fluid that is collected as the retentate by a device. The device herein may comprise a filter, a filtration module, a filtration unit, or a filtration system. For example, the "retention rate" of a substantially uniform particle population may be calculated as the ratio between the number of the particles in the resulting retentate and the number of the particles in the feed that are processed. The retention rate of a certain particle population may refer to the proportion of such population in the feed that is collected as the retentate in a filtration process. The "retention rate" may also be referred to as the "recovery yield" or "carryover".

The term "physical pore size" as used herein refers to the size of the physical spacing of a pore. In practice, the "physical pore size" of a pore may be essentially measured as the maximum diameter of a non-deformable sphere, e.g. a polymer microsphere, that can pass through the pore without substantial physical restriction or size exclusion under "dead-ended" filtration configurations. For example, a pore comprising the spacing of two pillars that are 10 μm apart in a 50 μm deep microfluidic channel has a physical pore size of 10 μm. Similarly, a pore comprising a circular hole of 5 μm diameter in a membrane has a physical pore size of 5 μm. If a pore comprises a slit, the physical pore size is substantially the width of the slit. Dead-ended filtration is described extensively in the following reference: Zeman, L. J. et al. "Microfiltration and Ultrafiltration" Marcel Dekker, Inc., ISBN 0-8247-9735-3, p. 328-331 (1996), the disclosed description of dead-ended filtration of which is hereby incorporated herein by reference.

The "effective pore size" of a pore as used herein refers to the minimum diameter of a non-deformable sphere, e.g. a polymer microsphere, that can be retained substantially by the pore under the flow conditions of interest. An effective pore size can be experimentally measured and determined. For example, a baseline retention rate by a pore can be established using small non-deformable spheres that substantially track the flow streamlines when flowing through the pore under the flow conditions of interest, without flow exclusion. Larger non-deformable spheres may be retained due to flow exclusion by the pore at higher retention rates than the baseline, under substantially the same operating conditions. The diameter of the smallest non-deformable sphere that can be retained at a substantially higher retention rate than the baseline, e.g. 40%, 50%, 60%, 80%, 90%, 98%, 99%, or 100% higher than the baseline, is referred to as the "effective pore size" of the pore. When measuring the effective pore size, it is preferred that the particles used have the following characteristics: (a) the particles are substantially spherical; (b) the particles are substantially non-deformable and rigid; (c) the particles are suspended in substantially single particle suspensions; (d) the particle suspension is dilute and there is substantially no particle-particle interaction; (e) the particles do not settle substantially over time periods of interest; (f) the particles do not substantially stick to or foul the fluidic channel or the filter surfaces; and (g) the particles do not interact with each other or with the fluidic channel, the filter surfaces or the pores due to electric charge, sticking, affinity, or magnetic forces. It is understood that the above particle characteristics are not meant to be limiting.

The "retention size" of a device as used herein refers to the minimum diameter of a non-deformable sphere, e.g. a polymer microsphere, that has a retention rate substantially higher than, for example, about 40%, 50%, 60%, 80%, 90%, 98%, 99%, or 100% higher than the retention rate of a fluid processed using the device in substantially the same operating conditions. The retention size of a device can be experimentally measured and determined. For example, the retention rate of a fluid may be established as a baseline using small non-deformable spheres that substantially track the flow motion of the fluid under a set of operating conditions. Larger non-deformable spheres mixed in the fluid may have a higher retention rate than the baseline under substantially the same operating conditions. The diameter of the smallest non-deformable sphere that has a retention rate substantially higher than the baseline, for example, about 40%, 50%, 60%, 80%, 90%, 98%, 99%, or 100% higher than the baseline, is characterized as the "retention size" of the device. The device herein may comprise a filter, a filtration module, a filtration unit, or a filtration system. When measuring the retention size, the particles used may have the following characteristics: (a) the particles are substantially spherical; (b) the particles are substantially non-deformable and rigid; (c) the particles are suspended in substantially single particle suspensions; (d) the particle suspension is dilute and there is substantially no particle-particle interaction; (e) the particles do not settle substantially over time periods of interest; (f) the particles do not substantially stick to or foul the fluidic channel or the filter surfaces; and (g) the particles do not interact with each other or with the fluidic channel, the filter surfaces or the pores due to electric charge, sticking, affinity, or magnetic forces. It is understood that the above particle characteristics are not meant to be limiting.

The term "flow exclusion" as used herein refers to using fluid flow conditions around a pore to achieve an effective pore size substantially smaller than the physical pore size. The term "flow exclusion" as used herein also refers to using fluid flow configurations around a filter to achieve a retention size substantially smaller than the physical pore size of the constituting pores of the filter.

It is appreciated that the above definitions are meant to convey the spirit of the present disclosure, and are not meant to be limiting.

Particle Filtration Device

Aspects and embodiments of the present disclosure provide a device for particle filtration comprising (a) a first flow chamber having at least one inlet and at least one outlet; (b) a second flow chamber having at least one outlet; and (c) a filter comprising a plurality of pores, for example, at least 10 pores. Here, the filter is disposed between the first flow chamber and the second flow chamber and has a physical pore size of between about 10 nm and about 10 mm. The first flow chamber and second flow chamber are configured such that the effective pore size of the filter pores is substantially smaller, for example, up to about 95% smaller than the physical pore size. The device may be made of materials including, for example, silicon, glass or plastic. Some embodiments may be constructed so that particles encounter no sharp edges, reducing damage.

A particle filtration device in accordance with aspects and embodiments of the present disclosure may be configured in several different ways. In some embodiments, the first flow chamber has at least one inlet that can be used to introduce a carrier fluid. Other embodiments comprise a second filter and a third flow chamber, wherein said second filter is disposed between said first flow chamber and said third flow chamber and wherein said third flow chamber comprises at least one outlet. Still other embodiments comprise a second filter and a third flow chamber having at least one outlet so that the second filter is disposed between the second flow chamber and a third flow chamber.

In some embodiments particles are driven through the device by at least one of the following: a fluid flow, a hydrodynamic flow, a pressure drop, a hydrodynamic pressure, a pressure source, a vacuum, a head height, gravity, a centrifugal force, an electric field, an electrophoretic field, an electrokinetic force, an electro-osmotic force, a capillary action or a combination of the above. In some embodiments the particles ("feed particles") pass through or are processed through the device at a rate of at least about 100 feed particles, e.g. at least $10^2$, $10^3$, $10^4$, $10^5$, $10^6$, $10^7$, $10^8$, $10^{10}$, $10^{12}$, or $10^{15}$ per second. In some embodiments the device has a hold up volume smaller than 500 nl, 200 nl, 100 nl, 50 nl, 20 nl or 10 nl. In some embodiments the particles undergo a shear stress that is not damaging to the particles.

Embodiments of the filter can be formed in multiple ways. In some embodiments the filter has one or more rows of pillars or protrusions. The pillars or protrusions can be of a variety of shapes and sizes. In other embodiments there are at least two rows of pillars or protrusions. Other embodiments of the disclosure provide a filter formed from a membrane comprising pores. Still other embodiments of the disclosure provide a filter formed from a screen filter. In some embodiments the filter is constructed so that the particles do not encounter any sharp edges so that the potential for damage to the particles is reduced or eliminated. This may be important when the particles are living or apoptotic cells.

In some embodiments of the disclosure, the filter comprises pores whose effective pore size is smaller than their physical pore size by at least about 0.5 μm. In other embodiments the effective pore size is smaller than 95% of the physical pore size. In still other embodiments the effective pore size may be substantially smaller than the physical pore size, e.g. the effective pore size is about 75%, about 60%, about 50%, about 30%, about 10%, or about 5% of the physical pore size. In yet other embodiments, the retention size may be substantially smaller than the physical pore size, for example, the effective pore size may be about 90%, about 75%, about 60%, about 50%, about 30%, about 10%, or about 5% of the physical pore size. In yet other embodiments a particle encounters no more than about 5,000 pores during its passage through the device.

Aspects and embodiments of the present disclosure can be used to filter, separate, fractionate, process, enrich, or isolate many types of particles such as simple or complex sediments, detriments or heavy metal contaminants found in wastewater or various contaminants found in naturally occurring or synthesized fluids such as oil, biofuels or the like. In addition, some aspects and embodiments of the disclosure can be used for clinical purposes to filter many different types of cells such as those that are healthy, diseased, growing, dying or dead. Examples of cell types are blood cells, stem cells, hematopoietic stem cells, progenitor cells, mesenchymal stem cells, adipose stem cells, CD34+ cells, tumor cells, bone marrow cells, cord blood cells, lymphocytes, leukocytes, cancer cells, cerebral spinal fluid cells, amniotic fluid cells, Wharton's jelly stem cells, eukaryotic cells, prokaryotic cells, animal cells, stromal vascular fraction cells, umbilical cord derived cells, liver cells, neuron cells and immune cells. Other cell types include bacterial cells, yeast cells and abnormal cells.

Aspects and embodiments of the present disclosure can be used to process, filter, separate, or fractionate many types of fluids such as bloods, umbilical cord bloods, serums, fat tissues, digested fat tissues, stromal vascular fractions, amniotic fluids, menstrual bloods, cerebral spinal fluids, milk, bone marrows, and urines.

Aspects and embodiments of the present disclosure also include methods for particle filtration using devices such as one or more of those described above. In some embodiments of the method feed particles are introduced into the first flow chamber of the device via the inlet(s) and a driving force is applied to the particles to propel the particles through the device. The retentate particles are collected from the outlets(s) of the first flow chamber; and the filtrate particles are collected from the outlets of the second and/or third flow chambers. In some embodiments a carrier fluid is introduced into the first flow chamber of the device via at least one inlet.

Flow Exclusion Principles

Figure 2A:
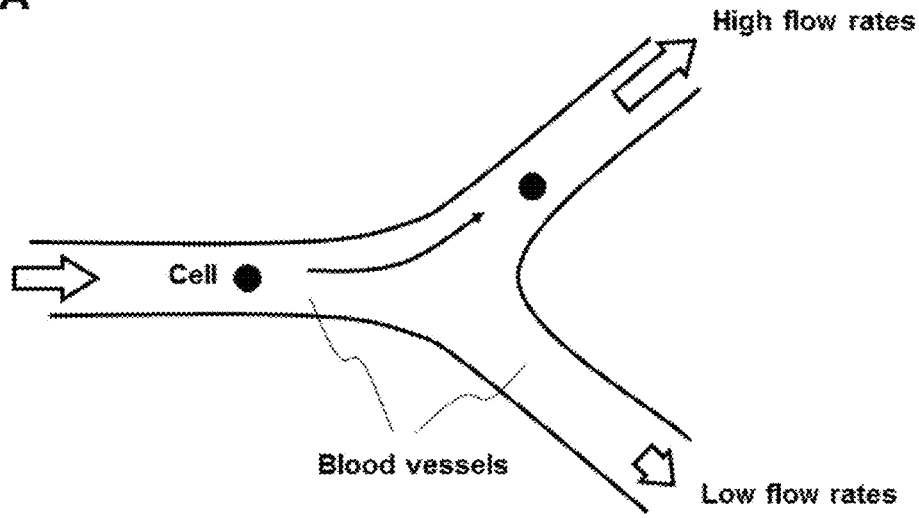
FIGS. 2A and 2B are schematic diagrams.

Filtration can occur using flow bifurcation instead of size exclusion. Specifically, small particles may be retained by a large filter pore under certain flow arrangements. Because small particles are excluded from entering a large pore by the flow, herein this effect is referred to as "flow exclusion." Flow exclusion effect was observed as early as 1921 in microcirculation, i.e. blood flow in minute blood vessels (Krogh, A. "Studies on the Physiology of Capillaries: II. The Reactions to Local Stimuli of the Blood-vessels in the Skin and Web of the Frog" J. Physiol. 55(5-6): 412-422 (1921); Fahraeus, R. "The Suspension Stability of the Blood" Physiological Reviews 9: 241-274 (1929). When a small blood vessel branches into two vessels, blood cells may preferentially enter the vessel with higher flow rates, even though there is no physical restriction or size exclusion that prevents the cells from entering the vessel of low flow rates, if flow patterns were changed to favor size exclusion (FIG. 2A). This effect occurs due to complex hydrodynamic interactions and forces between the cells, the vessels, and the blood flow. Flow exclusion is the most pronounced when the flow rates in the two branches differ significantly. Further, nucleated cells seemed to experience flow exclusion more significantly than enucleated cells, e.g. red blood cells and platelets.

There have been different theories developed in attempt to explain flow exclusion observed in microcapillaries (Krogh, A. "Studies on the Physiology of Capillaries: II. The Reactions to Local Stimuli of the Blood-vessels in the Skin and Web of the Frog" J Physiol 55(5-6): 412-422 (1921); Fahraeus, R. "The Suspension Stability of the Blood" Physiological Reviews 9: 241-274 (1929); Svanes, K. et al. "Variations in Small Blood Vessel Hematocrits Produced in Hypothermic Rats by Micro-Occlusion" Microvasc Res. 1: 210-220 (1968); Yen, R. T. et al. "Model Experiments on Apparent Blood Velocity and Hematocrit in Pulmonary Alveoli" J. Appl. Physiol. 35: 510-517 (1973); Mayrovitz, H. N. et al. "Leukocyte distribution to arteriolar branches: dependence on microvascular blood flow" Microvasc Res. 29(3): 282-294 (1985).

Insights may be gained if we consider the Navier-Stokes equation, which governs the hydrodynamic behavior of incompressible Newtonian fluids:

$$\rho\left(\frac{\partial v}{\partial t} + v \cdot \nabla v\right) = -\nabla p + \mu \nabla^2 v + f.$$

Figure 2B:
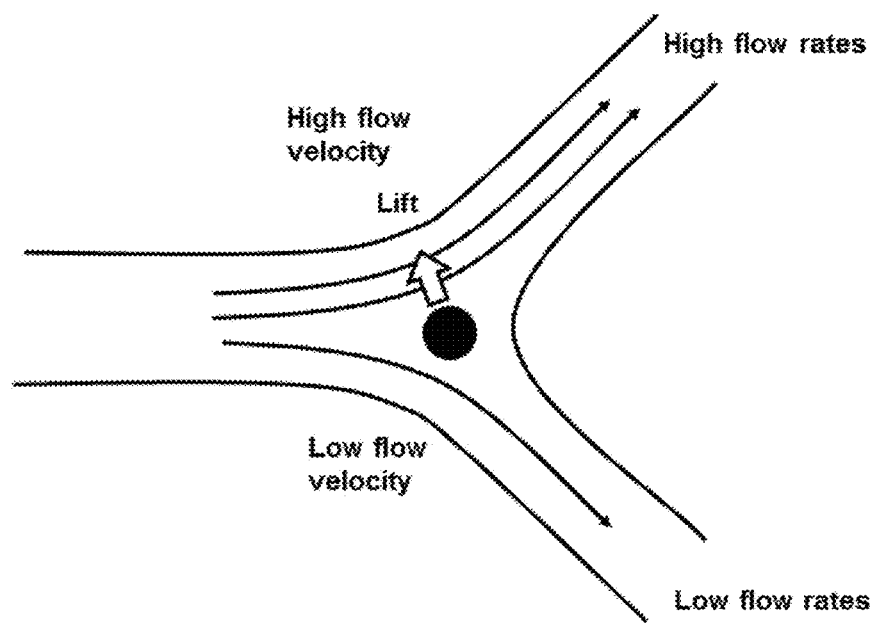

Here $\rho$ is the density of the fluid, v is the velocity of the fluid, p is the pressure, $\mu$ is the viscosity and f is the external body forces, such as gravity. Consider a single cell moving in a branching vessel as shown in FIG. 2A. To analyze the cell's migration path, the exact fluid flow distribution and forces on the cell have to be calculated. This is often a daunting task that requires intensive computer calculation, even for a single cell. The problem becomes much more difficult when many cells are interacting with each other, as in the case of blood flow in circulation. Perhaps the easiest way to gain insight to how flow exclusion occurs is to apply Bernoulli's principle, which states that an increase in the speed of the fluid occurs simultaneously with a decrease in pressure. Because of the flow rate difference between the two branching vessels, a cell experiences a lift force towards the vessel with higher flow speeds (FIG. 2B). This lift force prevents or discourages the cell from entering the vessel of lower flow rate, even though the vessel may be physically large enough to allow passage of the cell. Therefore, flow exclusion occurs. Obviously, the above theory may be an oversimplification for the following reasons: (a) fluids involved, such as blood and bone marrow may not be Newtonian; (b) particle concentrations are so high that particle-particle interaction may be a main factor dominating the motion of the particles; (c) particles involved are deformable and flexible in response to the hydrodynamic forces.

Figure 3A:
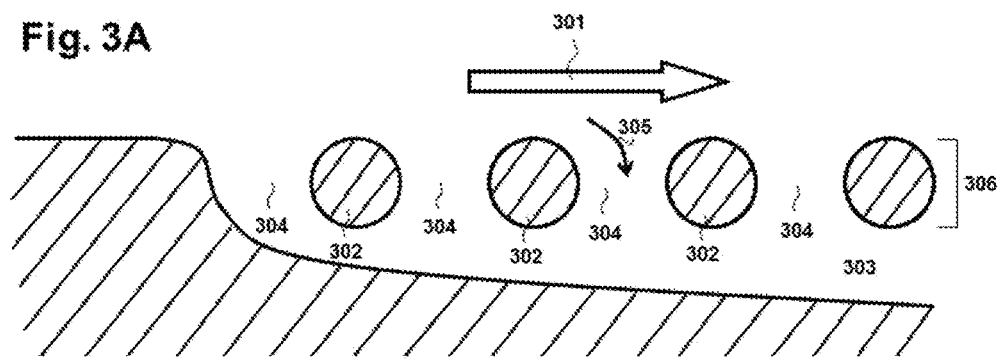
FIGS. 3A-3C are schematic diagrams that illustrate flow exclusion principles in an embodiment of the present disclosure.

Without being held to a particular mechanism or theory, aspects and embodiments of the present disclosure can be understood according to tangential flow filtration and flow exclusion principles. In one embodiment of the present disclosure, a filter comprising large pores is used to retain relatively small particles, in contrast to conventional tangential flow filtration, where small pores are used to retain large particles by size exclusion. A significant advantage of some embodiments the present disclosure is the significant reduction or elimination of particle damage and filter clogging, allowing processing of deformable and/or fragile particles at high throughputs. As shown in FIG. 3, embodiments of the present disclosure may use a tangential flow 301, a filter 306 comprising an arrangement of pillars 302 and pores 304, and a flow chamber 303 (FIG. 3A). In some embodiments the flow chamber 303 may gradually widen along the direction of fluid flow so that under operating conditions, only a small fraction of the tangential flow 301 is drawn through the pores 304. The rate at which the flow chamber 303 widens together with the filter geometry determines the amount of flow drawn through each pore 304. The more gradual the chamber 303 expands, the less flow it will draw through the pores.

Figure 3B:
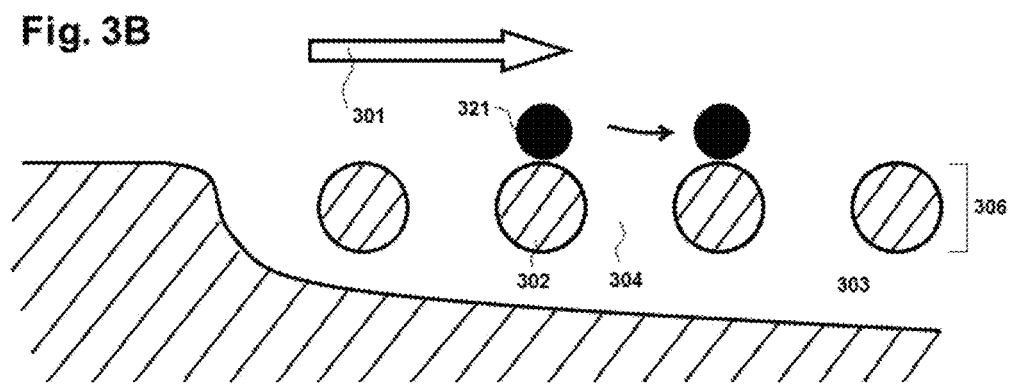
Figure 3C:
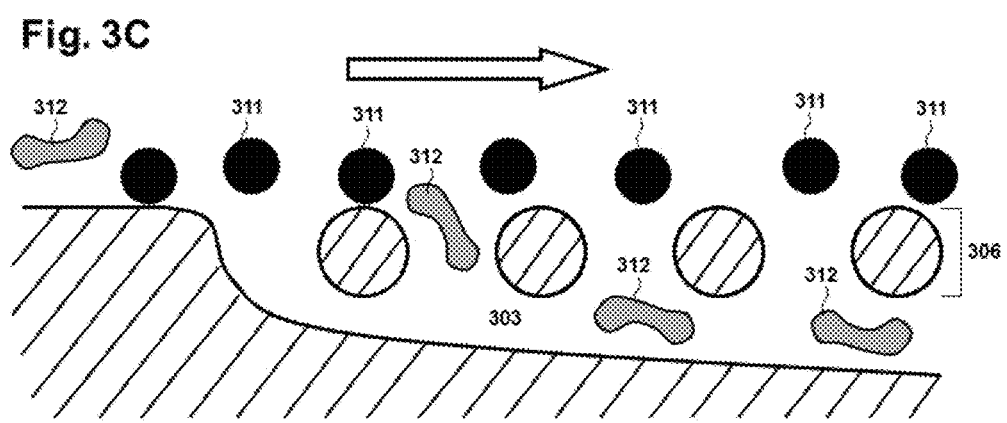

Under laminar flow conditions (FIG. 3A), the tangential flow 301 bifurcates around each pillar 302, much as blood flow bifurcates around branching blood vessels in microcirculation. If the branching flow 305 entering a pore 304 has a much smaller flow rate than the tangential flow 301 does, then flow exclusion effect may occur. A particle 321 that flows by the pillar 302 may or may not enter the pore 304, depending on the strength of flow exclusion on the particle (FIG. 3B). Because different cell types experience different flow exclusion effects, and because flow exclusion is a function of the flow rate through a pore, one can create flow exclusion conditions that are useful for separating certain cell types by controlling the flow rates at the pores 304. For example, one can design a gradually widening flow chamber 303 to create bifurcating flow conditions that cause strong flow exclusion on lymphocytes 311 and weak flow exclusion on red blood cells 312 (FIG. 3C). As a result the lymphocytes 311 are retained by the filter 306 and the red blood cells 312 pass through the filter 306. Flow exclusion is used as the basis for particle filtration in some aspects and embodiments the present disclosure.

Figure 4:
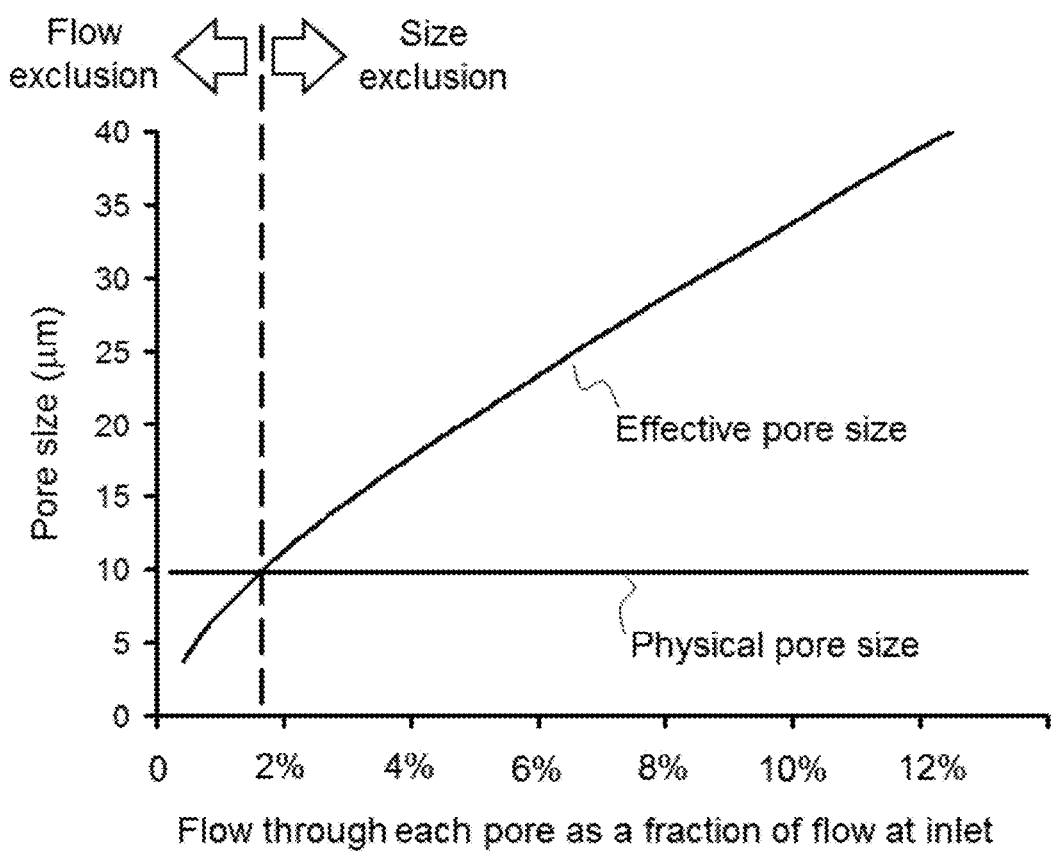
FIG. 4 is a graph showing effective pore size as a function of flow through a pore. Effective pore size was calculated by computer fluid dynamics simulation.

In some aspects and embodiments of the present disclosure, the volumetric flow rate through a pore is much smaller than that of the tangential flow. Using computer fluid dynamics calculation of a single rigid spherical particle in a laminar flow of low Reynolds number conditions, the effective pore size can be estimated as a function of the amount of flow drawn through a pore for a particular design. FIG. 4 shows the results of such calculation for an embodiment shown in FIG. 5A, assuming a flow chamber depth of 30 µm, an feed inlet width of 110 µm, a pillar diameter of 30 µm, and a 40 µm center-to-center distance between adjacent pillars, resulting in a physical pore size of about 10 µm. When the flow rate through each pore is about 0.4% of the tangential flow rate at the feed inlet 502, the effective pore size of a pore is approximately 3.8 µm, which is significantly smaller than the physical pore size of 10 µm. Notice however, that when the volumetric flow rate through each pore is about 1.6% of the tangential volumetric flow rate at the inlet, the effective pore size becomes about the same as the physical pore size. When the flow rate through each pore is larger than 1.6% of the tangential flow rate at the inlet, size exclusion becomes the main basis for particle separation, and the device becomes a conventional filtration device. In contrast to conventional tangential flow filtration, which employs a transmembrane pressure to achieve size exclusion based separation, the present disclosure employs a flow rate distribution around the pores to achieve flow exclusion based separation.

Although the above mentioned computer calculation gives us insights to flow exclusion under idealized and over-simplified conditions (a single, rigid, spherical particle in Newtonian fluid with no Brownian motion), the filtration process of the feed particles in the present disclosure may be substantially stochastic, described by probability, and may not be deterministic.

Particle-particle interactions, particle deformations, and Brownian motion, among other factors, may change the flow pattern and forces exerted on particles, causing flow exclusion to be stochastic. This stochastic nature of flow exclusion may be prominent and very substantial especially when the feed particles comprise complicated particles and fluids, e.g. blood, umbilical cord blood, bone marrow, stromal vascular fraction, etc. To appreciate the complexity of such real world samples, let's consider umbilical cord blood. A typical umbilical cord blood sample contains about 4 billion red blood cells, 10 million white blood cells, and 200 million platelets per milliliter. These cells constitute about 40% of the blood volume, and deform as they interact with each other. Further, the cells settle at different rates under gravity. Without diluting the sample significantly, e.g., by a factor of 1,000, 10,000, 100,000 or more, particle-particle interactions may make blood cells move stochastically, and it may be substantially impossible to predetermine whether a particular cell would be retained using an embodiment of the present disclosure.

Physical Pore Size and Effective Pore Size

One technique for characterizing a filter and its pore size is the measurement of particle retention using rigid spheres (Zeman, L. J. et al. "Microfiltration and Ultrafiltration" Marcel Dekker, Inc., ISBN 0-8247-9735-3, p. 265-274 (1996)). Examples of particle retention measurements disclosed in this publication are herein incorporated by reference. Examples of particles which may be used for such measurements include latex beads and polymer microspheres. The "physical pore size", the "effective pore size", and the "retention size" can be measured and characterized using such techniques, as described above. Using rigid spheres as a standard, different filters and devices can be characterized and compared, regardless of their intended use. For example, a conventional filtration device for removing bacteria in water can be compared with a blood filtration device, even though bacteria may have very different sizes, shapes, deformability, charge, concentration, and other characteristics from blood cells.

In conventional size exclusion filtration, the effective pore size of a pore is larger than or substantially equal to the physical pore size, and the retention size of a filter is also larger than or substantially equal to the physical pore size. In contrast, in some aspects and embodiments of the present disclosure, the effective pore size of a pore is smaller or substantially smaller than the physical pore size of the pore, using flow exclusion (FIG. 4).

While devices can be characterized and compared using standard rigid spheres, actual embodiments of the present disclosure for biological samples may be empirically optimized for each particular application. A particle that is substantially larger than the effective pore size of a pore may still go through the filter due to particle deformation or the stochastic nature of the process. This phenomenon is herein called "leakage." In a conventional filter, where the effective pore size is larger than or substantially equal to the physical pore size, particles tend to clog and foul the filter when leakage occurs. When deformable and fragile particles leak through a conventional filter, the particles may suffer large shear and get damaged or lysed, triggering a cascade of filter fouling in addition to clogging. This is a serious problem for applications using biological samples and cells.

Some aspects and embodiments of the present disclosure comprise methods and devices that employ pores substantially larger than the effective pore size, thereby significantly reducing or avoiding filter fouling and clogging. In addition, embodiments of the present disclosure employ low volumetric flow rates through their pores as a means to create flow exclusion. The combination of large pores and small flow rate facilitates low shear in and around the pores, thereby further reducing fouling, clogging, particle activation, and particle damage problems.

Filtration Modules, Units, and Devices

Filter Module

Another embodiment of the present disclosure is a filter module, shown in FIG. 5. A first flow chamber 501 has an inlet 502 and an outlet 503. Feed particles, i.e. particles to be processed by filtration, enter the inlet 502 and are driven through the first flow chamber 501 from the inlet towards the outlet, using a driving force. The first flow chamber 501 is separated from and in fluid connection with a second flow chamber 504 by a filter 508, which comprises an arrangement of pillars 505. The spacing between the pillars constitutes the pores 506 of the filter 508. The second flow chamber 504 is arranged to draw small amounts of flows through the pores 506 across the filter 508, to receive the filtrate particles, and to harvest filtrate particles via a filtrate outlet 507. The flow rates through each pore 506 are designed to be a small fraction, e.g. $1/10$, $1/20$, $1/30$, $1/50$, $1/100$, $1/200$, $1/300$, $1/500$, $1/1,000$, $1/2,000$, $1/5,000$, $1/10,000$, $1/20,000$, $1/50,000$, or $1/100,000$, of the flow rates at the inlet 502 of the first flow chamber 501 to facilitate flow exclusion. In some embodiments, the pores 506 are sized such that the physical pore sizes are substantially larger than the effective pore size. Some embodiments of the filter 508 may have from about 10 to about 50,000 pores 506, e.g. 10, 20, 50, 100, 200, 500, 1,000, 2,000, 5,000, 10,000, or 50,000 pores. For the convenience of further discussion, the first flow chamber 501, where feed and retentate particles migrate, is herein referred to as the "retentate chamber," and the second flow chamber 504, where filtrate particles migrate, as the "filtrate chamber."

The particle flow inside various embodiments may be created using a fluid flow, a driving pressure, a vacuum, a head height, gravity, a centrifugal force, a magnetic force, a capillary action, or a combination of the above. The particle flow may also be created using an electric field, an electrophoretic field, a dielectrophoretic field, an electro-osmotic force, an electrokinetic force, or a combination of the above forces. These fields or forces may move the particles and may or may not move the fluids in which the particles are contained. In some instances, these fields or forces may move the particles without moving the fluids in which the particles are contained. For example, in the absence of any electrokinetic flow, an electrophoretic field may drive charged particles through embodiments of a device of the present disclosure without creating a fluid flow. In the case of gravity, particles having densities greater than that of the fluid may settle through the fluid. In other cases, the fluid may flow in the opposite direction as the particles. Clearly, flow exclusion does not occur in these examples. However, the driving forces inside the device can create their own exclusion effects, much as fluid flows do. Therefore, gravity, centrifugal forces, electric fields, electrophoretic fields, and electrokinetic forces may also be used to drive the particles, and achieve filtration effects that do not rely on size exclusion or physical restriction.

Figure 5A:
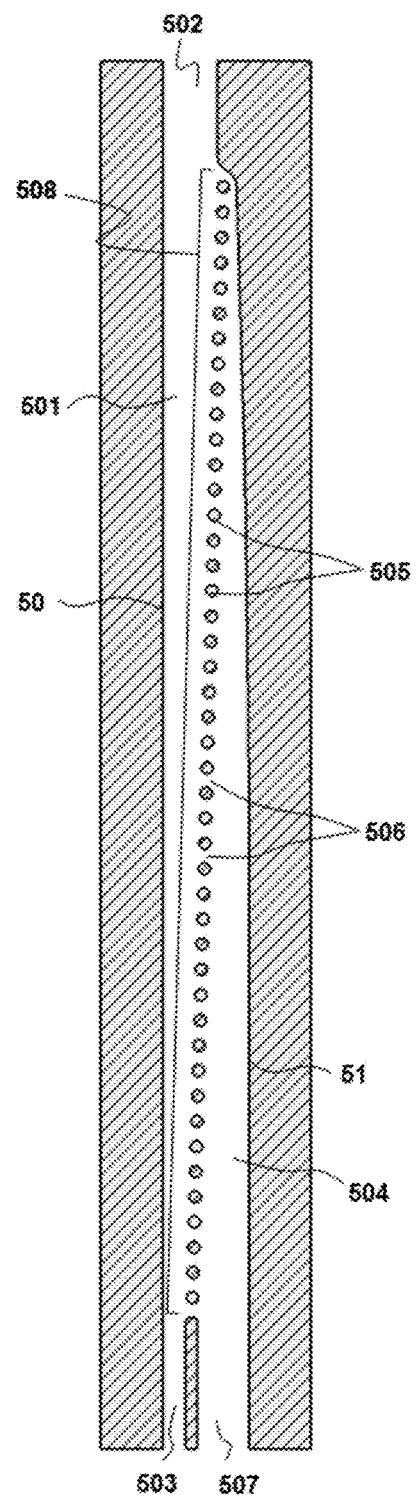
FIGS. 5A-5F are schematic diagrams showing filter module embodiments.
Figure 5B:
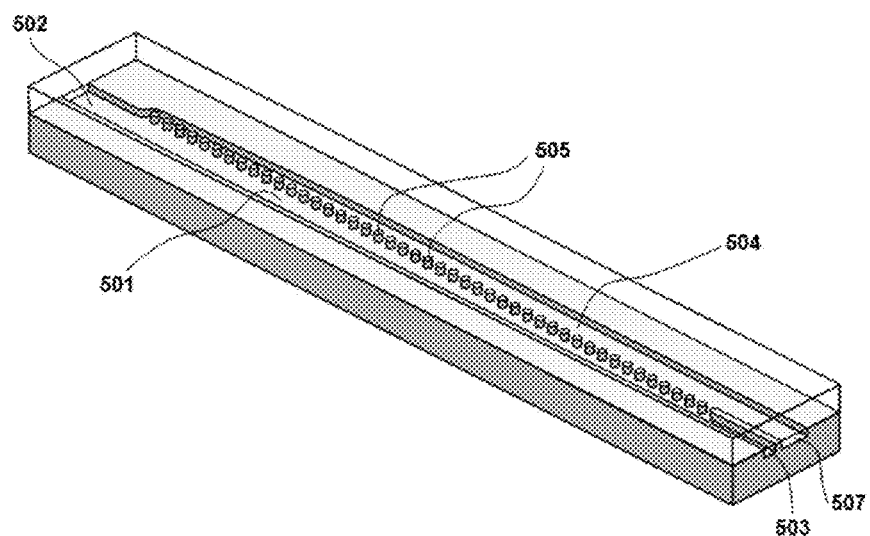
Figure 5C:
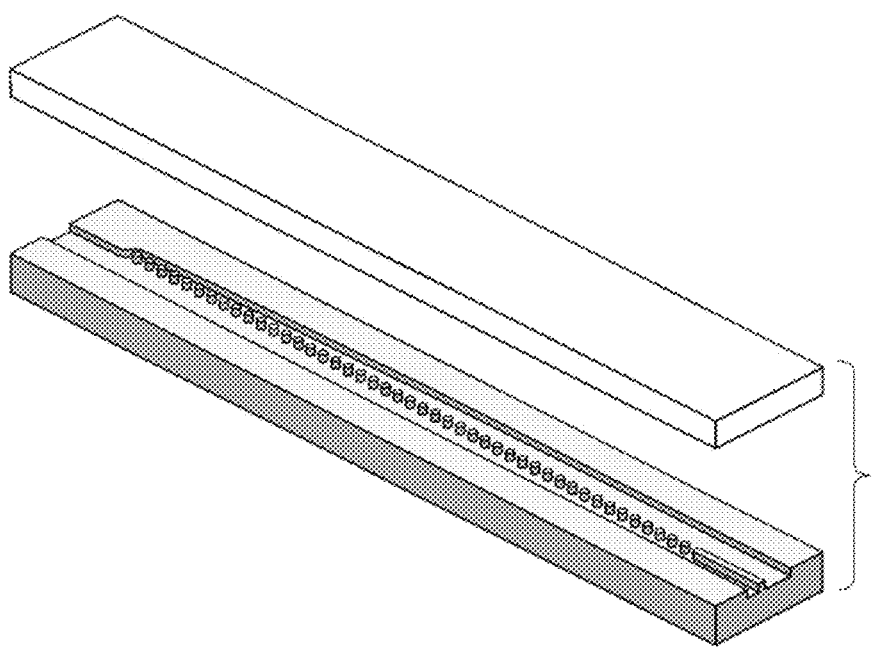
Figure 5D:
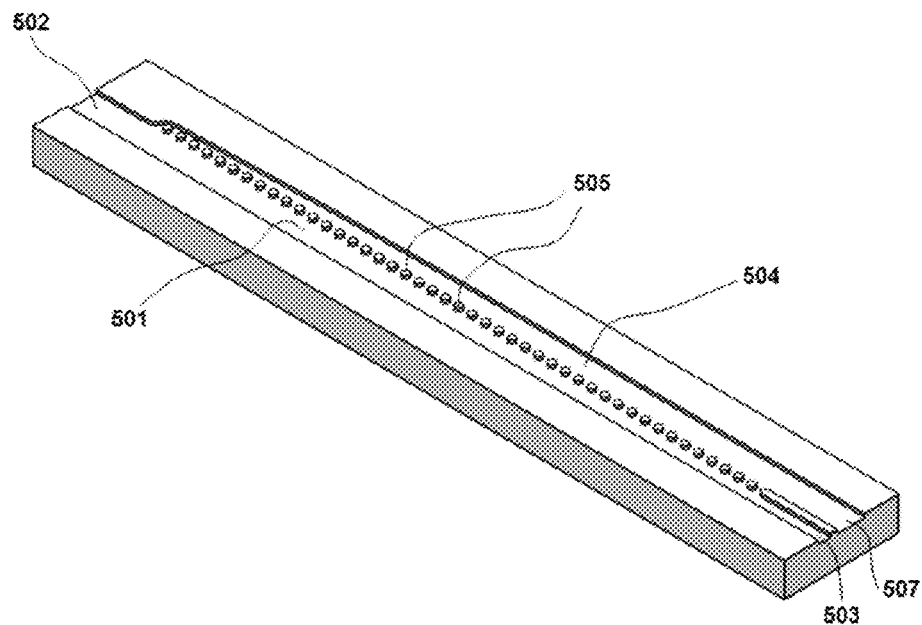
Figure 5E:
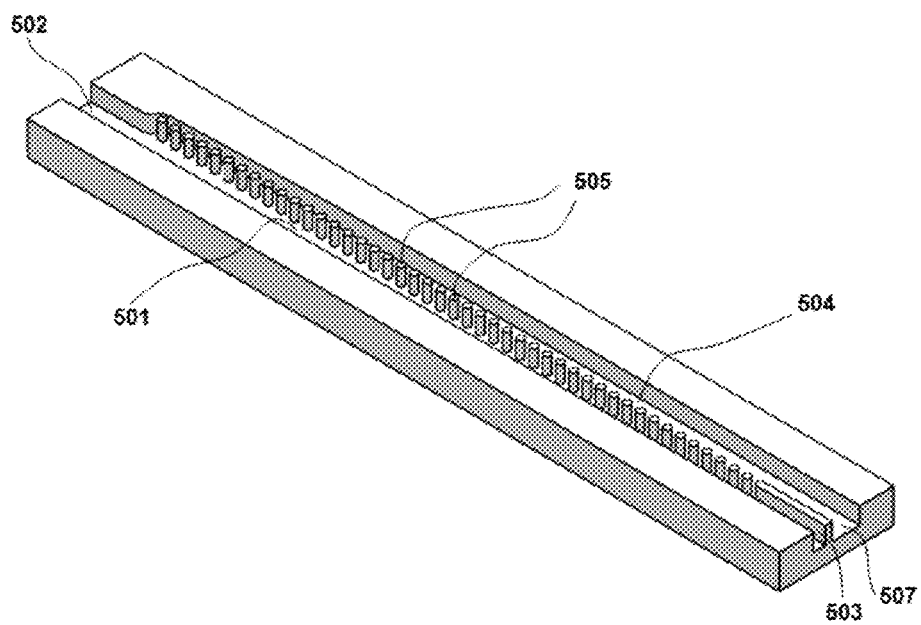
Figure 5F:
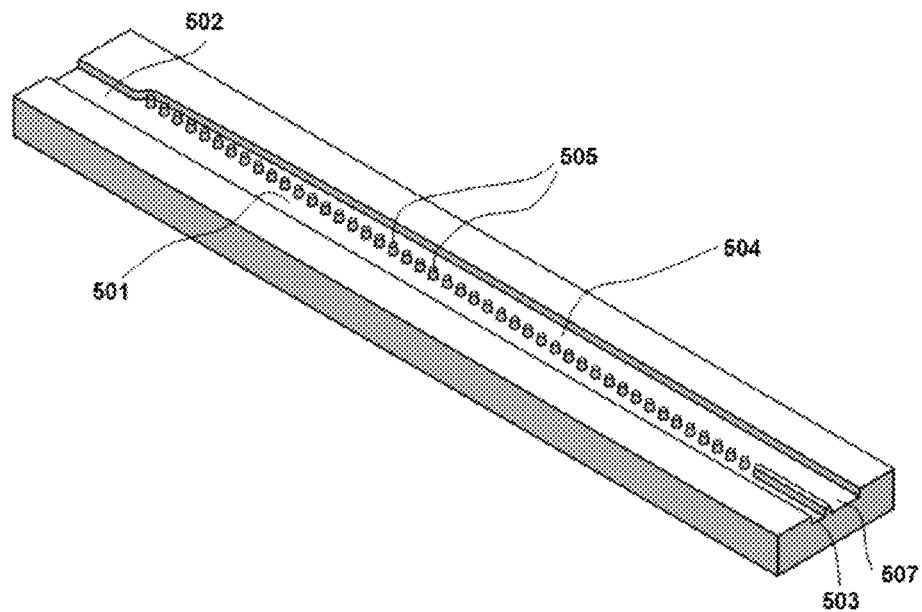

In some embodiments, the pillars 505 may have heights similar to their widths, thereby having an aspect ratio close to 1, e.g. 0.8, 0.9, 1.0, 1.1, 1.2, or 1.3, as shown in FIG. 5B and 5C. Alternatively, the pillars 505 may have heights smaller than their widths, thereby having an aspect ratio substantially smaller than 1, e.g. 0.1, 0.2, 0.3, 0.4, 0.5, or 0.6, as shown in FIG. 5D, or heights greater than their widths, thereby having an aspect ratio substantially greater than 1, e.g. 1.5, 2, 3, 5, 8, 10, 20, 100, 500, 2,000, or 10,000, as shown in FIG. 5E. High aspect ratio pillars designs have the advantage of higher capacities and throughputs, whereas low aspect ratio pillars designs have the advantage of ease of fabrication. The pillars 505 may become gradually narrower or tapered (FIG. 5E). The draft angle could be close to 90 degrees, e.g. 80, 85, 87, 88, or 89 degrees. The tapered pillars may facilitate demolding and may make fabrication using injection molding, embossing, soft lithography, or other replication techniques less difficult.

Figure 6A:
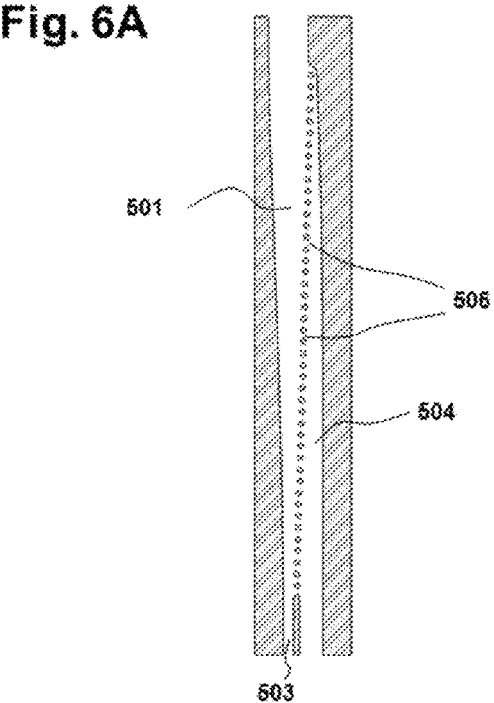
FIGS. 6A and 6B are schematic diagrams that provide top views of two filter module embodiments.
Figure 6B:
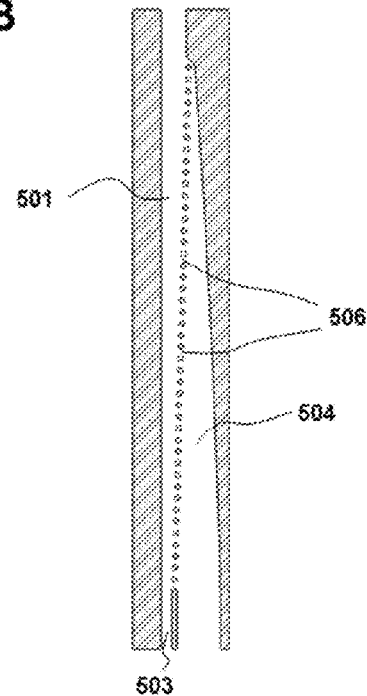
Figure 7A:
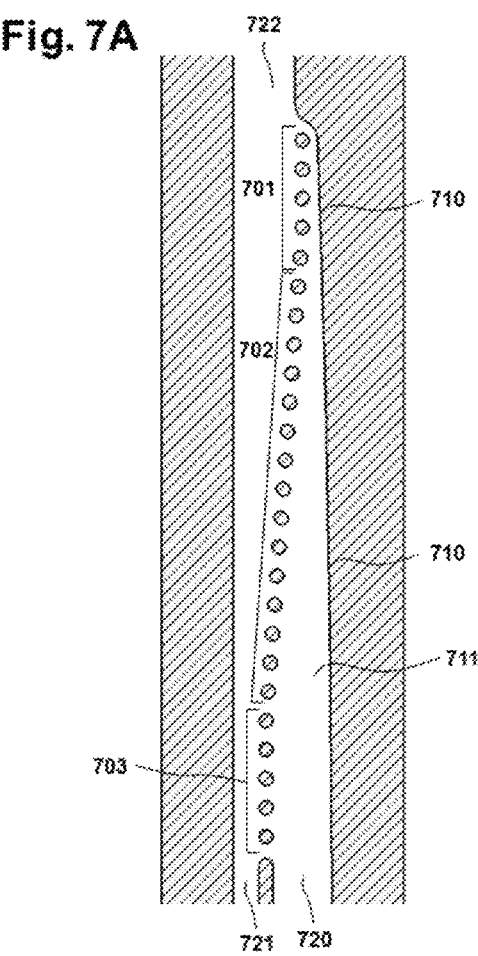
FIGS. 7A-7B are schematic diagrams that illustrate filter module embodiments.
Figure 7B:
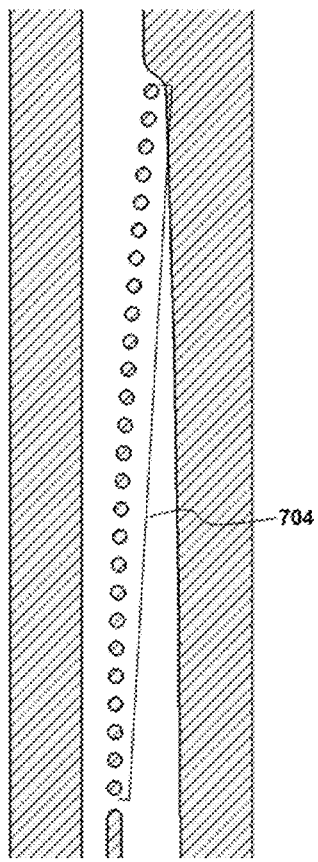
Figure 7C:
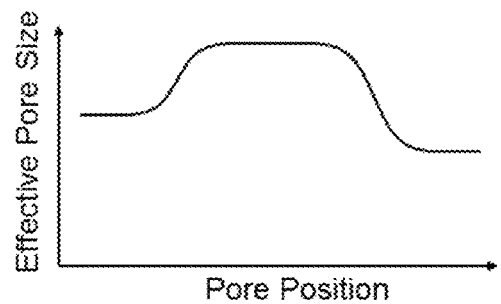
FIG. 7C is a graph that illustrates the effective pore sizes of filter modules shown in FIG. 7A.
Figure 7D:
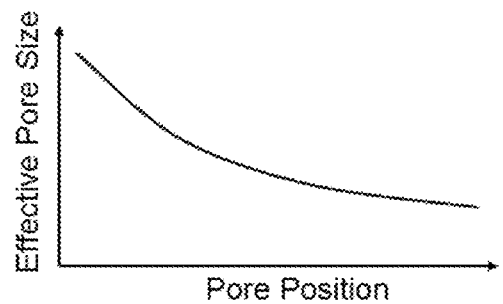
FIG. 7D is a graph that illustrates the effective pore sizes of filter modules shown in FIG. 7B.

In some embodiments, the sidewalls of the retentate chamber 50 and the filtrate chamber 51 are approximately parallel to each other (FIG. 5A). In some embodiments, the retentate chamber 501 may have a substantially constant width, may become gradually wider, or may become gradually narrower (FIG. 6). A change in the width of the retentate chamber 501 may result in a change in the flow rates in the chamber 501 and the resulting shear stress. In the embodiment illustrated in FIG. 6B, because feed liquids are drawn into the filtrate chamber 504, the flow speed in the retentate chamber 501 gradually become smaller as fluids move towards the outlet 503. In contrast, in the embodiment illustrated in FIG. 6A, fluids in the retentate chamber 501 may accelerate towards the outlet 503, as the total cross sectional area of the retentate chamber 501 and the filtrate chamber 504 becomes smaller. The degree to which the filtrate chamber 504 becomes wider may substantially determine the amount of flow drawn through the pores 506, and may be optimized for a desired effective pore size.

In another embodiment of the present disclosure, the retentate chamber may gradually narrow from the inlet side towards the retentate outlet, and the filtrate chamber may gradually widen towards the filtrate outlet. For applications where high flow rate and low shear stress is desired, it may be preferred that the retentate chamber be wide at the inlet side and narrow at the outlet side. Such configuration may keep the flow speed low at the inlet and the shear stress low throughout the retentate chamber. In another embodiment of the present disclosure, the retentate chamber may be configured to gradually narrow from the inlet side towards the retentate outlet and to keep the average flow speed in the retentate chamber substantially constant as fluids flow from the inlet towards the outlet. In another embodiment of the present disclosure, the retentate chamber and the filtrate chamber may be configured such that the average flow speed in the retentate chamber substantially constant as fluids flow from the inlet towards the outlet.

In another embodiment of the present disclosure, the filter comprises pillars arranged on a curve (FIG. 7). The "curving" of the filter may result in a specific filter characteristic. That is, each pore may have a different effective pore size designed to achieve certain filtration requirements. In the embodiment illustrated in FIG. 7A, the filter 701 initially forms a small angle with the sidewall 710 of the filtrate chamber 711, allowing the filtrate chamber to draw a very small amount of flow across the filter 701. The angle between the filter 702 and the sidewall 710 then becomes larger to increase the amount of flow drawn through the pores, resulting in larger effective pore sizes. The angle between the filter 703 and the sidewall 710 may become smaller towards the filtrate outlet 720, reducing the amount of flow drawn through the pores. In FIG. 7B, the filter 704 comprises pillars arranged on a curve designed to maintain a certain filter characteristics. Each pore's effective pore size as a function of its position from the inlet 722 side to the outlet 721 side is illustrated qualitatively in FIG. 7C and FIG. 7D for the embodiments shown in FIGS. 7A and 7B, respectively. It is understood that other pillar arrangements may also be used, depending on the desired filter characteristics for the particular application under consideration.

In yet another embodiment, the flow rates through each pore are essentially identical. In yet another embodiment, the flow rates drawn through each pore are smaller than or equal to a maximum fraction x of the flow rates of the tangential flow, where x ranges from about 1/5 to about 1/100,000. For example, a desirable x may be 1/5, 1/10, 1/20, 1/50, 1/100, 1/200, 1/500, 1/1,000, 1/2,000, 1/5,000, 1/10,000, 1/20,000, 1/50,000, or 1/100,000. An example of this embodiment is shown in FIG. 5. The filter comprises between about 10 and about 100,000 pillars, e.g. about 10, 20, 50, 100, 200, 500, 1000, 2,000, 5,000, 10,000, 30,000, or 100,000 pillars. The pillars and the filtrate chamber are configured in a way that the effective pore size is substantially smaller than the physical pore size.

Figure 8:
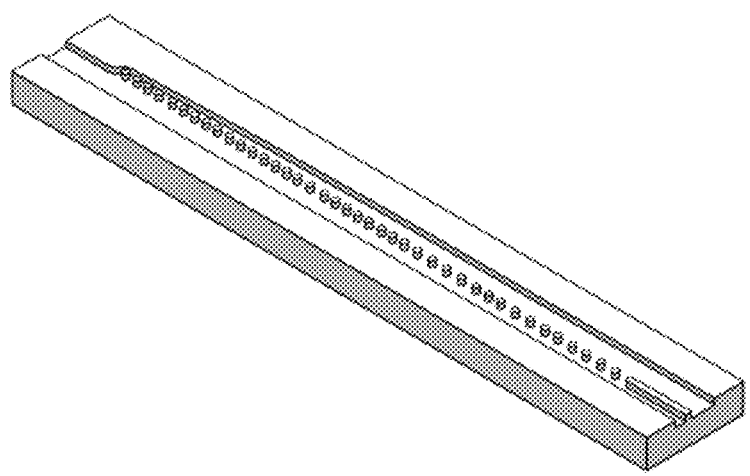
FIG. 8 is a schematic diagram that provides a three dimensional view of a filter module embodiment with different pore sizes. The lid of the module is not shown.
Figure 9A:
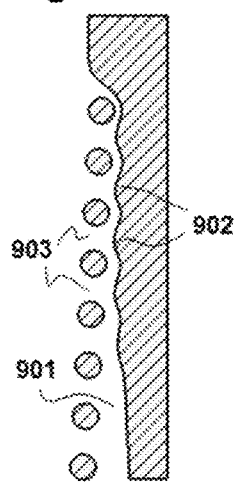
FIGS. 9A-9H are schematic diagrams that provide top views of portions of filter module embodiments.
Figure 9B:
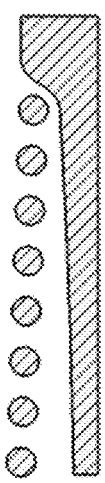
Figure 9C:
Figure 9D:
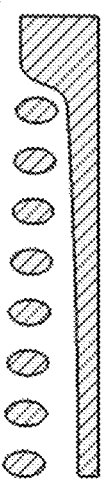
Figure 9E:
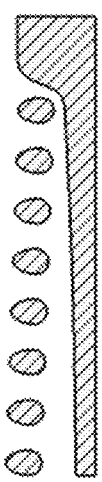
Figure 9F:
Figure 9G:
Figure 9H:
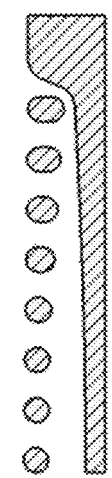

In yet another embodiment of the present disclosure, the filter comprises an arrangement of pillars which are equally spaced, as shown in FIG. 5, FIG. 6, and FIG. 7. In yet another embodiment of the present disclosure the pillars are unevenly spaced, as shown in FIG. 8. For some applications, it may be advantageous to vary the physical pore sizes so that certain particles are allowed to pass through physically large pores. The pillars may have different cross sectional shapes. Examples of desirable cross-sectional shapes include, but are not limited to, those shown in FIG. 9, e.g. round (FIGS. 9A and 9B), oval shaped (FIG. 9C), elliptical (FIG. 9D), egg shaped (FIGS. 9E and 9F), airfoil shaped (FIG. 9G), etc. A filter may also comprise pillars of different shapes and/or sizes (FIG. 9H). For gentle separation of fragile particles, it may be preferred that the pillars have no sharp edges that may be in contact with the particles. Sharp edges may cut open, split, or lyse fragile particles. While non-sharp pillar surfaces may be preferred in many applications requiring gentle filtration, it is also possible to use rectangular, square, or polygonal pillar cross sections, for example, in cases where particle damage is not of concern.

In another embodiment of the present disclosure, the filtrate chamber 901 has a wavy sidewall 902, comprising alternating convex and concave parts (FIG. 9A), and the period of the wavy sidewall coincides with the center-to-center distance of the pores 903. The wavy sidewalls may help stabilize the flow and maintain small effective pore sizes.

It is understood that in embodiments of the present disclosure, the filter may comprise pillars of different shapes and sizes, arranged evenly or unevenly on a straight line or a curve, in order to achieve certain filter characteristics.

Figure 10A:
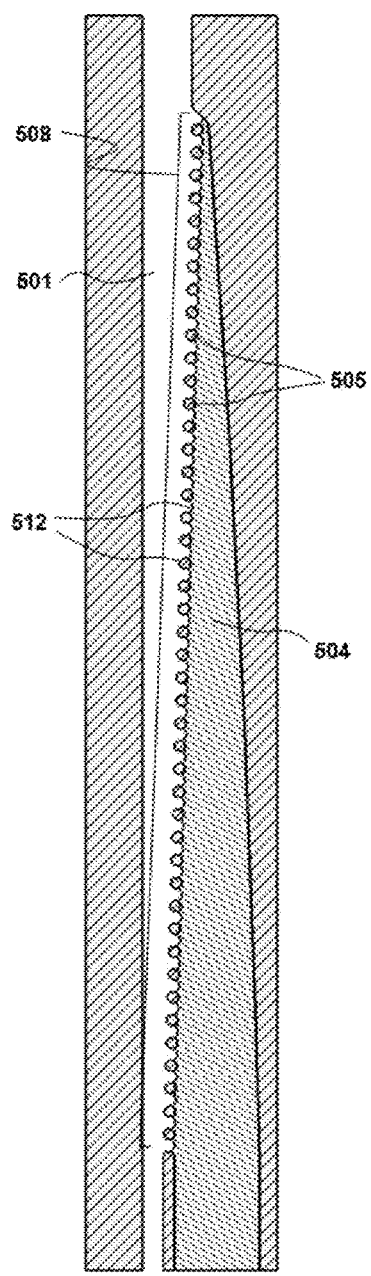
FIGS. 10A-10C are schematic diagrams showing a filter module having a filtrate chamber shallower than its retentate chamber.
Figure 10B:
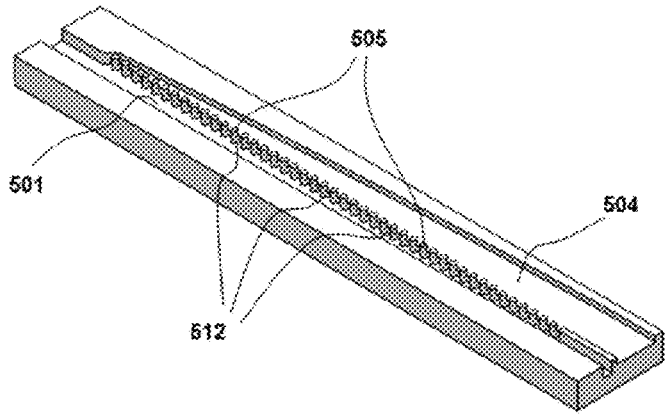

In another embodiment of the present disclosure, the filtrate chamber 504 is shallower than the retentate chamber 501 (FIG. 10). In this embodiment, the filter 508 comprises a contiguous surface 512 and pillars 505. The filtrate chamber

Figure 10C:
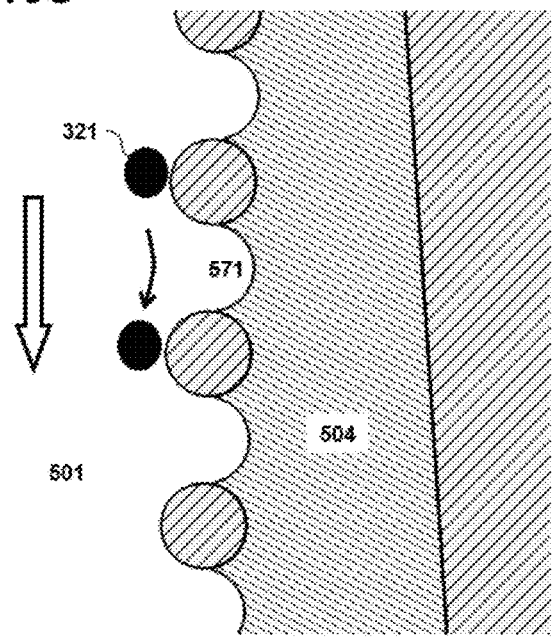

504 may be shallower than some large retentate particles 321 (FIG. 10C). However, because the retentate particles 321 are flow excluded from the physical pores, they substantially never enter the shallow filtration chamber 504, or the narrow parts 571 of the pores (FIG. 10C). Consequently, the detrimental effects associated with size exclusion filtration may rarely occur in this embodiment. This design reduces the aspect ratios of pillars 505 without reducing the filter area or depth, and may make the device fabrication easy and robust.

Figure 11A:
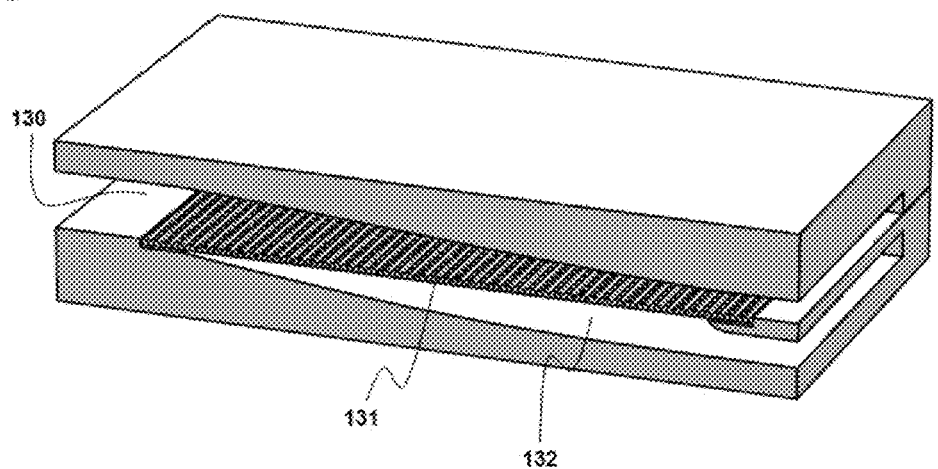
FIGS. 11A and 11B are two schematic diagrams showing a three dimensional assembled view and a three dimensional exploded view of a filter module comprising a screen filter.
Figure 11B:
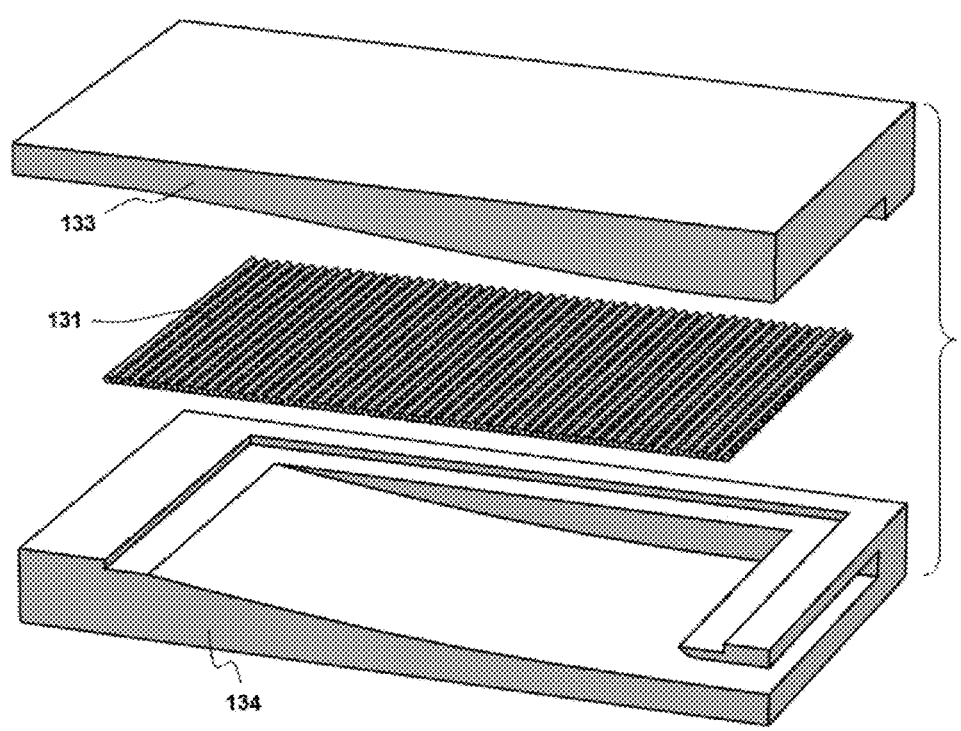
Figure 11C:
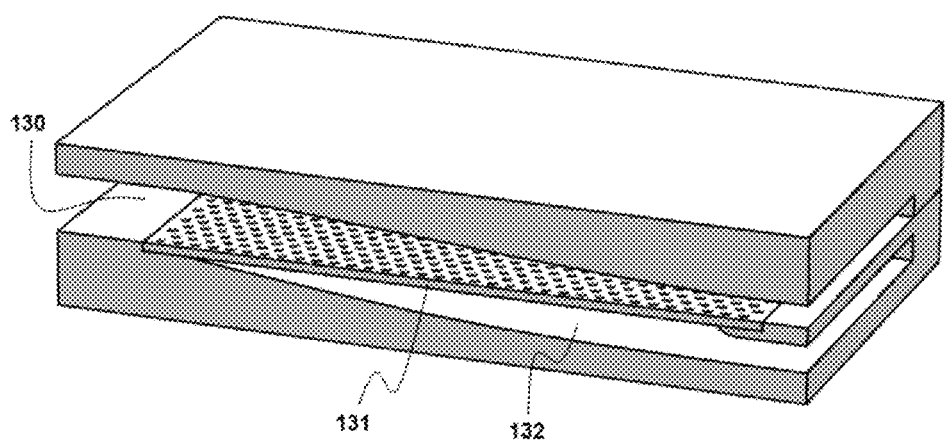
FIGS. 11C and 11D are two schematic diagrams showing a three dimensional assembled view and a three dimensional exploded view of a filter module comprising a porous membrane filter.
Figure 11D:
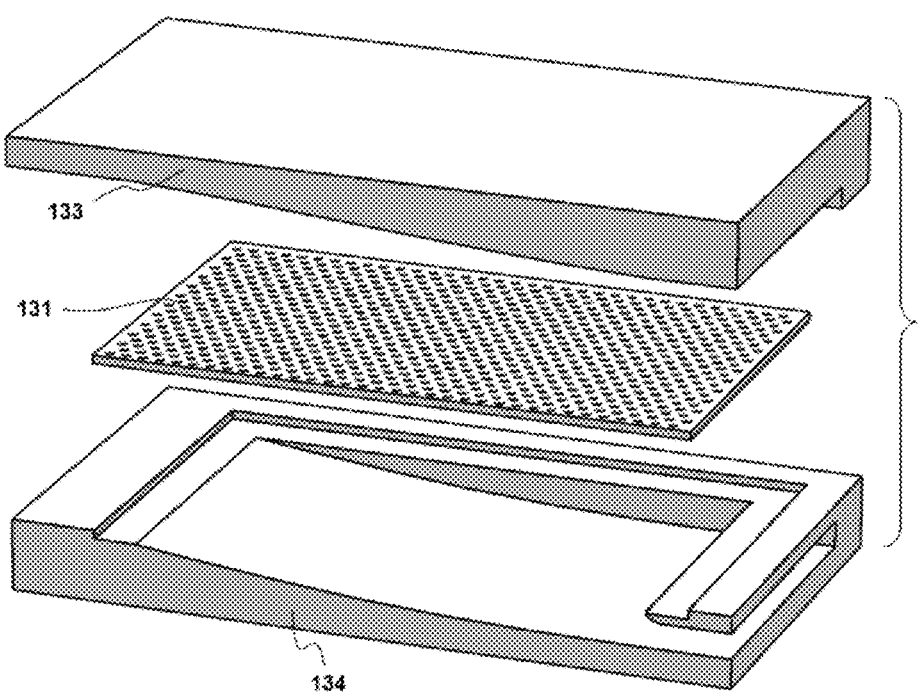

In yet another embodiment of the present disclosure, a filter module comprises a retentate chamber 130, a filter 131 comprising a screen filter, and a filtrate chamber 132 that controls the flows going across the screen filter 131 (FIGS. 11A and 11B). The flow chambers 130, 132 comprise layers 133, 134 comprising recesses. The filtrate chamber 132 comprises a gradually deepening recess in layer 134, arranged to draw small amounts of flow through the filter 131. The filter 131 is sandwiched between the retentate chamber layer 133 and the filtrate chamber layer 134. This embodiment allows for a large filter area, and can achieve very high capacity and throughput. A variation to this embodiment comprises a porous filter layer 131 sandwiched between a retentate chamber layer 133 and a filtrate chamber layer 134 (FIGS. 11C and 11D). The porous filter layer may comprise, for example, a track etched membrane, or a laser machined metal sheet, etc. The layers may be glued, bonded, or simply pressed together (FIGS. 11C and 11D). The pores on the filter 131 may be regularly spaced, as shown in FIGS. 11A-11D, or may be randomly distributed, as with radiation track etched membrane filters.

The above described embodiments of the present disclosure may be useful as devices for concentrating particles, or for removing a retentate particle population from a filtrate particle population. However, in some instances, it may be desirable to deplete the filtrate population from the retentate population, or isolate the retentate particles in a different fluid.

Figure 13:
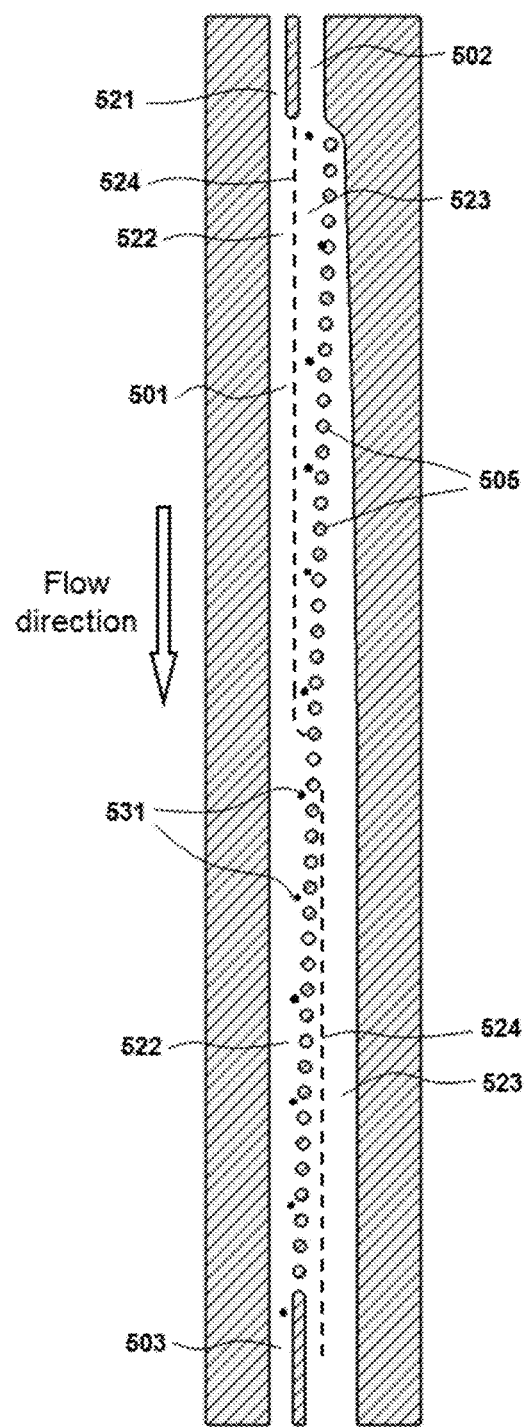
FIG. 13 is a schematic diagram showing a top view of a filter module employing a carrier flow.

For example, in some instances, it may be desirable to isolate nucleated blood cells from whole blood, and remove as many enucleated red blood cells as possible. A carrier fluid 522 may be introduced to the retentate chamber 501 (FIG. 13). In one embodiment the retentate flow chamber 501 comprises at least one carrier flow inlet 521 in addition to at least one feed inlet 502. Here, a carrier fluid 522 may be injected into the retentate chamber 501 and form a laminar flow stream 522 alongside the feed flow stream 523. The laminar flow conditions may cause the carrier flow 522 and the feed flow 523 to move side by side without convective mixing. The interface between the two streams 522, 523 is shown as the dashed line 524 in FIG. 13. Retentate particles 531 may be retained by the filter comprising pillars 505 and moved from the feed stream 523 into the carrier stream 522. At the retentate outlet 503, retentate particles 531 are in the carrier flow 522, thereby substantially rid of the filtrate population. Depending on the desired purity requirement, the carrier fluid flow rates may be smaller than, equal to, or greater than the retentate fluid flow rates. It is understood that a carrier flow may be applied in a similar manner to any of the embodiments of the present disclosure, and is not limited to any particular embodiment. The carrier flow may also be introduced to wash, treat or label the retentate particles. In some embodiments, more than one carrier flows may be introduced to treat the retentate particles. For example, one can use some embodiments of the present disclosure to label and wash cells in a continuous flow fashion. A solution containing antibody labels or stains against specific retentate cells may be introduced alongside the feed flow as the first carrier flow, and a wash solution may be introduced next to the first carrier flow as the second carrier flow. Due to flow exclusion, retentate cells may migrate from the feed flow into the first carrier flow, where the cells are stained or labeled, and then may migrate from the first carrier flow into the second carrier flow, where the cells are washed. More than one inlet may be used at a retentate chamber to introduce carrier flows for any of the embodiments of the present disclosure.

Dual Filter Module

In some embodiments, two substantially identical filter modules may be combined to form a "dual filter module." In one embodiment, two filter modules may form mirror images with respect to each other and share one retentate chamber to form a "dual filter module" (FIG. 14A). The retentate chamber 501 may have at least one inlet 502 and one outlet 503. Feed particles may enter the inlet 502 and may be driven through the flow chamber 501 towards the outlet 503, using, for example, a fluid flow, a pressure drop, a hydrodynamic pressure, a pressure source, a vacuum, a head height, gravity, a centrifugal force, an electric field, an electrophoretic field, an electrokinetic force, an elctro-osmotic force, a capillary action or a combination of the above. The retentate flow chamber 501 may be separated from each of the two filtrate flow chambers 504 by a filter 508, and may be arranged symmetrically with respect to the centerline 514. Embodiments of the filter 508 may comprise an arrangement of from about 10 to about 100,000 pillars 505, e.g. 10, 20, 50, 100, 200, 500, 1,000, 2,000, 5,000, 10,000, 20,000, or 100,000 pillars. The openings between the pillars may constitute pores 506 of the filter 508. The filtrate flow chambers 504 may be designed to draw a small amount of flow through each pore 506, and remove filtrate particles via filtrate outlets 507. The flow rate through each pore 506 may be designed to be a small fraction, e.g. $1/10$, $1/20$, $1/30$, $1/50$, $1/100$, $1/200$, $1/300$, $1/500$, $1/1,000$, $1/2,000$, $1/5,000$, $1/10,000$, $1/20,000$, $1/50,000$, or $1/100,000$, of the flow rates at the retentate flow chamber 501 to facilitate flow exclusion.

In any of the dual filter module embodiments, the retentate chamber may further comprise a carrier flow inlet 521 (FIG. 14B). A carrier flow 522 may be introduced in between the two feed flows 523, so that the retentate particles are harvested in the carrier flow 522 at the retentate outlet 503. This embodiment may be capable of yielding high purity retentate particles.

Figure 15A:
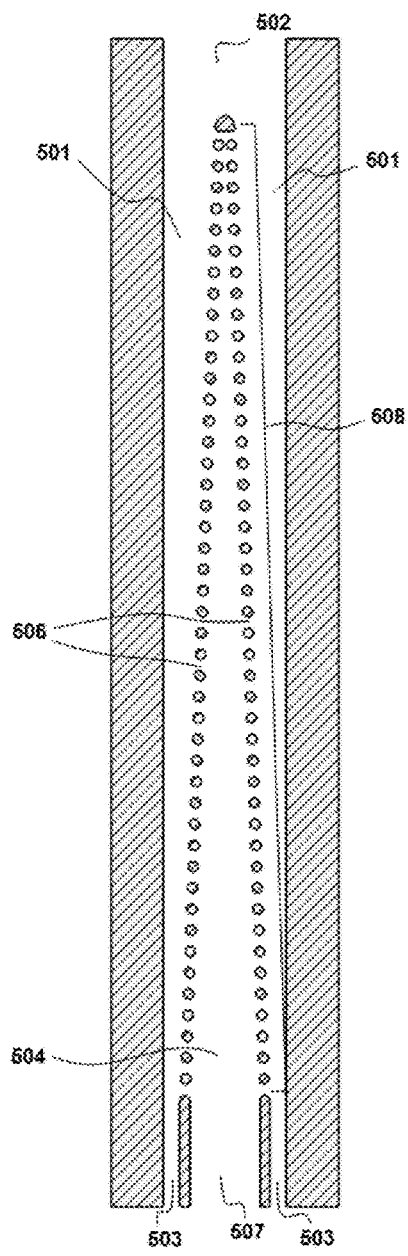
FIGS. 15A and 15B show top views of two dual filter modules.
Figure 15B:
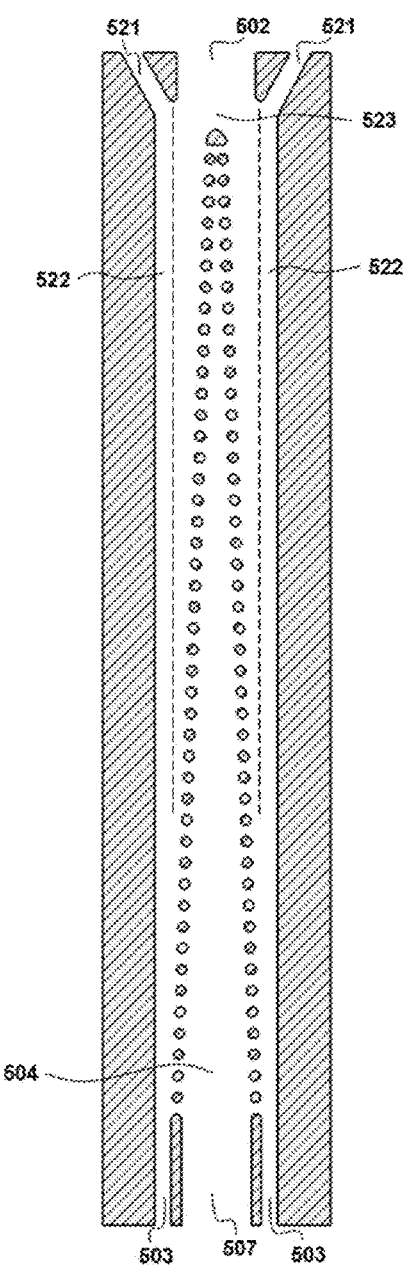

Another embodiment of the dual filter module is shown in FIG. 15, where two filter modules form mirror images and share one filtrate chamber. The filtrate chamber 504 comprising a filtrate outlet 507 may be placed between two retentate chambers 501. The filtrate chamber 504 may draw a small amount of flow through each pore 506 at filters 508 to facilitate flow exclusion. Feed flow may enter the retentate chamber 501 via an inlet 502. Retentate particles may be harvested at retentate outlets 503; filtrate particles may be harvested at the filtrate outlet 507. This embodiment may further comprise at least one carrier flow inlet 521 (FIG. 15B). Carrier flow streams 522 may be established alongside the feed flow stream 523, so that retentate particles are harvested in the carrier flow streams 522. Again, the carrier flow increases the purity of the retentate particles.

Multiple Filter Module

Figure 16A:
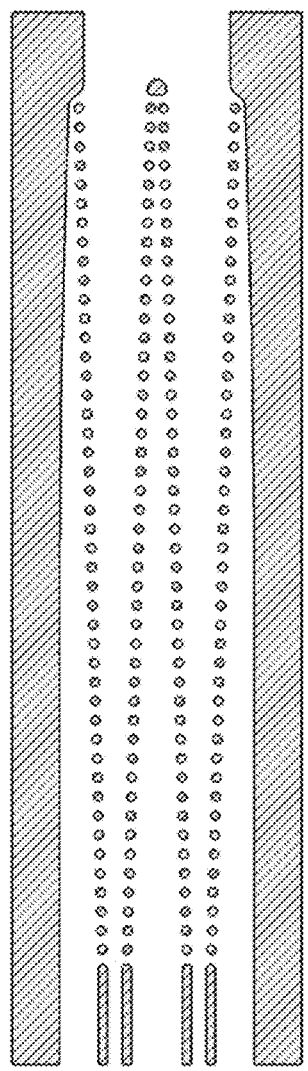
FIGS. 16A and 16B show top views of two multiple filter modules.
Figure 16B:
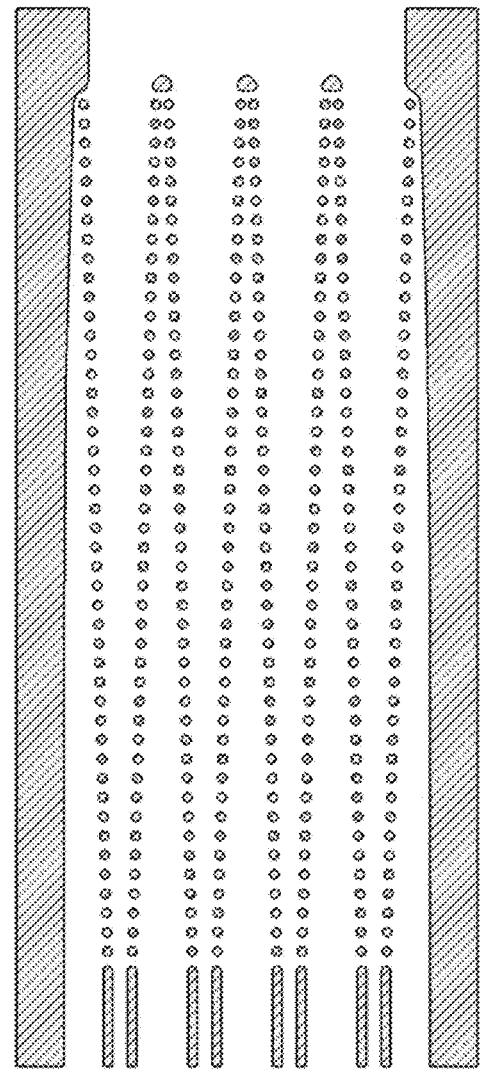

Two dual filter modules can further share a retentate chamber or a filtrate chamber to form multiple filter modules (FIG. 16). In the embodiment shown in FIG. 16A, two dual filter modules (FIG. 14A) share a filtrate chamber and form a multiple filter module that has four filters in the module. Further, more than two dual filter modules can also share retentate chambers or filtrate chambers to form multiple filter modules (FIG. 16B). A dual filter module design may also be combined with a filter module to form a multiple filter module comprising three filters. A multiple filter module design may also be combined with a filter module in a similar fashion.

Filter Cascade Module

In some embodiments, two or more filter modules, dual filter modules, or multiple filter modules may be connected in series to form a "filter cascade module." In the embodiment shown in FIG. 17A, two substantially identical filter modules 171, 172 are connected in series. The inlet 177 of the second module 172 is in fluid connection with the outlets 503, 507 of the first module 171. Feed particles may enter the inlet 502 of the first module 171 and may be separated into retentate and filtrate by the first filter 173. When the device is operated in laminar flow conditions, the retentate and the filtrate may form two laminar flow streams side by side without convictive mixing after separation. As the two particles streams enter the second module 172, the filtrate from the first module 171 may encounter the second filter 174 by which some particles may be retained. The retentate of the filter cascade module 170 may be collected at outlet 503. The filtrate of the filter cascade module 170 as a whole may pass through both filters 173, 174, and may be collected at outlet 507. This embodiment increases the recovery yield of retentate particles, as particles that may not be retained by the first filter 173 may be retained by the second filter 174. Similarly, two or more dual filter modules may be combined in series to form a filter cascade module (FIG. 17B). The inlet 177 of the second module 172 may be in fluid connection with the outlets 503, 507 of the first module 171. More than two dual filter modules may be connected in a similar fashion. Other filter configurations, such as multiple filter modules, may also be combined in series to form a filter cascade module.

Figure 17C:
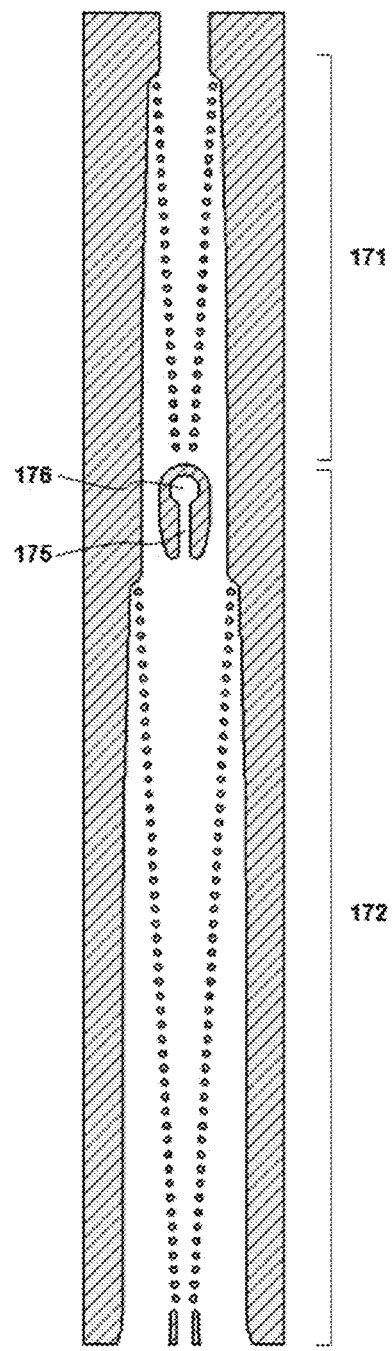
Figure 17D:
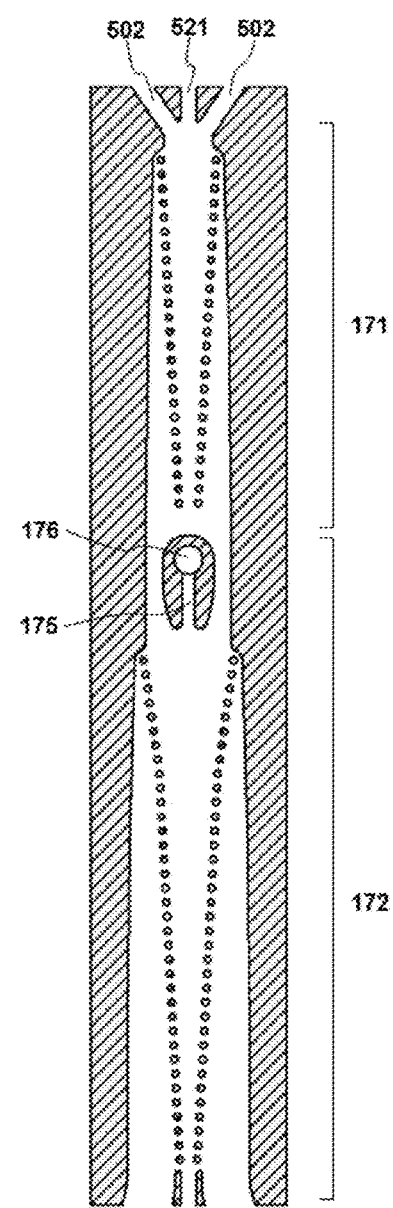

It is understood that filter modules, dual filter modules, or multiple filter modules that are connected in series to form a filter cascade module may or may not be substantially identical, and may or may not have substantially identical effective pore sizes or retention sizes. In any of the filter cascade module embodiments, the retentate chamber of a module may further comprise a carrier flow inlet. FIG. 17C shows a filter cascade module embodiment comprising two dual filter modules 171, 172. The dual filter module 172 comprises a carrier flow inlet 175, which may comprise a channel and a through hole 176. FIG. 17D shows a filter cascade module embodiment comprising two dual filter modules comprising two carrier fluid inlets 521, 175.

Figure 18A:
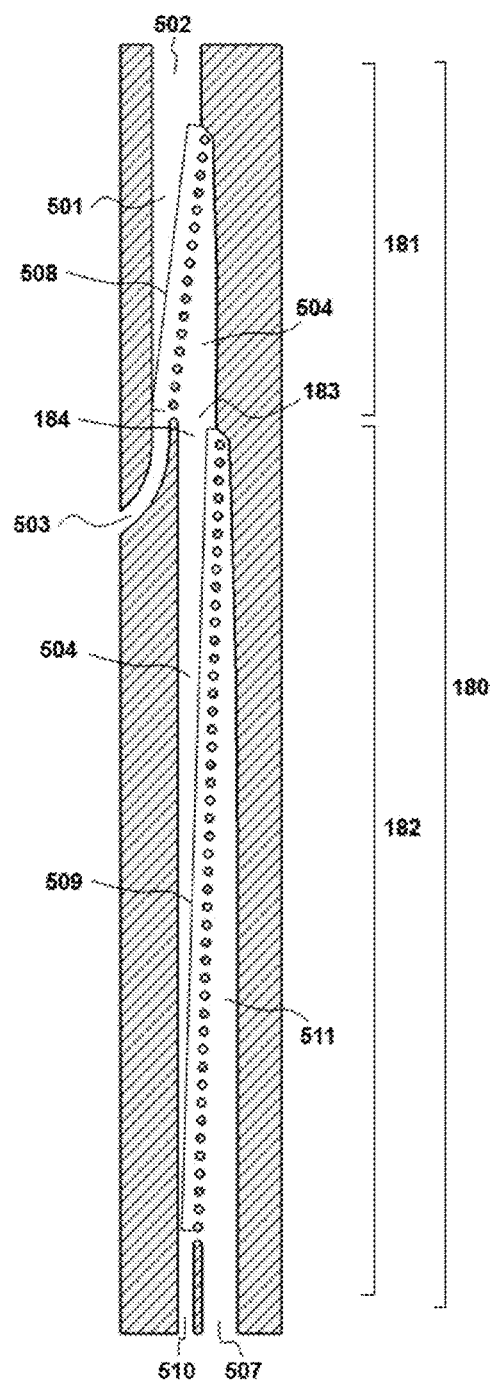
FIGS. 18A-18C are schematic diagrams that provide top views of filter cascade modules comprising different filter modules.
Figure 18B:
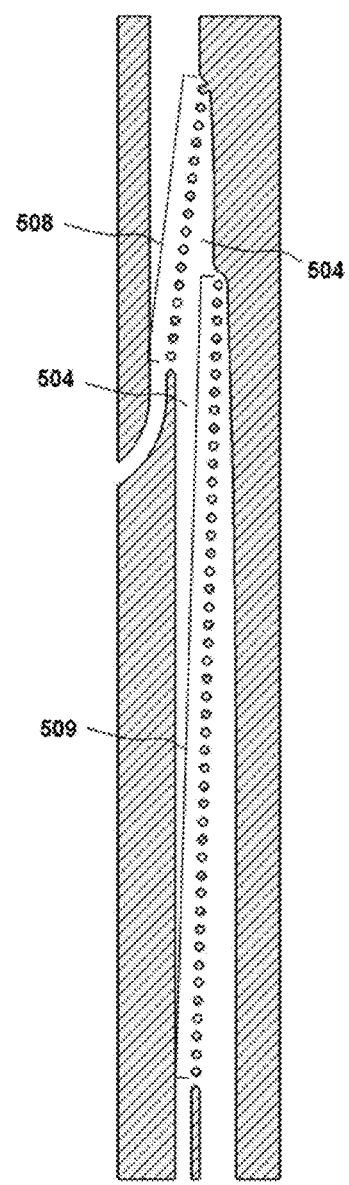
Figure 18C:
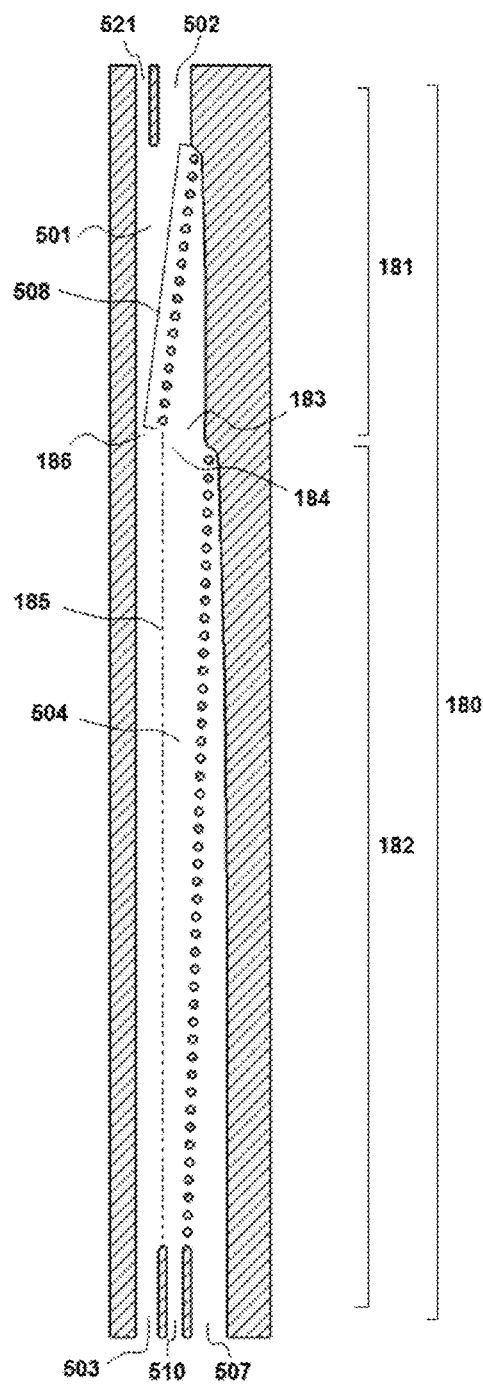

Different filter modules, dual filter modules, or multiple filter modules of substantially different effective pore sizes or retention sizes may be combined to form a filter cascade module that can fractionate feed into multiple fractions. In one embodiment, shown in FIG. 18A, a cascade module 180 comprises a first filter module 181 and a second module 182. The first module 181 comprises a first chamber 501 comprising an inlet 502 for the feed, and an outlet 503 for a first retentate, herein referred to as "fraction 1." A first filter 508 is disposed between the first chamber 501 and a second chamber 504. The second chamber may be designed to draw a small amount of flow through the pores at the first filter 508 to facilitate flow exclusion, and may receive the filtrate from the first filter as the first filtrate. The filtrate outlet 183 of the first module 181 is in fluid connection with the inlet 184 of the second module 182. The second module 182 comprises a filter 509 that may retain a subpopulation of the first filtrate as "fraction 2," which is harvested at an outlet 510. A third chamber 511 may be placed to receive the filtrate of the second filter 509, and may draw a small amount of flow through the pores of the second filter to facilitate flow exclusion. The filtrate of the second filter 509 may exit via outlet 507, and is herein referred to as "fraction 3." The second module 182 may employ a smaller retention size than that of the first module 181. The two modules 181, 182 can be arranged to reduce the length of the second chamber 504 (FIG. 18B). In another embodiment of the present disclosure, shown in FIG. 18C, a cascade module 180 comprises a first filter module 181 and a second module 182. The inlet 184 of the second module 182 is connected to the outlets 183, 186 of the first module 181. When the module 180 is operated under laminar flow conditions, the filtrate and the retentate from the first module 181 may flow side by side as two separated flow streams without convective mixing. The interface between the two streams is shown as the dashed line 185. The cascade module 180 may fractionate feed particles into three different fractions, fraction 1, fraction 2, and fraction 3, which may be collected via exits 503, 510 and 507 respectively. To increase the purity of fraction 1, a carrier fluid may be introduced via inlet 521.

Figure 18D:
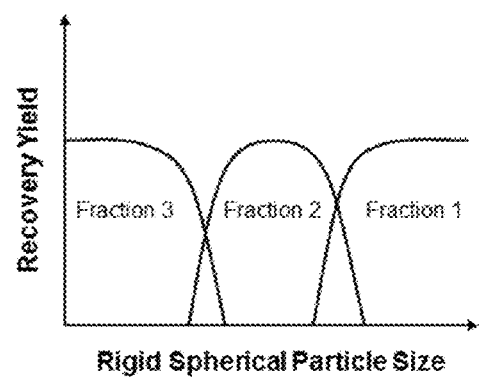
FIG. 18D is a graph showing qualitative filtration characteristics.

FIG. 18D depicts qualitatively the size distribution outcome that a cascade module may achieve when separating dilute rigid spherical particles into three fractions. Complex feeds, such as blood, may be separated into three or more fractions. The separation may be based on several factors, including particle-particle interactions, deformation of particles, and/or non-Newtonian fluid behaviors.

Figure 19A:
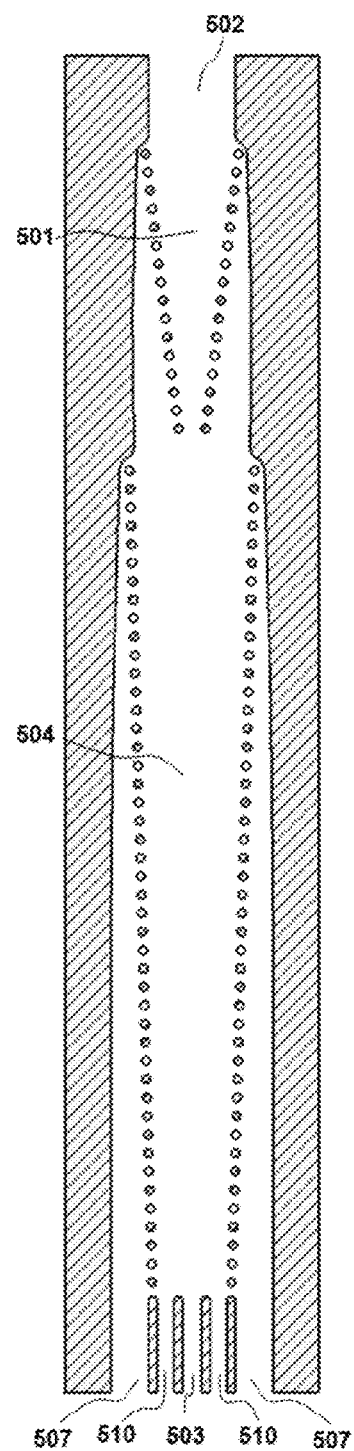
FIGS. 19A and 19B show top views of filter cascade modules comprising different dual filter modules.
Figure 19B:
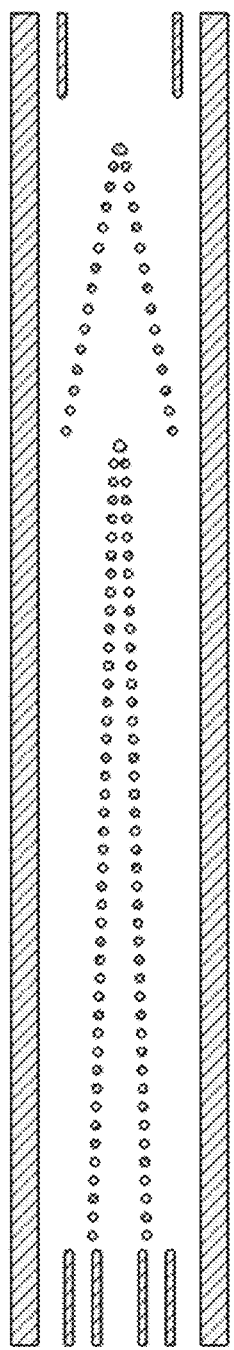

Dual filter modules and multiple filter modules may be cascaded to form filter cascade modules, similar to the manner that filter modules may. FIG. 19 shows two such embodiments. FIG. 19A shows an embodiment that represents a minor image arrangement of two filter cascade modules shown in FIG. 18C, while sharing the retentate chamber 501. Particles are fractionated and collected at outlets 503, 510, 507. Similarly, two filter cascade modules of FIG. 18C may share chambers 504 to form an embodiment shown in FIG. 19B.

Filter cascade modules may be useful for separating particles into three or more fractions according to the particles' mechanical properties, e.g. size, shape, deformability, flexibility, elasticity, and/or viscosity. For example, a filter cascade module may fractionate whole blood into lymphocyte, granulocyte, and erythrocyte populations. Another embodiment of a filter cascade module may fractionate enzyme digested fat tissues into fat cells, a stromal vascular fraction comprising adipose stem cells, and blood cells.

Figure 20A:
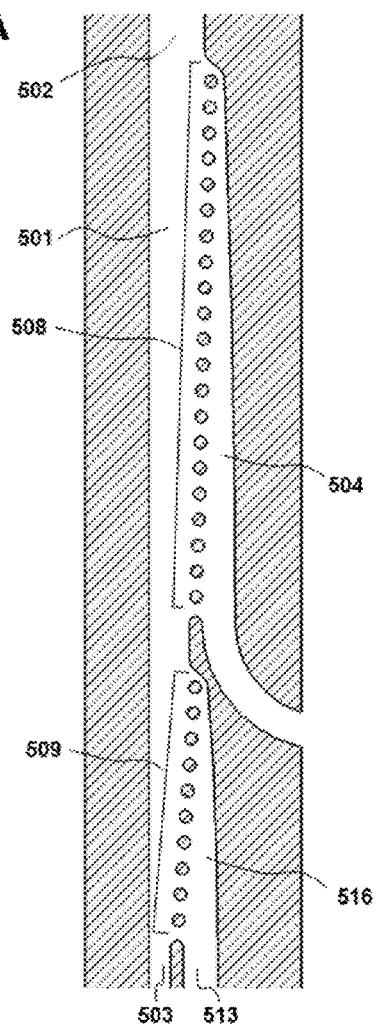
FIGS. 20A and 20B are schematic diagrams.

Another embodiment of a filter cascade module is shown in FIG. 20A. A retentate chamber 501 may receive a feed fluid at an inlet 502. The feed may be driven against a first filter 508. A first filtrate chamber 504 may be configured to draw small amounts of flows through pores of the first filter 508 to facilitate flow exclusion, and to collect the filtrate from the first filter 508. The retentate of the first filter 508 may enter the second filter module against a second filter 509. A second filtrate chamber 516 may be configured to draw small amounts of flows through pores of the second filter 509, and to collect the filtrate from the second filter 509 via an outlet 513. The effective pore size of the first filter 508 may be configured to be smaller than the effective pore size of the second filter 509. The retentate of the second filter may be harvested via an outlet 503 at the retentate chamber 501.

Figure 20B:
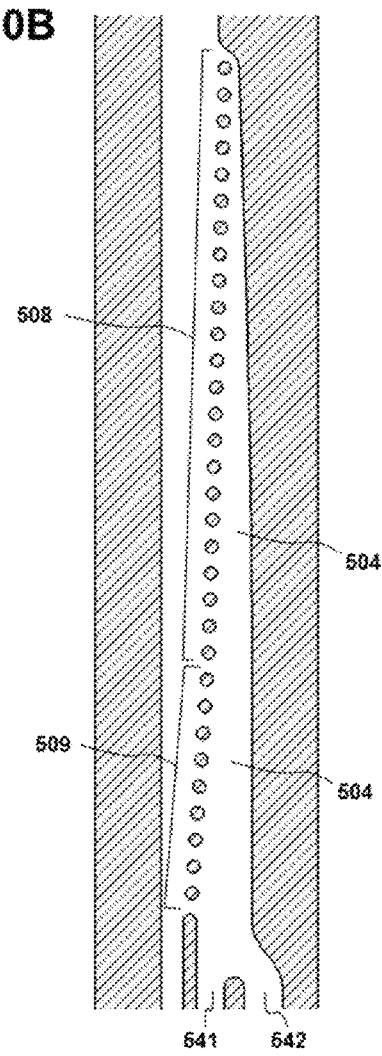

The embodiment of FIG. 20A may be simplified to that shown in FIG. 20B, because of the laminar flow operating conditions. Filtrates of the two filters 508, 509 of different retention sizes may be collected by the same filtrate chamber 504. The two filtrates may not mix convectively and may therefore be collected separately via two outlets 541, 542.

Figure 20C:
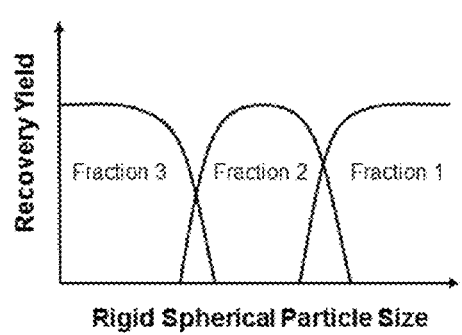
FIG. 20C is a graph showing qualitative filtration characteristics.

In the embodiments shown in FIGS. 20A and 20B, the feed particles may be fractionated into three fractions: the filtrate of the first filter 508 (fraction 3), the filtrate of the second filter 509 (fraction 2), and the retentate of the second filter 509 (fraction 1). For feed comprising rigid spherical particles, an example of the size distribution of the three fractions is depicted qualitatively in FIG. 20C. It is appreciated that the filter cascade modules may form dual filter cascade modules (FIG. 21), much as two filter modules may form a dual filter module (FIG. 14, 15). The dual filter modules in FIGS. 20A and 20B may further cascade to form cascade modules in the same manner that two dual filter modules of FIG. 14A may form a cascade module shown in FIG. 17B.

It is appreciated that filter cascade modules may comprise cascades of two or more filter modules, dual filter modules, or multiple filter modules.

The above embodiments of filter cascade modules may also employ a carrier flow or multiple carrier flows to increase the purity of retentates, to wash the particles, to treat the particles with different reagents as the carrier flow, or to label the particles.

It is appreciated that a dual filter cascade module may comprise filters of more than two retention sizes, to separate a feed into more than three fractions. It is also appreciated that although the embodiments of dual filter cascade modules described above are symmetric with respect to the centerlines, a dual filter cascade modules may be asymmetric, or may even comprise filters of different effective pore sizes on opposite sides of the centerline.

Other Module Configurations

In another embodiment of the present disclosure, a filter module, comprising a retentate chamber, a filter, and a filtrate chamber, may be curved. Such a filter module embodiment may have the advantage of a reduced footprint, when a long filter length is desired. Alternatively, filter modules and filter cascade modules may be arranged in a serpentine shape.

Figure 22A:
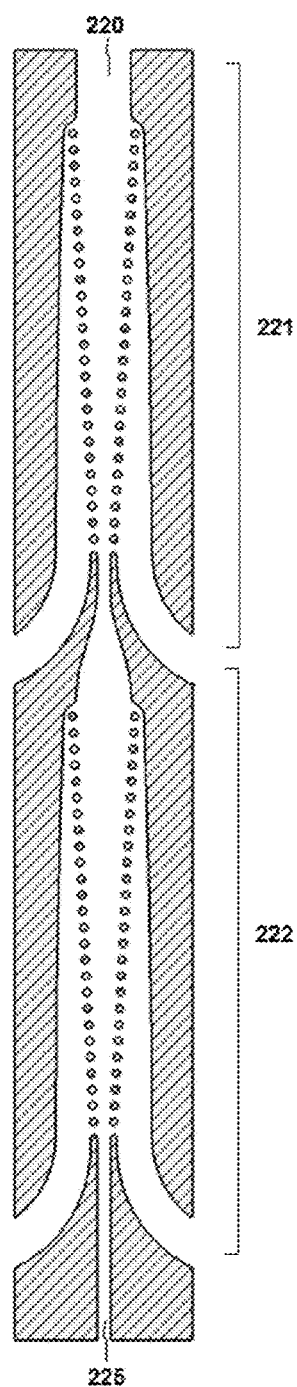
FIGS. 22A and 22B are schematic diagrams that provide top views of two dual filter cascade module configurations.

Modules may be combined in ways to attain different filter characteristics. For example, FIG. 22A shows an embodiment of the present disclosure to concentrate retentate particles effectively. Feed may enter the first module 221 via inlet 220. The first module may concentrate target particles in the feed as its retentate. The retentate may enter the second module 222 as feed and may be concentrated again, before exiting via an outlet 225. If each module concentrates its feed by a volume reduction factor of 5, then the two modules together may reduce the volume by a factor of 25. More modules, for example, 3, 4, or 5, may be linked together in a similar fashion to get even more concentrated output. If three modules are cascaded in a similar fashion, and if each module has a volume reduction factor of 4, then the three modules together may reduce the volume by a factor of 64. It is appreciated that the modules do not have to concentrate particles by the same factor.

Figure 22B:
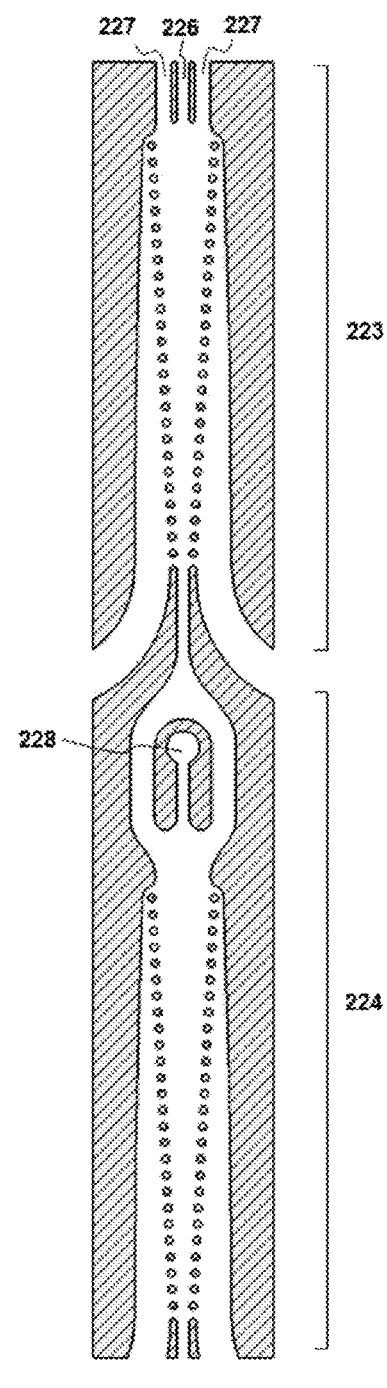

FIG. 22B shows an embodiment of the present disclosure where retentate particles may be washed effectively. Feed may enter a first module 223 via inlets 227. A carrier fluid may be introduced via inlet 226. The retentate of the first module may be "washed" by the carrier flow, and may enter a second module 224. The second module may comprise an inlet 228 for a second carrier flow. The inlet 228 may comprise a through hole in the embodiment. The second carrier flow may or may not be identical with the first carrier flow. The retentate from the first module 223 may be washed by the second carrier flow in the second module 224. This embodiment may be used to deplete filtrate particle population more completely and get higher purification of the retentate particle population. It may also be used to treat, wash or label retentate particles using carrier flows. For example, the carrier flow may comprise antibody against a target antigen on the retentate population. As the retentate particles move into the carrier flow stream, the target particles may be labeled by the antibody. It is appreciated that more than two modules may be cascaded in similar fashions.

Figure 23C:
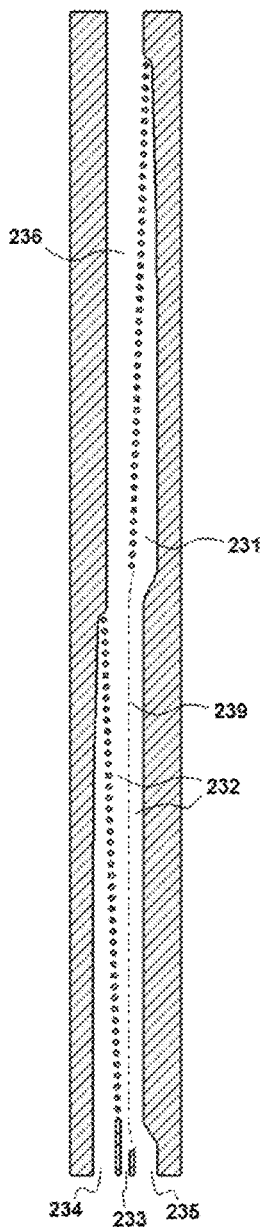

FIGS. 23A, 23B, and 23C show embodiments of dual filter modules where the constituting modules are offset from each other. In the embodiment shown in FIG. 23B, feed particles may enter a retentate chamber 236 via an inlet 230. The particles may be separated into a retentate fraction and a filtrate fraction by a filter 237. The filtrate may flow through a filtrate chamber 231 and may enter another chamber 232. Although this chamber 232 may allow the filtrate from the first filter 237 to pass through, the chamber 232 may also serve as a retentate chamber for a second filter 238. Because of the laminar flow conditions, the retentate and the filtrate may not mix convectively, and may be collected after they flow through the retentate chamber 232. The filtrate fractions from the first filter 237 and the second filter 238 may exit via a first outlet 235 and a second outlet 234, respectively, whereas the retentate fractions of both filters 237, 238 may be collected via an outlet 233. Similarly, in the embodiment shown in FIG. 23C, retentate from a first retentate chamber 236 and filtrate from a first filtrate chamber 231 may flow side by side through a second retentate chamber 232. Under laminar flow conditions the retentate and filtrate do not mix convectively. The dashed line 239 shows the fluid interface between the retentate and the filtrate, which may exit via two different outlets 233, 235 respectively.

Figure 23D:
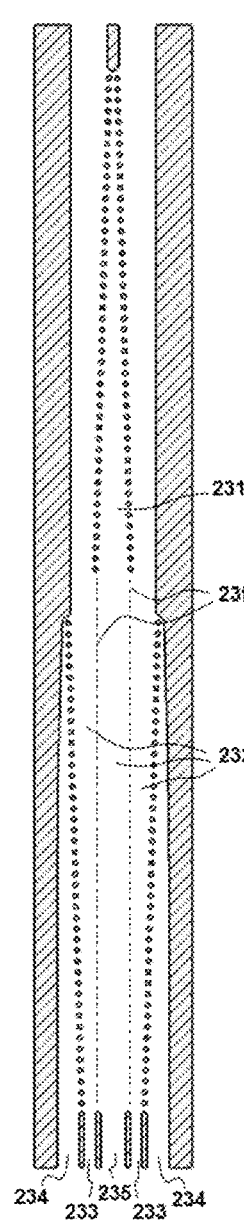
FIG. 23D is a schematic diagram showing a multiple filter module.

FIG. 23D shows an embodiment of a multiple filter module. This module comprises two modules shown in FIG. 23C as minor images with respect to each other. The filtrate chambers 231 and the retentate chambers 232 are shared. Because the flow is laminar, filtrate and retentate streams may not mix convectively. The interfaces between the streams are shown as the dashed lines 239. Filtrate streams may be collected via outlets 234, 235, whereas retentate streams may be collected via outlets 233.

Figure 23E:
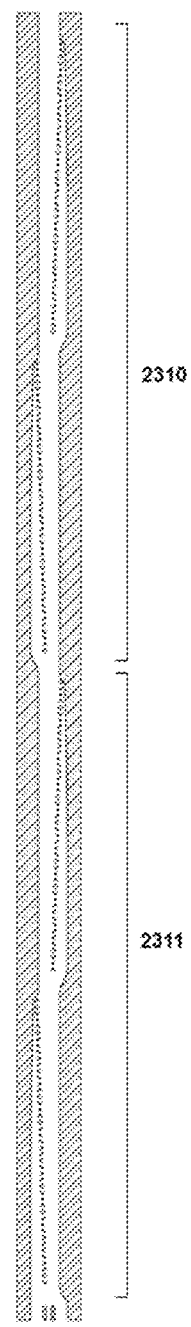
FIG. 23E is a schematic diagram showing a filter cascade modules comprising two dual filter modules shown in FIG. 23C.

FIG. 23E shows an embodiment of a filter cascade module. This filter cascade module comprises two modules 2310, 2311, each of which comprises a module shown in FIG. 23C.

It is understood that the various filter module designs and configurations described above are by way of example only, and are not intended to be limiting. In the spirit of the present disclosure, the filter may comprise pillars of various cross sections, as shown in FIG. 9. Modules may be combined and/or cascaded in various ways to form dual filter modules, multiple filter modules, various filter cascade modules, etc. A carrier flow or multiple carrier flows may be introduced to the various modules to facilitate filtrate population depletion, filtrate population removal, particle washing, particle labeling, particle treatment, and so on.

Structural Conditions for Flow Exclusion

To achieve an effective pore size that is substantially smaller than the physical pore size, a filtrate chamber of a filtration device may be configured to expand gradually. One skilled in the art can consider the conditions when flow exclusion may occur in embodiments of the present disclosure.

Figure 12:
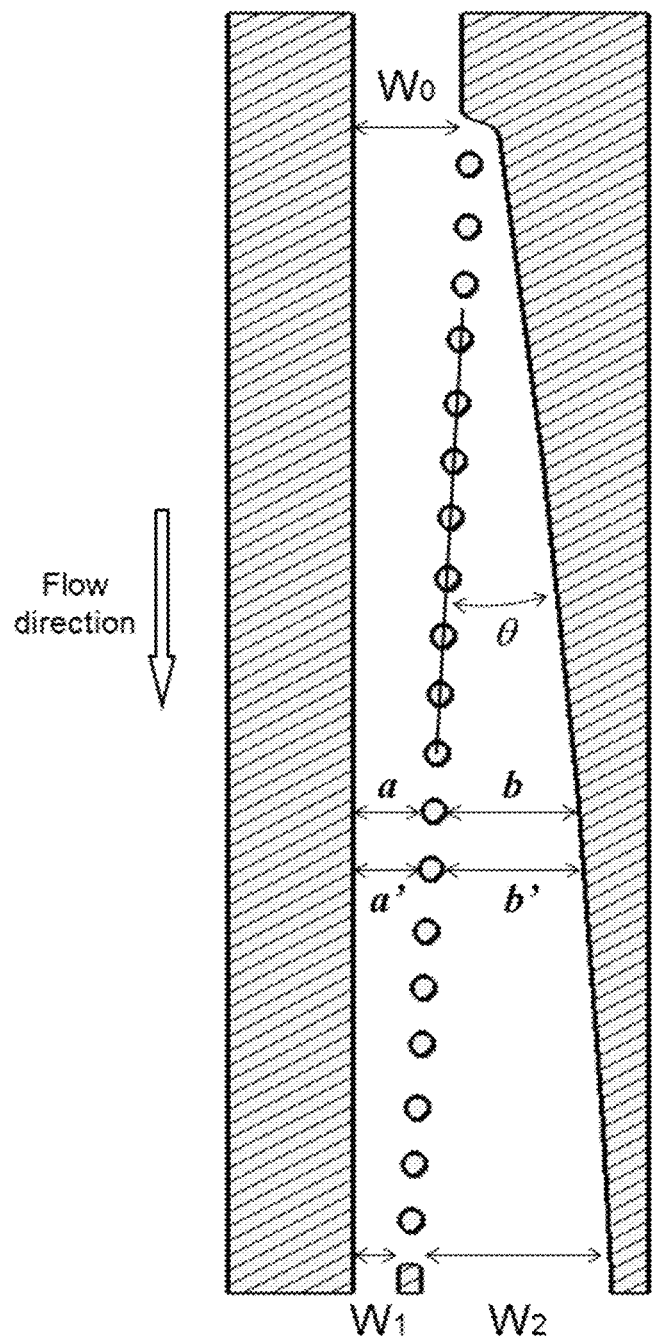
FIG. 12 is a schematic diagram showing a top view of a filter module.

Without being bound to any particular mathematical formulas, equations, derivations and theories, conditions that may encourage flow exclusion are described below. For example, let us consider the embodiment shown in FIG. 12. Because the flow through a pore is controlled by the expansion and contraction of the chambers, for example, the widening of the filtrate chamber and/or the narrowing of the retentate chamber, let us define the "proportional filtrate chamber cross sectional area" w as the ratio between the cross sectional area of the filtrate chamber and the cross sectional area of all the chambers, where the cross sections are taken substantially perpendicular to the average flow direction. When a filtration module has chambers of substantially constant depth, as in the embodiment shown in FIG. 12, the "proportional filtrate chamber cross sectional area" w is $$w = \frac{b}{a+b},$$

where a is the width of the retentate chamber and b is the width of the filtrate chamber at a cross section of interest. The flow through a pore as a fraction of the total flow in the chambers is substantially depends on the increment of the "proportional filtrate chamber cross sectional areas" around the pore. In the embodiment shown in FIG. 12, the increment is designated as $$w' - w = \frac{b'}{a'+b'} - \frac{b}{a+b}$$

On the other hand, because the amount of flow drawn through a pore is approximately proportional to the area of the pore opening and the average flow speed through the pore, and because the amount of flow going down the chambers is approximately proportional to the total cross sectional area of the chambers and the average flow speed in the chambers, it is expected that the flow through a pore as a fraction of the flow in the chamber is substantially proportional to the physical pore size squared divided by the total cross sectional area of the chambers.

Because flow exclusion occurs when the flow through the pore is weaker than the physical pore size may allow (FIG. 4), one condition for substantial flow exclusion to occur may therefore be $$w' - w < \frac{\text{(Physical Pore Size)}^2}{3 \times \text{(Total Cross Sectional Area)}}$$

The factor of three at the denominator is a proportional factor estimated by computer simulation (FIG. 4). This criterion is herein referred to as the "filtrate chamber expansion criterion." In some embodiments of the present disclosure, a filtration module comprises a retentate chamber, a filtrate chamber, and a filter comprising pillars and pores comprising a physical pore size, wherein the filtrate chamber expands at a rate that satisfies the "filtrate chamber expansion criterion." In some embodiments of the present disclosure, the angle(s) at which the filtrate chamber widens, i.e. the varying or fixed angle(s) between the filter and the filtrate chamber sidewall, is very small, for example, about 0.1 degrees, 0.2 degrees, 0.3 degrees, 0.5 degrees, 0.7 degrees, 1 degree, 1.5 degrees, 2 degrees, 2.5 degrees, 3 degrees, or 5 degrees.

Another condition that may encourage flow exclusion is to incorporate a large number of pores in a filtration module, because when there are more pores, the flow through each pore may be reduced and flow exclusion may occur. Similar to the previous derivation, it is expected that the number of pores that may be required for flow exclusion depends substantially on the amount of flow collected at the filtrate chamber, and the amount of flow allowed by a pore comprising a physical pore size. Therefore, the minimum number of pores that may be required for flow exclusion may be substantially proportional to the ratio between the cross sectional area of the filtrate chamber outlet, and the physical pore size squared. Therefore another condition for substantial flow exclusion may be $$N \geq 3k \frac{\text{(Retentate chamber inlet cross sectional area)}}{\text{(Physical pore size)}^2},$$

where N is the number of pores in a module and k is the "proportional filtrate chamber cross sectional area" on the outlet side of the filtration module. The proportion factor of three is estimated using computer simulation. This criterion is herein referred to as the "minimum pore number criterion." For the embodiment shown in FIG. 12, the condition for substantial flow exclusion may be $$N \geq 3\left(\frac{W_2}{W_1+W_2}\right)\frac{(W_0 D)}{\text{(Physical pore size)}^2}$$

In some embodiments of the present disclosure, a filtration module comprises a retentate chamber, a filtrate chamber, and a filter comprising pillars and pores comprising a physical pore size, wherein the number of pores satisfies the "minimum pore number criterion."

It is understood that the above theory, formulas, equations, and derivations are not meant to be limiting. It is appreciated that the "filtrate chamber expansion criterion" and "minimum pore number criterion" may be applied to various embodiments in accordance with the present disclosure filtration modules, including but are not limited to filter modules, dual filter modules, multiple filter modules, and filter cascade modules.

Filtration Units

One embodiment of the present disclosure is a filtration unit comprising a filtration module disclosed above, fluidic channels, and ports. The fluidic channels are configured to provide fluid connection between the ports and the module. The fluidic channels may also be configured to provide appropriate fluidic resistances to establish desired flow distributions in the module, for example, the correct proportions of feed and carrier fluid in the module and/or the correct proportions of fluids collected as the retentate and the filtrate, under desired operating conditions.

High Module Density Devices

One of the significant advantages of some embodiments of the present disclosure is to enable high throughput and high capacity devices for flow exclusion-based particle filtration, while maintaining compact device footprints and low shear. The above disclosed module and unit configurations are compact and may be easily patterned into devices of high module density. Such devices may have scalable capacity and processing throughput, and may be extremely useful for many applications, such as volume reduction of umbilical cord blood, cell washing, isolation of stem cells, preparation of stromal vascular fractions, plasma skimming, and filtration of bone marrow stem cells. Stacking many of these compact devices together as one device may provide even higher capacity and throughput.

In another embodiment of the present disclosure, a device comprises a plurality of filtration units, where each filtration unit comprises a module disclosed above and fluidic channels that are in fluid connection with the module. In yet another embodiments of the present disclosure, a plurality of filtration units, for example, about 3, 5, 8, 10, 15, 20, 30, 50, 75, 100, 150, 200, 300, 500, 800, or more filtration units, is disposed in a high density configuration on a single device. Such a device is herein called a "high module density device."

Figure 24A:
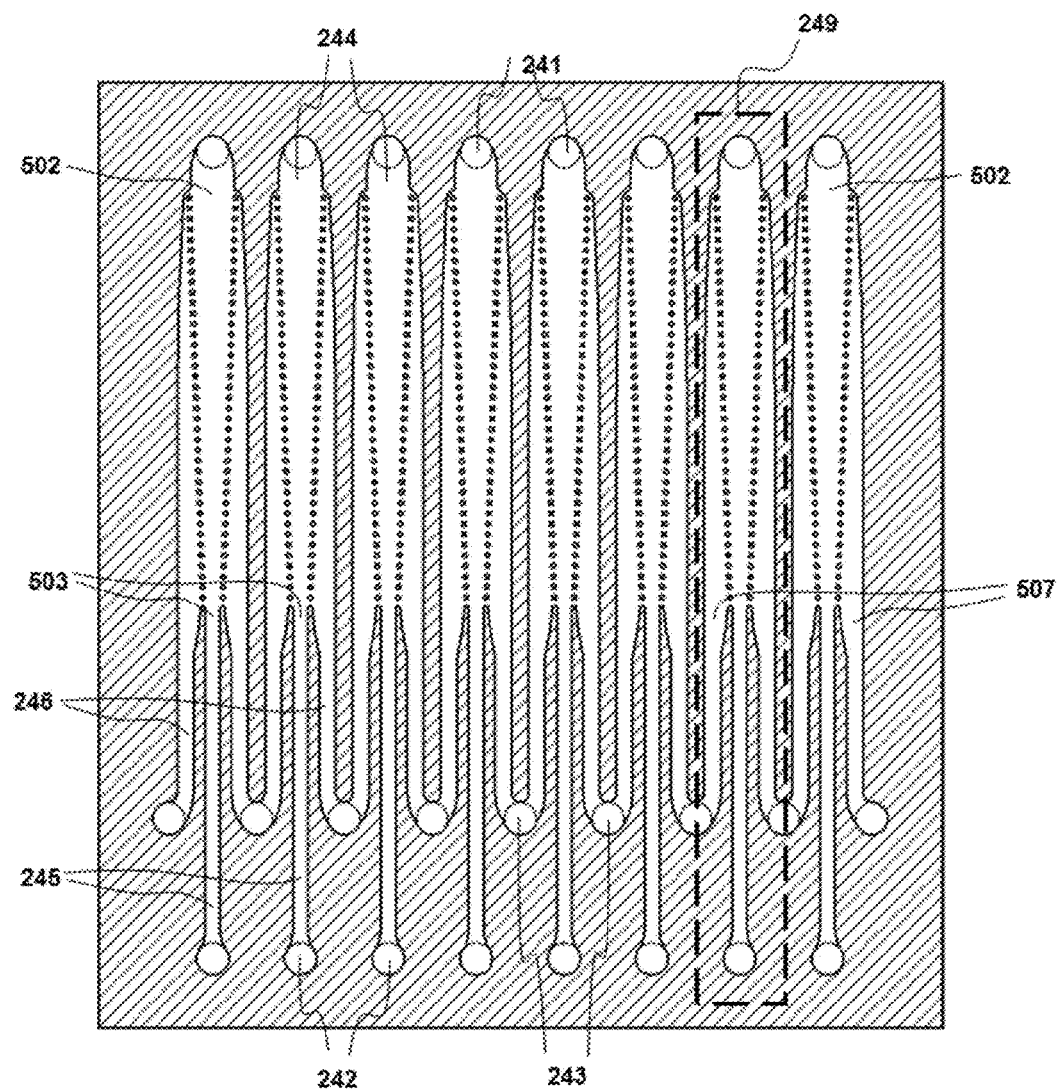
FIGS. 24A-24F are schematic diagrams.

FIGS. 24A-24F show several embodiments of the high module density devices where filtration units 249 are repeated to increase throughputs and capacities. In FIG. 24A, eight filtration units, each comprising a dual filter module, are disposed. The feed inlets 502, retentate outlets 503, and filtrate outlets 507 of the modules are connected to input ports 241 and output ports 242, 243 using inlet channels 244 and outlet channels 245, 246 respectively.

The flow resistances across the channels 244, 245, 246 may be configured to establish proper amounts of flows entering the inlets 502 and exiting the outlets 503, 507 under operating conditions, and to facilitate the operation of the individual modules. The flow resistances across the channels 244, 245, 246 may be designed to be smaller than, appreciable to, or greater than the flow resistance of the modules, depending on the operation conditions for which the device is designed. In some embodiments, the flow resistances across the inlet and outlet channels 245, 246 may be from about 0.01 to about 0.99 times the dual filter module resistance.

In another embodiment of the present disclosure (FIG. 24B), each dual filter module may comprise a carrier flow inlet 521, which may be connected to an input port 247 via a channel 248. The flow resistances of the channels may be designed to facilitate the proper operation of the individual modules. In yet another embodiment of the present disclosure (FIG. 24C), a multiple filter module is connected to input and output ports using channels. In yet another embodiment of the present disclosure (FIG. 24D), many modules may share an input port 241 and an output port 242. The channels connecting the modules to the ports may be designed to have substantially equal resistances. In yet another embodiment of the present disclosure (FIG. 24E), modules may be disposed on a circular disk. In the embodiment of FIG. 24E, the disk may be spun about a central axis to generate a centrifugal force which may drive a fluid through the modules disposed on the disk.

Figure 24F:
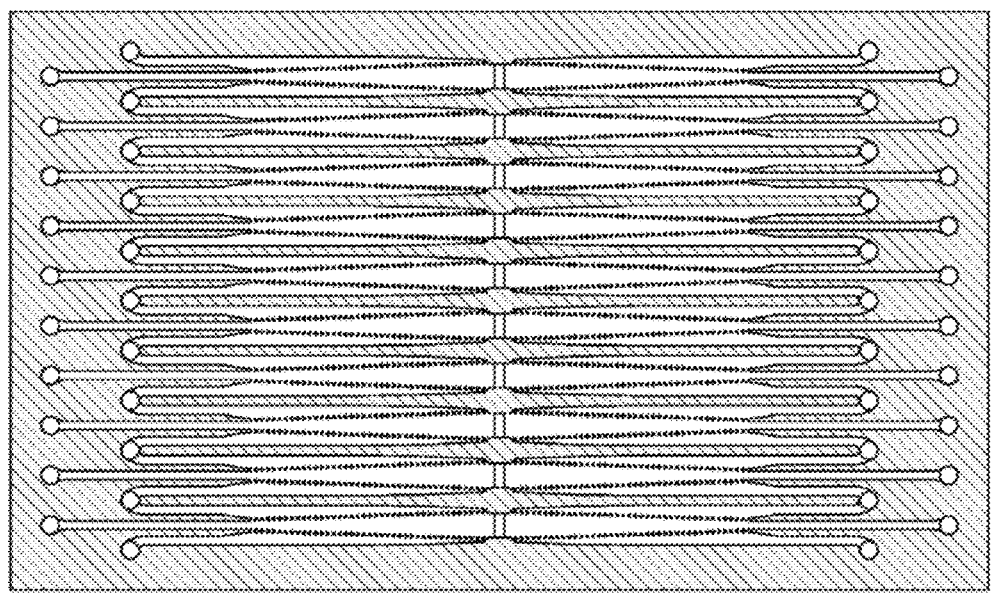
Figure 25:
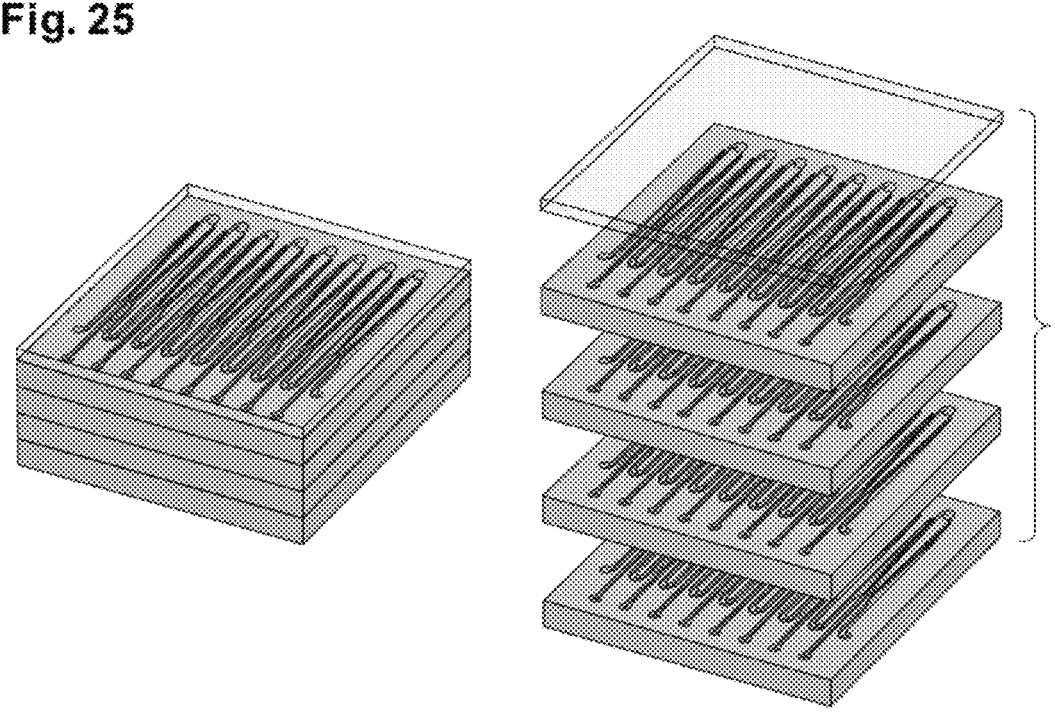
FIG. 25 is a schematic diagram showing a three dimensional assembled view and a three dimensional exploded view of a device comprising a stack of four high module density devices and a lid.

Modules are not limited to be disposed in just one row. Two or more rows of modules may be disposed as one device. With two or more rows of modules, there are more possible arrangements to share ports and reduce the footprints of the devices. FIG. 24F shows a plurality of 20 dual filter modules disposed in two rows sharing common feed input ports. Furthermore, devices may be stacked to achieve high capacity and throughput (FIG. 25).

It is appreciated that a plurality of filter modules, dual filter modules, filter cascade modules, dual filter cascade modules, multiple filter modules, multiple filter cascade modules, other configurations, or any combinations of the above modules may be placed in any possible two or three dimensional relationship with respect to one another.

Filtration Device Manufacturing Techniques

A variety of techniques may be used to fabricate embodiments of devices in accordance with the present disclosure. In one embodiment of the disclosure, a device may be micromachined. Micromachining techniques may be selected from, but are not limited to, those known in the art, for example, techniques conventionally used for silicon-based integrated circuit fabrication, embossing, soft embossing, casting, imprinting, molding, injection molding, extrusion, stereo laser lithography, selective laser sintering, photodefinable glass lithography and wet etching, computer numerical control (CNC) machining, polydimethylsiloxane (PDMS) soft lithography, ultrasound micromilling, thick photoresist lithography, combinations of the above techniques, and so on. Examples of suitable fabrication techniques include photolithography, deep reactive ion etching, wet etch, molding, embossing, imprinting, laser ablation, thick photoresist lithography, soft lithography, radiation track etching, and other techniques. Some aspects and embodiments of filtration devices may be made of materials that are compatible with the conditions present in the particular application of interest. Such conditions may include, but are not limited to, pH, temperature, organic solvents, biocompatibility, ionic strength, pressure, application of electric fields, sticking properties, surface charge, surface functionalization, surface treatment, wet angle, hydrophilicity, hydrophobicity, mechanical strength, and heat expansion. The materials of the device may also be chosen for their optical properties, mechanical properties, chemical properties, chemical resistance to solvents, melting properties, and for their inertness to components of the application to be carried out in the device. Such materials may include, but are not limited to, glass, fused silica, silicone rubber, silicon, ceramics, photodefinable glass, plastics, polymeric materials, photosensitive polymers, thick photoresist, SU-8 resist, polydimethylsiloxane (PDMS), cyclic olefin copolymer (COC), cyclic olefin polymer (COP), polycarbonate, polyethylene, polypropylene, polymethylmethacrylate (PMMA), pressure sensitive materials, Teflon, acrylic, polyethersulfone, polytetrafluoroethylene, etc. The devices may be sterilized using standard sterilization techniques, e.g. gamma irradiation, ethylene oxide (EO) sterilization, ultra violet light illumination, autoclaving, etc.

Efficiency Metrics for Characterizing Microfluidic Filtration Modules, Units and Devices Compared to other microfluidic devices, some aspects and embodiments of the present disclosure create conditions for flow exclusion much more efficiently. Embodiments of a filter module in accordance with the present disclosure may be disposed as one physically compact device, e.g. a high module density device, that has a desired capacity and/or throughput. Embodiments of the present disclosure may have many significant advantages. For example, embodiments of the present disclosure may not be susceptible to clogging. Second, some aspects and embodiments of the present disclosure may be relatively easy to manufacture because these aspects and embodiments may comprise a very small footprint and a relatively small number of pillars. Third, some aspects and embodiments of the present disclosure may tend to be gentle to the particles being filtered. In some embodiments a filtrate particle may go through as few as one pore per module during the filtration process. Fourth, some aspects and embodiments of the present disclosure introduce little diffusion, because particles are not subject to the constant collision and scattering that other designs may inflict. Little diffusion may result in highly efficient separation.

Aspects and embodiments of the present disclosure may comprise high throughput, low shear, and compact filtration devices that are easy and cost effective to manufacture. Metrics can be defined to quantify the efficiency of a device design and the potential efforts required to manufacture. One metric that reflects the potential efforts required to manufacture a microfluidic filtration device is the hold up volume of the device. The hold up volume is the void volume inside a device, and may represent the amount of material that is removed or displaced during the device fabrication process. For example, one method for fabricating microfluidic filtration devices in silicon is photolithography followed by reactive ion etching. The number of devices that can be made on a wafer depends on the size of the etched area in a device, whereas the machine time for reactive ion etching depends on the etch depth. The hold up volume of a device may be approximately the size of the etched area multiplied by the etch depth, and therefore may represent the efforts and costs required to fabricate the device. For example, for filtration devices microfabricated in silicon using microfabrication, the larger the hold up volume a device has, the more wafer material, photolithography efforts, and etching machine time will be needed. Other device fabrication techniques, such as injection molding, also result in similar correlations between the hold up volume and the efforts needed to make the device.

For microfluidic filtration devices comprising one or more filtration modules, e.g. a filter module, a dual filter module, a filter cascade module, or a multiple filter module, the hold up volume of the filtration module can serve as a good metric for characterizing the filtration module and or the device. Some aspects and embodiments of the present disclosure comprise filtration modules with small hold up volume, e.g. a filtration module may comprise a hold up volume of <1 µl, <0.3 µl, <0.1 µl, <0.03 µl, <0.01 µl, or smaller. The hold up volumes of several exemplary embodiments of the present disclosure are calculated and disclosed in the example section below.

Another metric that can be defined to estimate the efforts required to manufacture a module is the "filtration unit density," defined herein as number of filtration units per volume. More specifically, the "filtration unit density" may be calculated as $$\text{Filtration Unit Density} = \frac{\text{(Number of Modules per Device)}}{\text{(Device Footprint)} \times \text{(channel Depth)}}$$

For example, consider a high module density device having 100 identical filtration units, a footprint of 2 cm×2 cm, and an average characteristic channel depth of 50 µm, the "filtration unit density" is 100/[(2 cm×2 cm)×50 µm], which equals to 5,000 cm$^{-3}$. Such a "filtration unit density" means that in principle, up to 5,000 filtration units can be packed in a high module density device that is a cubic centimeter in size. In order to increase the usefulness and reduce the cost of a microfluidic filtration device, it may be desired to maximize the "filtration unit density" of the device, as the device throughput depends on the number of modules in the device, and the cost tends to scale with the volumetric amount of fluidic features in the device. Some aspects and embodiments of the present disclosure enable devices that have a high "filtration unit density." The "filtration unit density" of several exemplary embodiments of the present disclosure are calculated and disclosed in the example section below.

In addition to the device footprint and the channel depth, an important performance specification of a microfluidic separation device is the particle processing speed, defined as the number of feed particles processed per unit time. To characterize the particle processing speed of a device, it may be important to take into account the device footprint and the fluidic channel depth, which correlates to the manufacturing difficulty and cost of the device. A "normalized processing speed" may be defined for a microfluidic separation device as follows:

$$\text{Normalized Processing Speed} = \frac{\text{(Particle Processing Speed)}}{\text{(Device Footprint)} \times \text{(Channel Depth)}}$$

It may be desired that a device has a high normalized processing speed. Many aspects and embodiments of the present disclosure enable separation devices to have high "processing speed indices." The processing speed indices for several exemplary embodiments of the present invention are calculated and disclosed in the example section below.

Another important factor relating to the efficiency and the manufacturing cost of a microfluidic separation device may be the operating flow speed. Increasing the flow speed in many instances increases the throughput of the device without increasing the manufacturing cost. However, this approach may come with significant limitations for applications where shear stress is a concern. Increased flow speeds may cause higher shear stress conditions, leading to potential particle damage and/or filter fouling. For cell filtration applications, it may be desirable for shear to be limited. Cells may be vulnerable to high shear stress, and may be activated, damaged, altered, or even lysed by high shear stress. Many aspects and embodiments of the present disclosure allow for maximizing the flow speed while limiting the shear.

When comparing throughputs of different microfluidic flow-through separation devices, one may desire to normalize the throughputs according to device footprints, channel depths, and operating shear conditions. Further, the throughputs may be normalized according to the square of the characteristic retention size of the filtration devices, because a device with a larger retention size may tend to have a higher throughput. Herein a "design efficiency index" (D.E.I.), representing the normalized throughput of a microfluidic separation device is defined as:

$$D.E.I. = \frac{Q}{ADSR^2},$$

where Q is the volumetric throughput at which the device processes the feed, S is the maximum shear rate that a particle experiences when flowing through the device, A is the device footprint, which is an area, D is the characteristic depth of the device channels, and R is the retention size of the device. Shear rate herein is defined as the velocity gradient of the fluid in the direction perpendicular to the velocity, and has the dimension of 1/time. The design efficiency index has the dimension of 1/length$^2$, and may be considered an intrinsic property of the device, regardless of the device size, channel depths, operating shear conditions, and retention size.

The "design efficiency index" may be a good indicator for the usefulness of a device design. Devices with high design efficiency indices may be of high throughput, and may be compact, gentle, and easy to manufacture. Design efficiency indices may be extremely useful for characterizing the intrinsic throughput performances of microfluidic flow-through devices for particle filtration, where the operation conditions are such that the flow is laminar, where the Reynolds number Re is low, e.g. <0.01, <0.1, <1, <10, <100, or <500, and where the particle size range is between about 50 nm and about 300 µm.

Aspects and embodiments of the present disclosure may enable devices of high design efficiency indices. The "design efficiency indices" of several exemplary embodiments of the present disclosure are calculated and disclosed in the example section below.

It is appreciated that aspects and embodiments of the present disclosure may enable filtration devices, particularly microfluidic separation devices, to comprise design features that significantly improve the device performance and cost efficiency, as characterized by the hold up volume, the filtration unit density, the normalized processing speed, and/or the design efficiency index metrics.

Systems

Bag System For Particle Filtration

In some embodiments of the present disclosure, high module density devices are housed in a filter cartridge and connected to tubing lines and bags to form a closed system. Such systems may be particularly useful for clinical applications, e.g. umbilical cord blood volume reduction, peripheral blood component separation, stem cell isolation from amniotic fluid, bone marrow filtration, leuko-reduction, plasma skimming, generation of stromal vascular fractions (SVF), etc. The particle sample being processed may not be exposed to outside contaminants. Further, the particle sample may be contained in the system, thereby reducing biohazard risks to the operator.

Figure 26A:
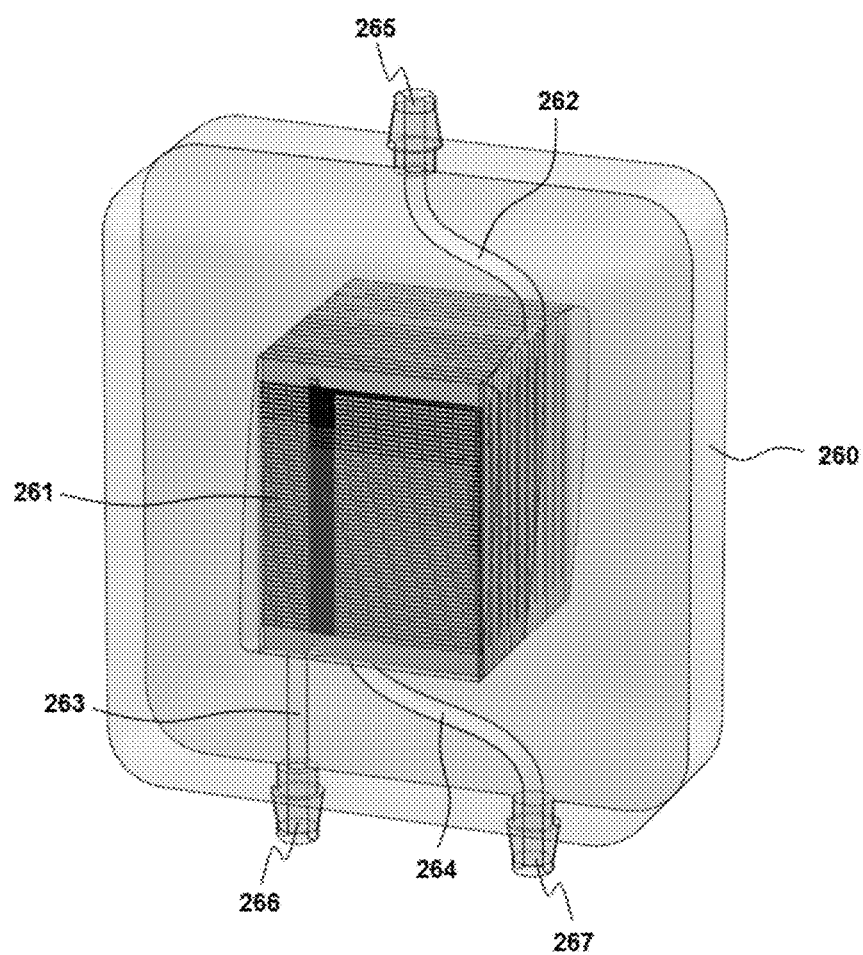
FIGS. 26A-26E are schematic diagrams of a cartridge.
Figure 26B:
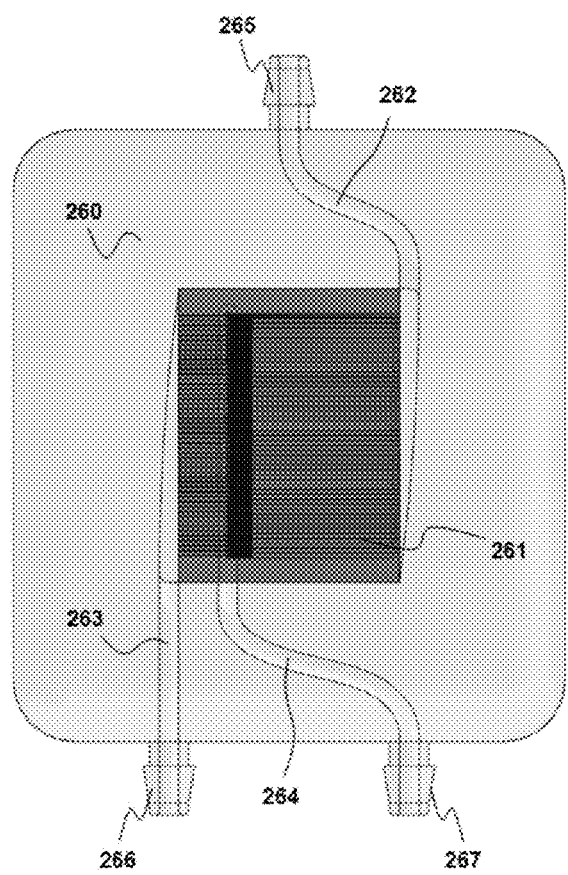
Figure 26C:
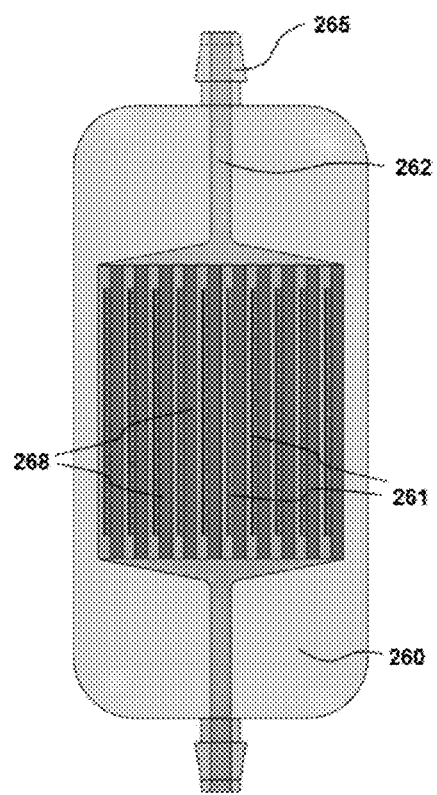
Figure 26D:
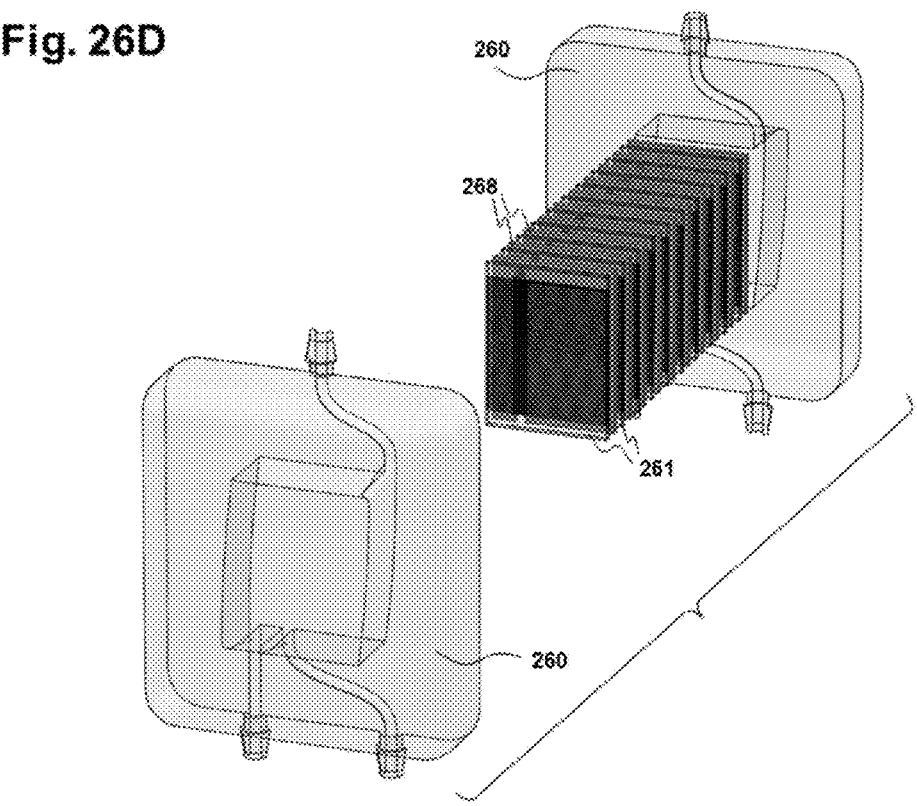
Figure 26E:
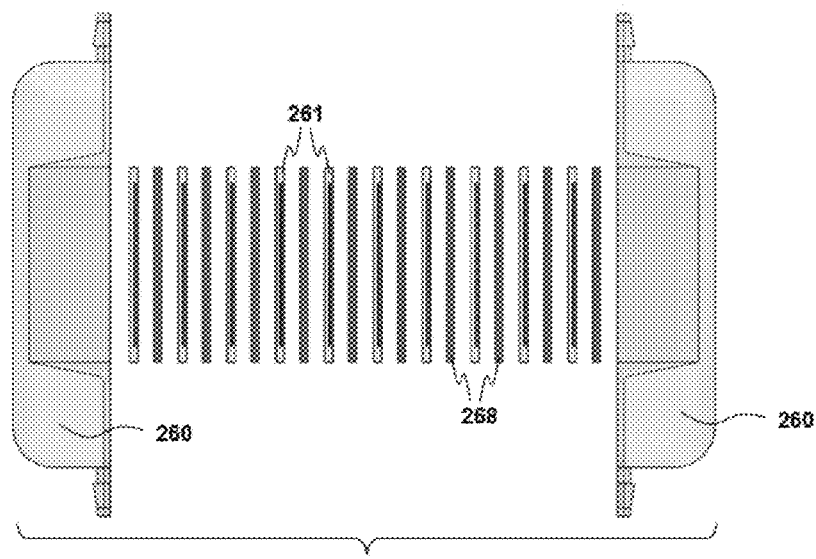

FIGS. 26A-26E show an embodiment of a filter cartridge comprising a housing 260 and multiple high module density devices 261. The housing 260 may comprise a feed channel 262, a retentate collection channel 263, and a filtrate collection channel 264. The channels may be connected to fittings 265, 266, 267 so that the cartridge can be connected to tubing to form a bag system. The cartridge 260 may distribute the feed across the high module density devices 261 so that the devices can process the feed in parallel to achieve high volumetric throughput. The cartridge 260 may also collect the retentate and filtrate from the high module density devices 261. As shown in FIGS. 26D and 26E, multiple high module density devices 261 may be stacked using gaskets 268 to provide proper seal so that the feed, retentate and filtrate are not cross contaminated. Alternatively, the high module density devices 261 may be glued or bonded.

The different parts of the filter cartridge can be glued, bonded, ultrasound bonded, clipped, or screwed together. The housing of the cartridge can be made of plastic using standard manufacturing techniques, such as injection molding, embossing, molding, hot embossing, stereo lithography, machining, etc. The plastic material for the housing may include, but not be limited to cyclic olefin copolymer (COC), cyclic olefin polymer (COP), polycarbonate, polyethylene, polypropylene, polymethylmethacrylate (PMMA), pressure sensitive materials, Teflon, acrylic, polyethersulfone, polytetrafluoroethylene, etc. The gaskets can be made of rubber materials such as silicone, latex, neoprene, vinyl rubber, using standard techniques such as die cutting, molding, waterjetting, etc.

Figure 27A:
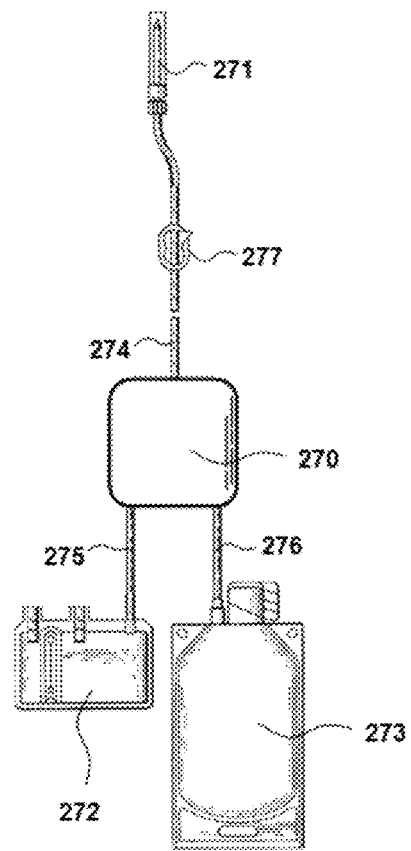
FIGS. 27A-27C are schematic diagrams of a bag system.
Figure 27B:
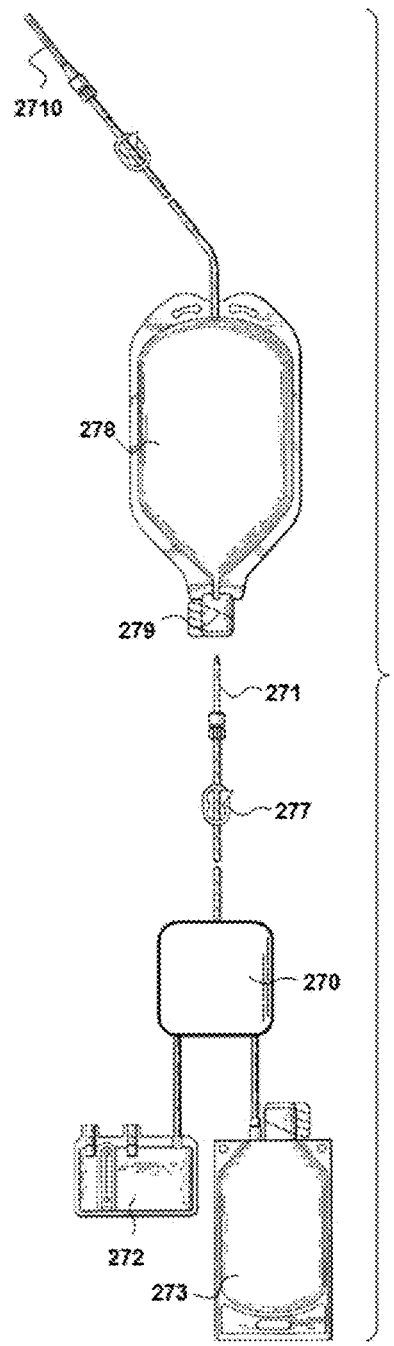
Figure 27C:
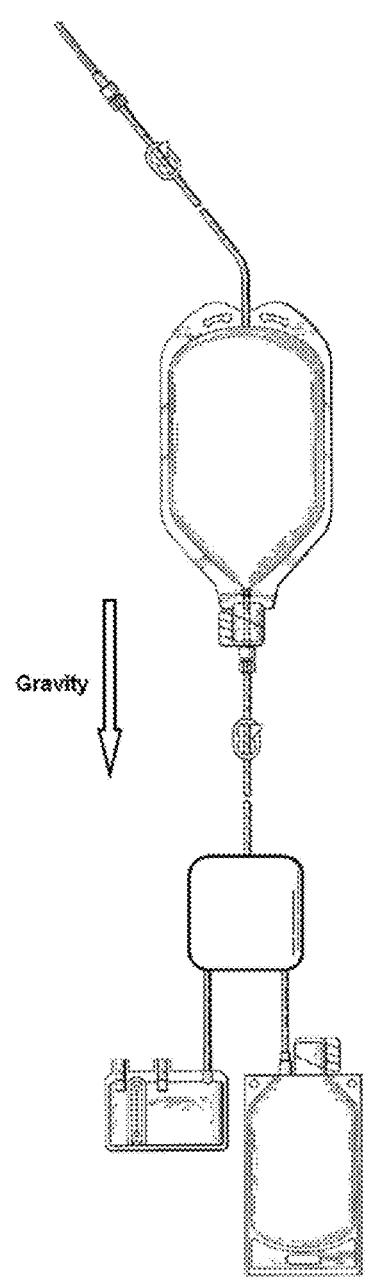

FIGS. 27A-27C show a bag system comprising a cartridge 270 comprising multiple high module density devices, a filtrate collection bag 273 and a retentate collection bag 272. The bags 272, 273 may be connected to the cartridge 270 using tubing 275, 276. The feed inlet of the cartridge 270 may be connected to an adaptor 271 using a tubing 274. The adaptor 271 may comprise a sike designed to penetrate a sample collection bag 278 at a port 279 (FIG. 27B), and allow feed particles in the sample collection bag 278 to enter the cartridge for filtration. The feed may comprise feed or particles described above, for example, blood, umbilical cord blood, peripheral blood stem cells, bone marrow, etc. After the adaptor 271 is plugged into the sample collection bag 278, the bag system may be hung under gravity (FIG. 27C), which may drive the feed through the high module density devices. Alternatively, a pressure can be applied to squeeze the sample bag 278 to drive the sample through the filter cartridge 270. Alternatively, a peristaltic pump can be applied to pump the fluids. The sample collection bag 278 can further comprise a needle 2710 to facilitate sample collection from a sample source, such as a patient or an umbilical cord.

The volumetric capacity of the bags may depend on the specific application the system is designed for. For umbilical cord blood banking purposes, umbilical cord blood is collected from an umbilical cord. The sample bag 278 may be capable of accommodating a range of about 20 ml to about 250 ml of umbilical cord blood, plus a range of about 0 ml to about 400 ml of anticoagulant or additives. Citrate phosphate dextrose (CPD) and heparin may be used as anticoagulants for umbilical cord blood collection. Additives may comprise phosphate buffered saline solution, Hank's balanced salt solution, a blood expander, a stem cell growth medium, growth factors etc. The anticoagulant or additives can be preloaded in the sample collection bag 278. In one embodiment of the present disclosure, a sample collection bag for umbilical cord blood may contain about 25 ml to 35 ml of CPD and may have the capacity to collect up to about 200 ml of umbilical cord blood.

In umbilical cord blood banking, umbilical cord blood may be processed to reduce the blood volume before freezing. This practice may reduce the long term storage cost. A bag system embodiment of the present disclosure can be used for umbilical cord blood volume reduction, where the bag system comprises high module density devices designed to separate red blood cells and plasma from retentate. The retentate may comprise hematopoeitic stem cells, progenitor cells, colony forming cells, and CD34+ cells. The retentate may be mixed with a freezing medium, e.g. dimethyl sulfoxide (DMSO), and may be frozen under cryopreservation conditions for later therapeutic use. The retentate collection bag 272 may comprise a cryopreservation freezing bag. In another embodiment of the present disclosure, the retentate collection bag may comprise a cryopreservation freezing bag comprising at least 2 compartments. In yet another embodiment of the present disclosure, the retentate collection bag may comprise a cryopreservation freezing bag with a capacity of 25 ml.

A bag system can further comprise a line clamp 277 on the feed tubing, retentate tubing, or filtrate tubing to control fluid flow in the bag system (FIG. 27).

Figure 28:
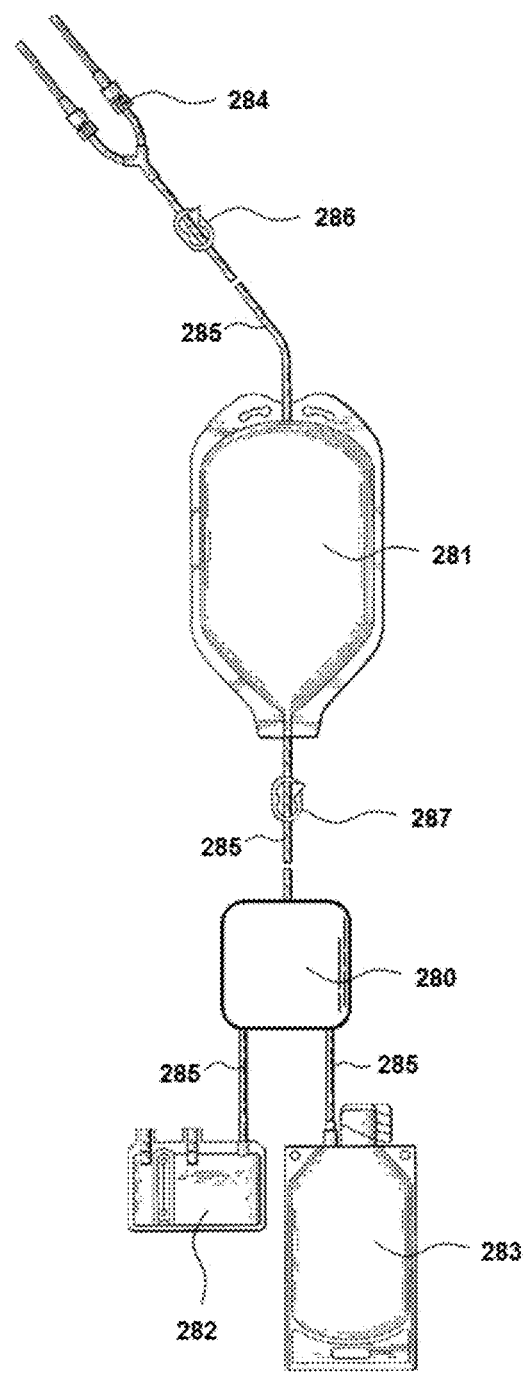
FIG. 28 is a schematic diagram of a bag system.

In another embodiment of the present disclosure, a sample collection bag 281 may be connected to a filter cartridge 280 using a tubing line 285 (FIG. 28). The system may further comprise a line clamp 287, which initially may be in a closed position. Sample, e.g. blood, umbilical cord blood, bone marrow, etc. may be collected using a needle 284 from a source, e.g. a patient, an umbilical cord, etc. The system optionally comprises a second needle, which may be used when the first needle is clogged. After the sample collection is completed, the line clamp 287 may be switched to the open position to allow liquid connection between the sample bag 281 and the filter cartridge 280. The sample may be driven by a driving force, such as gravity, a pressure, or a peristaltic pump.

Tube System for Particle Filtration

Figure 30A:
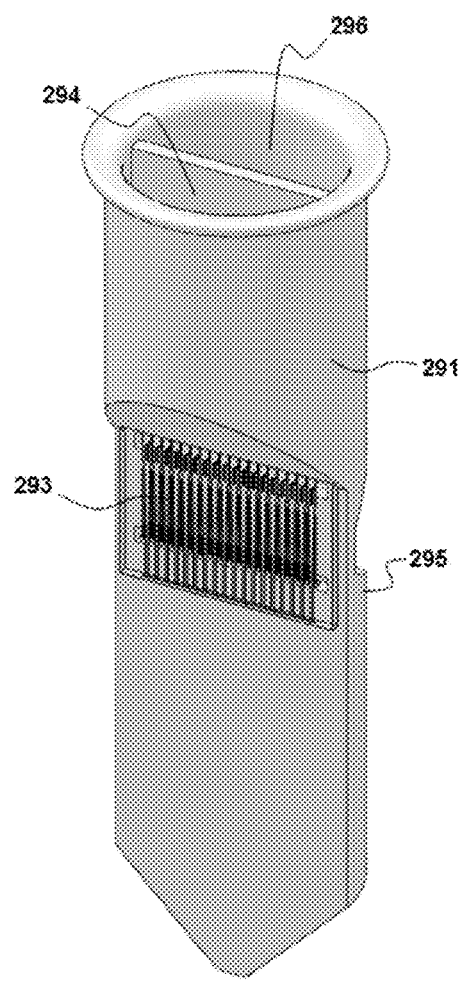
Figure 30B:
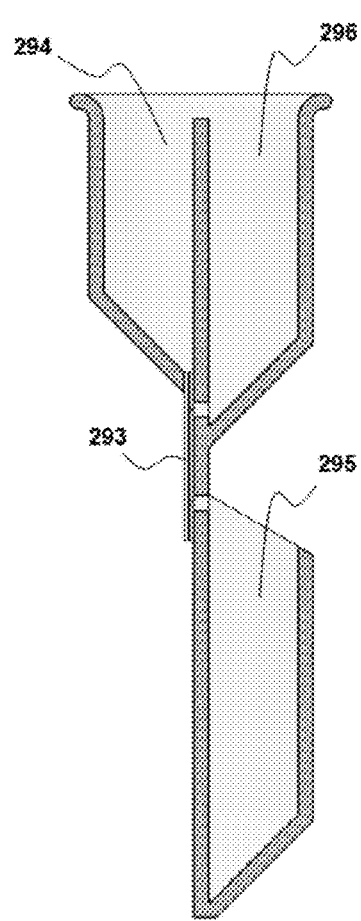

In another embodiment of the present disclosure, a high module density device may be incorporated in a tube system for sample filtration. The tube system may comprise a centrifuge tube 290, a tube insert 291, and a cap 292 (FIG. 29). The tube insert 291 may comprise a high module density device 293, a feed sample reservoir 294, an output reservoir 295, and optionally a carrier fluid reservoir 296 (FIG. 30). The output reservoir may be designed to contain the filtrate or retentate from the high module density device 293.

To use the tube system, a feed sample may be added to the feed sample reservoir. Optionally, a carrier fluid may be added to the carrier fluid reservoir. The carrier fluid may be marketed together with the tube system as a kit. The carrier fluid may be degassed to reduce the risk of bubble formation in the high module density device, or pre-packaged in a bottle under vacuum, i.e. at a pressure in a range of from about 0.05 atm to about 0.95 atm. Alternatively, the carrier fluid may be preloaded in s tube insert that is sealed using a foil, e.g. an aluminum foil.

The high module density device may separate a feed sample into two fractions. One fraction may be collected in the tube (290 in FIG. 29), and the other fraction may be collected in the tube insert. In one embodiment, the retentate may be collected in the tube. In another embodiment, the filtrate may be collected in the tube. In yet another embodiment, feed samples may be fractionated into three or more factions. Two or more output factions may be collected using the insert.

To operate the tube system (FIG. 29), the tube insert 291 may be inserted in the tube 290. A carrier fluid and a feed sample may be added to the carrier fluid and sample reservoirs respectively. The cap 292 may then put on to close the tube. The tube system can be driven by gravity. Alternatively, the tube system may be driven by centrifugal force, i.e. the assembled tube system may be spun in a centrifuge. The tube in the system can be a standard off-the-shelf centrifuge tube, e.g. a 50 ml, 15 ml, or 10 ml centrifuge tube, a standard off-the-shelf micro-centrifuge tube, e.g. a 2 ml, 1.5 ml, or 1 ml micro-centrifuge tube, or a non-standard custom made tube of any desired size.

Cartridge System and Plate System for Particle Filtration

In another embodiment of the present disclosure, a filtration device may be connected to wells to form a cartridge for sample filtration. The cartridge may comprise a filtration device and wells or reservoirs to accommodate a feed sample, retentate, filtrate, or carrier fluid. The cartridge may comprise multiple filtration devices and multiple sets of reservoirs to facilitate filtration of multiple samples. The reservoirs in the cartridge may be sealed with film, e.g., a plastic film, an aluminum film, etc.

In other embodiments of the present disclosure, a filtration device may be connected to wells to form a plate system for sample filtration. The system may comprise a filtration device and wells to accommodate the input and output fluids. The filtration device may comprise a filter module, a dual filter module, a filter cascade module, a multiple filter module, a high module density device, or any filter configuration disclosed in the present disclosure.

Figure 31A:
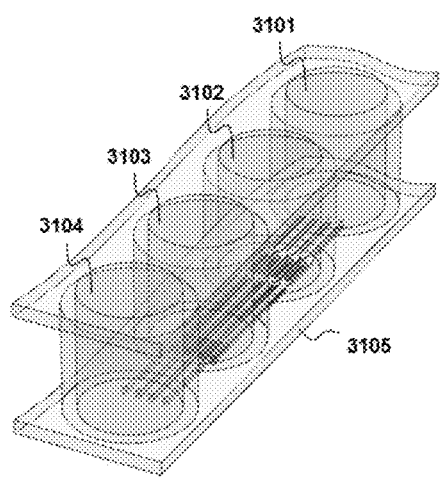
FIGS. 31A-31C are schematic diagrams of a plate system.
Figure 31B:
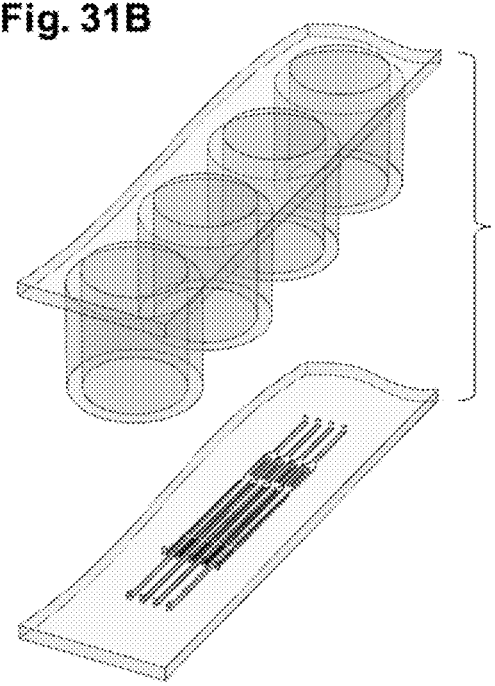
Figure 31C:
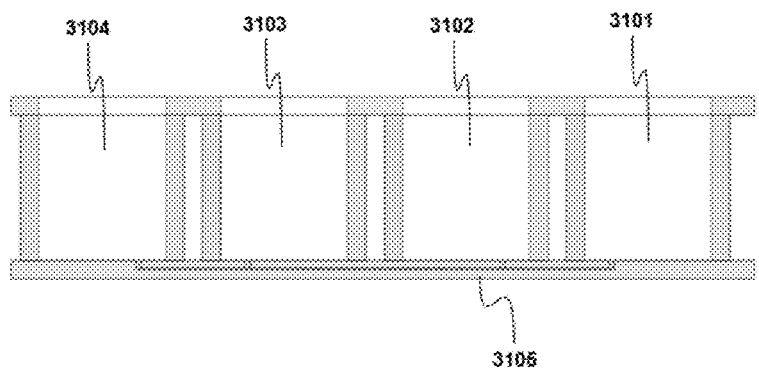
Figure 32A:
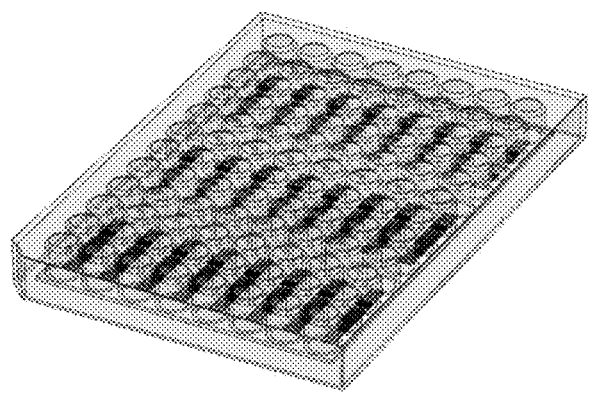
FIGS. 32A-32D are schematic diagrams of a plate system.
Figure 32B:
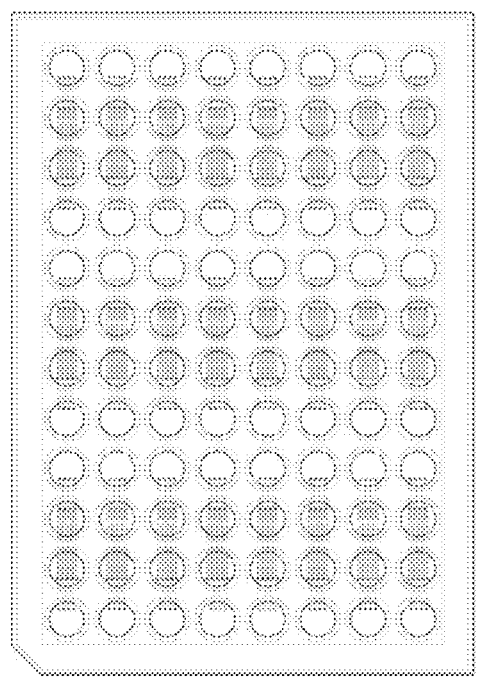
Figure 32C:
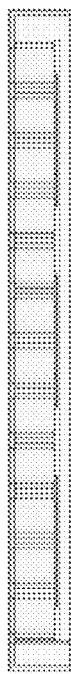
Figure 32D:

FIGS. 31A-31C show a plate system embodiment of the present disclosure, comprising a high module density device 3105, a sample well 3101, a carrier fluid well 3102, a filtrate well 3103 and a retentate well 3104. To use the system, a feed sample and a carrier fluid may be loaded into the sample well 3101 and the carrier fluid well 3102 respectively. A pressure may then be applied to the sample well 3101 and the carrier fluid well 3102 to drive the fluids through the filtration devices 3105. Alternatively, a mild vacuum may be applied to the filtrate well 3103 and the retentate well 3104 to drive the fluids. The filtrate and retentate may be collected in a filtrate well 3103 and a retentate well 3104 respectively.

A plurality of plate systems as disclosed above can be made in parallel as one plate system. FIGS. 32A-32D show a 96 well plate system embodiment of the present disclosure, comprising multiple high module density devices and 96 wells in a 96 well plate format. This system may have the advantage of using a standard 96 well plate format, and can be integrated into a standard workflow using standard pipetting and processing robots or workstations. This system may have the further advantage of processing multiple samples in one system, either simultaneously or consecutively. Alternatively, a plate system can be designed and made into other standard plate formats, e.g. a 6 well plate, a 384 well plate, etc. Further, a plate system can be designed and made into other non-standard plate formats without deviating from the spirit of the present disclosure.

The particles and fluids involved in the cartridge system or the plate system may be transferred manually or using an automated instrument, such as a pipetting robot.

Other System Formats for Particle Filtration

Other system of different formats can be designed and made without deviating from the spirit of the present disclosure. For example, filtration devices can be integrated with reservoirs and dispensing tips to dispense filtrate, retentate and optionally other fractions into test tubes or multi-well plates. In another embodiment of the present disclosure, a device is connected to vacutainers.

System Manufacturing Techniques

In accordance with some embodiments systems as described above can be made in plastic using standard manufacturing techniques, such as injection molding, embossing, molding, hot embossing, stereo lithography, etc. The plastic material for the housing may include, for example, polydimethylsiloxane (PDMS), cyclic olefin copolymer (COC), cyclic olefin polymer (COP), polycarbonate, polyethylene, polypropylene, polymethylmethacrylate (PMMA), pressure sensitive materials, Teflon, acrylic, polyethersulfone, polytetrafluoroethylene, etc. The systems may be sterilized using standard sterilization techniques, e.g. gamma irradiation, ethylene oxide (EO) sterilization, ultra violet light illumination, etc.

Operation of Devices and Systems

In various aspects and embodiments of the present disclosure, particles and fluids may be driven through a device or system using a fluid flow, a driving pressure, a vacuum, a head height, gravity, a centrifugal force, a magnetic force, a capillary action, an electric field, an electrophoretic field, an dielectrophoretic field, an electro-osmotic force, an electrokinetic force, or a combination of the above forces. Further, for a device or a system comprising a flexible bag, a driving pressure may be created by applying a pressure on the bag. For example, a bag may be sandwiched between two rigid plates. A pressure within the bag can be created and controlled by controlling the spacing between the plates or pressure exerted on the plates.

Particles and fluids may also be driven or transferred using one or more pumps, peristaltic pumps, syringe pumps, a centrifuge, or a combination of the above, and controlled using one or more valves or line clamps, e.g., pinch valves, check valves, vent valves, line clamps, etc. Further, the particles and fluids may also be transferred within a closed system, in an open system, using pipettes, using pipetting robots, using the suction of one or more vacutainers, or a combination of the above.

Aspects and embodiments of devices and systems of the present disclosure may also be operated with temperature control. Temperature control, e.g. heating elements, cooling elements, and thermometer components, can be incorporated into a device or system for the purpose of increasing the reproducibility of the filtration process or optimizing the filtration process. For example, in stromal vascular fractions (SVF) preparation, it may be advantageous to set the temperature of the device to between about 25 C and about 37 C to reduce the viscosity of the fluids being processed.

Packaging and Kits

In another embodiment of the present disclosure, a device or system may be preloaded or prefilled with reagents, e.g. carrier fluids. In yet another embodiment of the present disclosure, a device or system may be packaged with reagents, a user's manual, instructions, labels, operating protocols, data worksheets, disposable parts, collection tubes, pipette tips, transfer pipettes, vacutainers, test strips, biochips, lateral flow test strips, a cell counting chamber, a hemacytometer, and/or other devices to form a kit. Several devices or systems may be packaged and marketed as one kit. In another embodiment of the present disclosure, s device, system or kit may be sterilized. In yet another embodiment of the present disclosure, s device or system may individually packaged for extra sterility benefits.

It is understood that the various embodiments described herein are by way of example only, and are not intended to limit the scope of the disclosure. Various modifications, combinations, and variations of the described method and device of the disclosure will be apparent to those skilled in the art without departing from the scope and spirit of the disclosure. For example, many of the materials and structures described herein may be substituted with other materials and structures without deviating from the spirit of the disclosure. Further, a fluid flow described herein may be substituted with an electric field, an electrophoretic field, and electrokinetic flow, gravity, or a centrifugal force. It is also understood that the various theories and explanations described herein are not intended to be limiting. For example, the embodiments described herein may employ a fluid flow, a pressure drop, a hydrodynamic pressure, a pressure source, a vacuum, a head height, gravity, a centrifugal force, an electric field, an electrophoretic field, an electrokinetic force, or a combination of the above to drive the particles, without deviating from the spirit of the disclosure.

It is appreciated that while the filters in many of the embodiments described herein comprise pillars and pores, other filter designs comprising pores that use flow exclusion or other non-size-exclusion filtration mechanisms may be employed without deviating from the spirit of the disclosure. It is also appreciated that the embodiments of the present disclosure may be combined with other components or processes to form a more complicated device, system, or instrument.

EXAMPLES

Example 1

Polymer microsphere separation and measurement of retention size

Fluorescent polymer microspheres of 3.0 μm and 6.9 μm diameter were separated using a device comprising a dual filter module such as is illustrated in FIG. 14B. The dual filter module comprised channels and chambers 30 μm deep, and two filters comprising 165 pillars each. The pillars were 30 μm tall and 12 μm apart, thereby creating pores having physical pore sizes of 12 μm. The retentate chamber and filtrate chamber were designed such that the flow rate through a pore was between about 0.22% and about 0.28% of the flow rate at the retentate chamber inlet. The dual filter module was about 4 mm long and 0.25 mm wide.

The device was fabricated in silicon using standard microfabrication techniques. Photolithography and deep silicon reactive etching were used to create the fluidic channels, chambers, and filter structures. The etch depth was 30 μm. The silicon substrate was sealed on the etched channel face to a glass wafer to form enclosed fluidic channels using anodic bonding. The bonded wafer was then diced into individual devices. The device was mechanically mated to a plastic enclosure with external fluidic reservoirs to deliver sample fluids.

The sample fluid comprised fluorescent polymer microspheres of 3.0 μm and 6.9 μm diameter suspended in Dulbecco's phosphate-buffered salt solution containing 1% bovine serum albumin. The density of the microspheres was 1.05 g/cm$^3$. The volumetric concentrations of the 3.0 μm and 6.9 μm microspheres in the sample fluid were 0.00004% and 0.00048% respectively, which were about 28 microspheres each per μl. At such concentrations, particle-particle interactions are negligible.

The device was mounted on a fluorescence microscope to visualize the fluorescent polymer microspheres. A carrier fluid was added to the carrier fluid reservoir in the plastic enclosure to prime the device. The carrier fluid comprised Dulbecco's phosphate-buffered salt solution containing 1% bovine serum albumin. The sample fluid was subsequently added to the sample reservoir. Both reservoirs were then raised above the level of the retentate and filtrate reservoirs to create a head height of about 30 cm. The fluids were driven through the device by gravity and the head height. The average flow speed in the dual filter module was about 1.5 cm/s, corresponding to a Reynold's number in the chambers of about 0.45. The channel depth was used as the characteristic length in the calculation of the Reynold's number. The flow is laminar at such a Reynold's number.

The fluorescent polymer microspheres flowing through the device were manually counted as they departed the dual filter module. The results are shown as follows:

| Microsphere Diameter | Retained | Not Retained | Retention Rate |
| --- | --- | --- | --- |
| 3.0 μm | 0 | 20 | 0% |
| 6.9 μm | 258 | 3 | 99% |

The 3.0 μm microspheres represents the baseline where little retention occurs, and has a retention rate of about 0%. The retention rate for the 6.9 μm microspheres is about 99%, which is substantially higher than the baseline established by the 3.0 μm microspheres. The "retention size" of the dual filter module is therefore determined to be in the range of 3.0 μm to 6.9 μm, which is <58% of the physical pore size of 12 μm. For the dual filter module to have such a retention size, the "effective pore size" of the constituting pores must be no greater than 6.9 μm. The exemplary device herein has an effective pore size of <58% of the physical pore size.

It is appreciated that the exemplary method of using polymer microspheres to measure the retention size and the effective pore size may be applied to other filtration devices as a standard test for characterizing the retention sizes, regardless of the intended use of the filtration devices. For example, the devices used in Examples 2, 3, 4 and 5 below can be characterized using polymer microspheres, even though the devices were intended for cell processing.

Example 2

Isolation of Leukocytes from Whole Peripheral Blood

Leukocytes were isolated from whole peripheral blood using a high module density device.

Figure 24B:
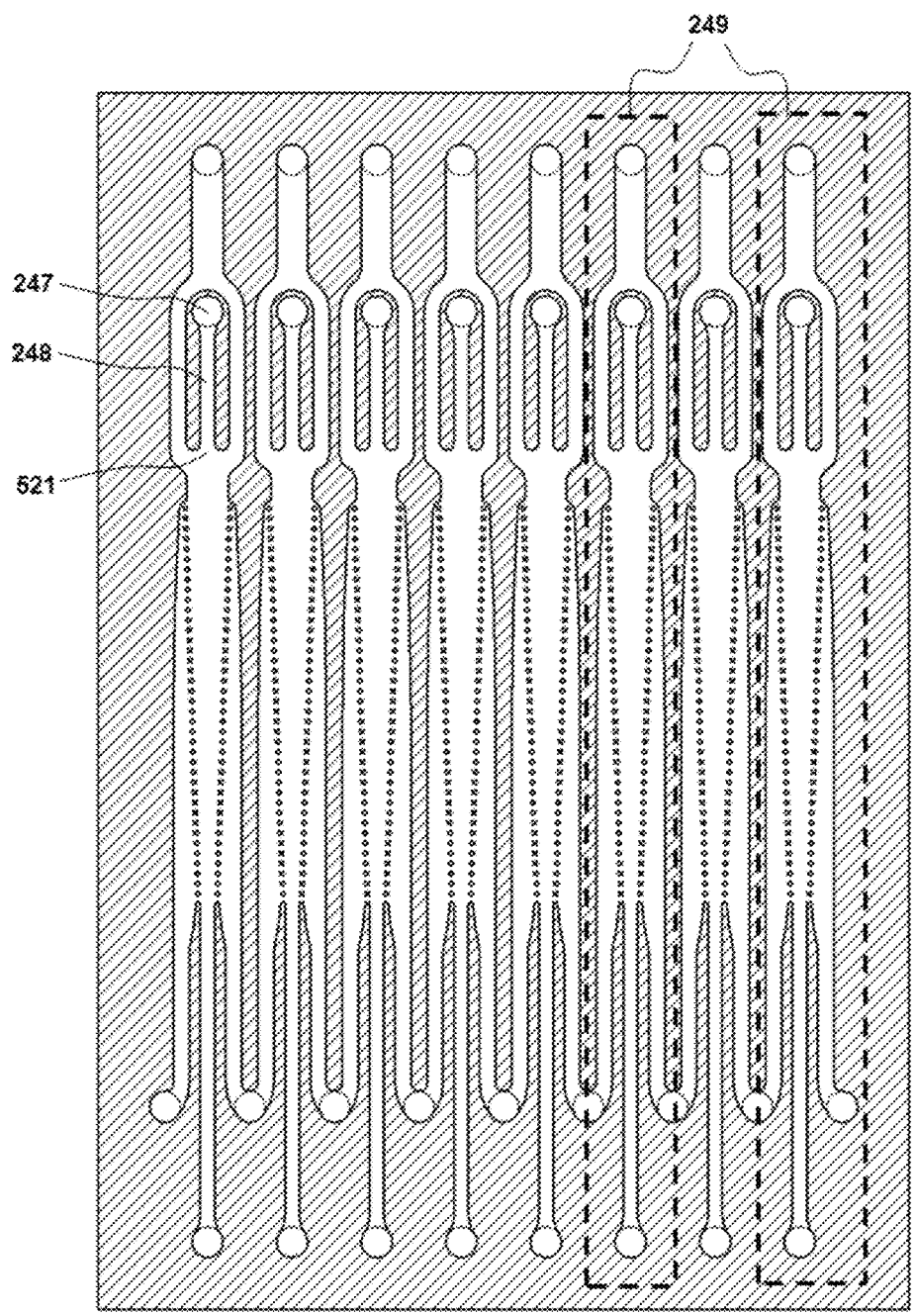
Figure 24C:
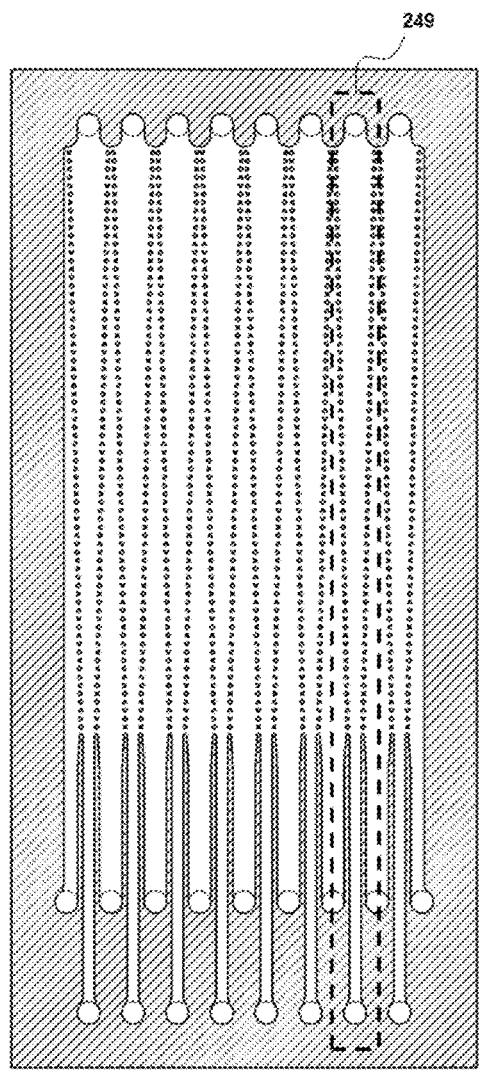
Figure 24D:
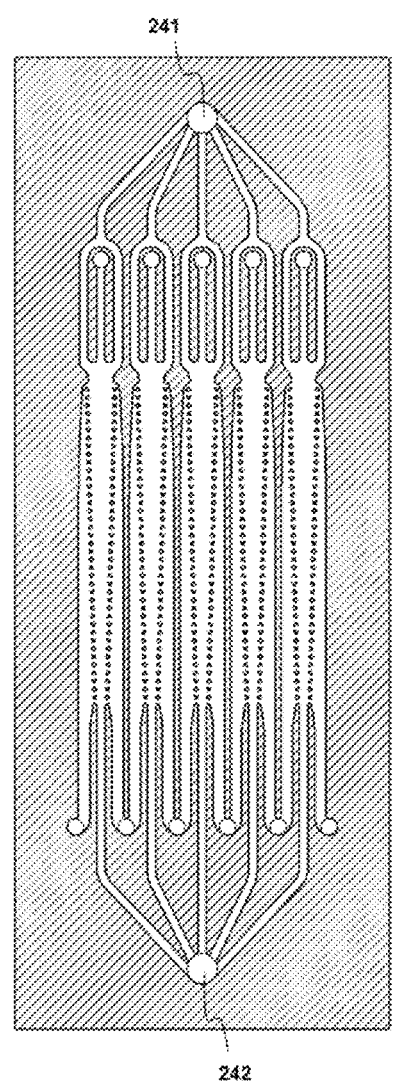
Figure 24E:
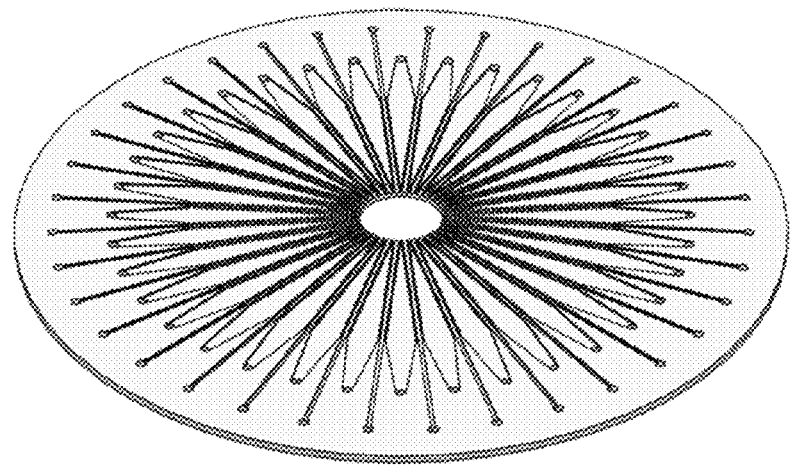

The exemplary device was a high module density device such as is illustrated in FIG. 24B comprising 72 filtration units (249 in FIG. 24B) each comprising a dual filter module, a carrier fluid input port (247 in FIG. 24B), a sample input port, a retentate output port, two filtrate output ports, and channels connecting the dual filter module and ports. The channels and chambers in the device were 30 μm deep. The dual filter modules each comprised 2 filters comprising 240 pores each. Each pore had a cross section of 30 μm×12 μm, thereby having a physical pore size of 12 μm. The retentate chambers and filtrate chambers of the dual filter modules were designed such that the flow rate through a pore was between about 0.12% and about 0.18% of the flow rate at the inlet of the retentate chamber. The device was 25 mm long, 24 mm wide, 0.6 mm thick, and had a footprint of 600 mm² (25 mm×24 mm).

Using the method described in Example 1, the effective pore size and the retention size was measured. It was estimated that the retention size of the device was about 4 μm, which is significantly smaller than the physical pore size of 12 μm.

The device was fabricated in silicon using standard microfabrication techniques. Photolithography and deep silicon reactive etching were used to create the fluidic channels, chambers, and filter structures. The etch depth was 30 μm. The silicon substrate was sealed on the etched channel face to a glass wafer to form enclosed fluidic channels using anodic bonding. The bonded wafer was then diced into individual devices. The device was mechanically mated to a plastic enclosure comprising external sample, carrier fluid, retentate, and filtrate reservoirs.

Human whole peripheral blood was used for samples in this example. The blood was drawn from consenting adult donors using $K_2$EDTA, ACD, or heparin vacutainers (Becton Dickinson, Franklin Lakes, N.J.). The hematocrits of the blood samples were about 40%. The bloods contained greater than 4 billion erythrocytes per ml. The hematocrit is the proportion of blood volume that is occupied by red blood cells. The blood was processed at room temperature within six hours from draw. Dulbecco's phosphate buffered saline solution containing 0.5% bovine serum albumin and 2 mM $K_2$EDTA was used as the carrier fluid.

8 ml of the carrier fluid was added to the carrier fluid reservoir in the plastic enclosure to prime the device. 4 ml of whole blood was subsequently added to the sample reservoir. Both reservoirs were then raised above the level of the retentate and filtrate reservoirs to create a head height of about 40 cm. The blood and the carrier fluid were driven through the device by gravity and the head height. The filtrate and the retentate were collected in the filtrate and retentate reservoirs respectively. After about 40 minutes, the blood was completely processed through the device. The filtrate and the retentate were then measured and analyzed using an automated cell counter (Coulter AcT diff hematology analyzer, Beckman Coulter, Fullerton, Calif.). The viability of the isolated leukocytes was measured immediately after the run, using propidium iodide, a stain that permeated cells with compromised membranes, a hemacytometer, and a fluorescence microscope.

The resulting retentate and filtrate volumes were about 3.5 ml and 7.6 ml respectively. Leukocytes were collected in the carrier fluid as the retentate. This experiment was performed twice, using blood samples from two different donors. The results are shown in FIG. 33. On average, the whole blood processing throughput was about 5.4 ml/hr. The device demonstrated the capability to process over 6 million cells per second. The leukocyte retention was about 94%, the erythrocyte carryover was about 2%, and the platelet carryover was <1%. Here, the erythrocyte carryover and the platelet carryover refer to the retention rates of erythrocytes and platelets, respectively. The leukocyte viability after processing was indistinguishable within the measurement error from that before processing. The measurements showed that the device and the isolation process do not reduce leukocyte viability, and that the device is able to isolate leukocytes with >99% viability.

The performance and cost efficiency metrics are shown below. The hold up volume of a filtration module in the exemplary device was about 0.03 μl. Each filtration unit comprised 480 pillars, and occupied a footprint of less than 8.4 mm² (i.e. a device footprint of 25 mm×24 mm divided by 72 filtration units). With a channel depth of 30 μm, a device footprint of 600 mm² (25 mm×24 mm), and 72 filtration units on the device, the "filtration unit density" of the device was therefore $$\text{Filtration Unit Density} = \frac{72}{600 \text{ mm}^2 \times 0.03 \text{ mm}^2} = 4,000 \text{ filtration units per cm}^3$$

The "normalized processing speed" of the exemplary device is calculated as follows:

$$\text{Normalized processing speed} = \frac{6 \times 10^6 \text{ s}^{-1}}{(25 \text{ mm} \times 24 \text{ mm}) \times (0.03 \text{ mm})} = 0.33 \times 10^6 \text{ s}^{-1} \text{ mm}^{-3}$$

Such a "normalized processing speed" means that every cubic millimeter of channel and filter structure on this device contributes to processing $0.33 \times 10^6$ cells per second.

The design efficiency index of the exemplary device is calculated below.

Feed processing throughput: Q=5.4 ml/hr=1.5 mm³/s

Characteristic channel depth: D=30 μm=0.03 mm

Device footprint: A=25 mm×24 mm=600 mm²

Retention size: R=4 μm=0.004 mm

Shear rate: S=1900 s⁻¹ (calculated below)

The maximum shear rate that a feed blood cell may experience in the device occurs at the surface of the feed inlet channel, according to computer modeling. The maximum shear rate can be calculated using computer fluid dynamics, or can be estimated analytically as follows assuming that the flow profile is parabolic in the feed inlet channel. From the fact that the device contains 144 feed inlet channels (2 per module, 72 modules) and that each inlet channel has a known cross section of 70 μm×30 μm, the average flow velocity $\langle v \rangle$ in the feed inlet channel is calculated to be $$\langle v \rangle = \frac{1.5 \text{ mm}^3/\text{s}}{144 \times (70 \text{ μm} \times 30 \text{ μm})} = 5.0 \text{ mm/s}$$

The shear rate at the surface of the feed inlet channel assuming a parabolic flow profile is therefore $$S \approx 6 \times \frac{\langle v \rangle}{30 \text{ μm}} \cong 1000 \text{ s}^{-1}$$

The design efficiency index (D.E.I.) of the exemplary device is therefore $$D.E.I. = \frac{Q}{ADSR^2}$$

$$\approx \frac{1.5 \text{ mm}^3/\text{s}}{600 \text{ mm}^2 \times 0.03 \text{ mm} \times 1000 \text{ s}^{-1} \times (0.004 \text{ mm})^2}$$

$$= 5.2 \text{ mm}^{-2}$$

Similarly, the design efficiency index (D.E.I.) of a filtration unit of the exemplary device may be calculated. Because there were 72 filtration units on the device, each filtration unit contributed to a feed processing throughput of 0.0208 mm³/s (1.5 mm³/s divided by 72). The average footprint of a filtration unit is 8.33 mm² (25 mm×24 mm=72). The design efficiency index (D.E.I.) of a filtration unit is therefore $$D.E.I. = \frac{Q}{ADSR^2}$$

$$\approx \frac{0.0208 \text{ mm}^3/\text{s}}{8.33 \text{ mm}^2 \times 0.03 \text{ mm} \times 1000 \text{ s}^{-1} \times (0.004 \text{ mm})^2}$$

$$= 5.2 \text{ mm}^{-2}$$

Despite that the device has a much higher processing throughput than a single filtration unit, the design efficiency index for the filtration unit is exactly the same as that of the device. It is appreciated that much as polymer microspheres may be used as a standard test to measure the retention size of a device regardless of the intended use, the design efficiency index may be used as a standard characteristic of a device regardless of its channel sizes, operating flow rates, and retention sizes.

Example 3

Leukocyte Reduction of Whole Blood

The exemplary device in Example 2 may serve as a leukoreduction filter. The filtrate of the device contained only 6% or less of the leukocytes entering the device. Example 2 showed that the devices of the present disclosure can be used to reduce leukocytes from whole blood. Other device configurations, with or without a carrier fluids, may also be used as leukoreduction filters.

Example 4

Isolation of Lymphocytes from Peripheral Blood

Lymphocytes were isolated from peripheral blood using a high module density device.

The exemplary device was a high module density device comprising 87 filtration units each comprising a filter cascade module such as is illustrated in FIG. 17C. Each filter cascade module comprised a first dual filter module (element 171 in FIG. 17C) and a second dual filter module (element 172 in FIG. 17C) comprising a carrier fluid inlet (element 175 in FIG. 17C). The channels and chambers in the device were 30 µm deep. The first dual filter module comprised 2 filters comprising 116 pores each. Each pore had a cross section of 30 µm×12 µm, thereby having a physical pore size of 12 µm. The retentate chambers and filtrate chambers of the first dual filter module were designed such that the flow rate through a pore was about 0.29% of the flow rate at the inlet of the retentate chamber of the first dual filter module. The second dual filter module comprised 2 filters comprising 120 pores each. Each pore had a cross section of 30 µm×12 µm, thereby having a physical pore size of 12 µm. The retentate chambers and filtrate chambers of the second dual filter module were designed such that the flow rate through each pore was about 0.34% of the flow rate at the inlet of the retentate chamber of the second dual filter module. The device was 21 mm long, 24 mm wide, 0.6 mm thick, and had a footprint of 504 mm² (21 mm×24 mm).

The device was fabricated in silicon using standard microfabrication techniques. Photolithography and deep silicon reactive etching were used to create the fluidic channels, chambers, and filter structures. The etch depth was 30 µm. The silicon substrate was sealed on the etched channel face to a glass wafer to form enclosed fluidic channels using anodic bonding. The bonded wafer was then diced into individual devices. The device was mechanically mated to a plastic enclosure comprising external sample, carrier fluid, retentate, and filtrate reservoirs.

Human peripheral blood was used for samples in this example. The blood was drawn from consenting adult donors using $K_2$EDTA vacutainers (Becton Dickinson, Franklin Lakes, N.J.). The blood was diluted 1:1 with Hank's balanced salt solution and processed at room temperature within 8 hours from draw. Hank's balanced salt solution containing 0.5% bovine serum albumin and 2 mM $K_2$EDTA was used as the carrier fluid.

10 ml of the carrier fluid was added to the carrier fluid reservoir in the plastic enclosure to prime the device. 8 ml of blood sample was subsequently added to the sample reservoir. Both reservoirs were then raised above the level of the retentate and filtrate reservoirs to create a head height of about 45 cm. The blood and the carrier fluid were driven through the device by gravity and the head height. The filtrate and the retentate were collected in the filtrate and retentate reservoirs respectively. After about 40 min, the blood was completely processed through the device. The filtrate and the retentate were then measured and analyzed using an automated cell counter (Coulter AcT diff hematology analyzer, Beckman Coulter, Fullerton, Calif.), where lymphocytes, monocytes, granulocytes, erythrocytes, and platelets were differentially counted.

The 8 ml of blood sample and 10 ml of carrier fluid input resulted in about 5 ml of retentate and about 13 ml of filtrate. Lymphocytes were collected as the retentate in the carrier fluid. This experiment was performed twice, using blood samples from two different donors. The results are shown in FIGS. 34A-34D. The average processing throughput was 9.2 ml/hr, and the isolated lymphocyte purity was >90%, i.e. of all leukocytes in the retentate, >90% were lymphocytes. The erythrocyte carryover was <0.5%, and the platelet carryover was <1%. The diluted blood used here contained greater than 2 billion erythrocytes per ml. Therefore, the device demonstrated the capability to process over 5 million cells per second.

The exemplary device here demonstrated that each module can isolate lymphocytes with high efficiency and performance, and that many such modules can operate in parallel as a high module density device. Specifically, each filtration unit comprises 472 pillars, and occupied a footprint of less than 5.8 mm² (i.e. a device footprint of 21 mm×24 mm divided by 87 filtration units). The hold up volume of a filtration module in the exemplary device was about 0.015 µl. With a channel depth of 30 µm, a device footprint of 504 mm² (21 mm×24 mm), and 87 filtration units on the device, the "filtration unit density" of the device was therefore $$\text{Filtration Unit Density} = \frac{87}{504 \text{ mm}^2 \times 0.03 \text{ mm}^2}$$
$$\cong 5{,}750 \text{ filtration units per cm}^3$$

The "normalized processing speed" of the exemplary device index is calculated as follows:

$$\text{Normailized processing speed} = \frac{5 \times 10^6 \text{ s}^{-1}}{(21 \text{ mm} \times 24 \text{ mm}) \times (0.03 \text{ mm})}$$
$$= 0.33 \times 10^6 \text{ s}^{-1} \text{ mm}^{-3}$$

Such a "normalized processing speed" means that every cubic millimeter of channel and filter structure fabricated on this device contributes to processing 0.33 million cells per second.

This example epitomized the complex nature of flow exclusion in some aspects and embodiments of the present disclosure, and how flow exclusion could be used to isolate components from a complex fluid, such as the isolating lymphocytes from blood, in a manner that was not anticipated or obvious in light of previous disclosures to date. In particular, all major types of cells in the blood, i.e. erythrocytes, granulocytes, monocytes, and lymphocytes, were substantially smaller than the physical pore size of the device. The average cell diameters of erythrocytes, granulocytes, monocytes, and lymphocytes are approximately 7 µm, 8 µm, 6 µm, and 5 µm, respectively. Further, lymphocytes are the smallest components among the four major cell types, having an average cell volume of about 60 fl, compared to about 90 fl, 250 fl, and 120 fl for erythrocytes, granulocytes, and monocytes respectively. However, the lymphocytes were the only cell type that was substantially retained by the filters in the exemplary device, with a retention rate of about 60%, compared to the retention rates of about 0% for all other cell types (FIG. 34C).

This example also clearly demonstrated that the separation process in the exemplary application is stochastic, and the particle retention is best described using probability, i.e. a retention probability or a retention rate. In particular, the migration path of a blood cell may not be predetermined, at least not solely predetermined according to a critical size. Possible factors that might have affected the retention probability include cell interaction, Brownian motion, cell deformation, and perturbation of flow patterns.

Example 5

Volume Reduction of Human Umbilical Cord Blood and Enrichment of Hematopoietic Stem Cells with High Cell Viability The volume of umbilical cord blood was reduced while leukocytes, CD34+ cells, and colony forming stem cells and progenitor cells, including CFC-GM, were recovered with high cell viability using a high module density device.

The device used in this example was a high module density device comprising 87 filtration units each comprising a filter cascade module as illustrated in FIG. 17C. Each filter cascade module comprised a first dual filter module (element 171 in FIG. 17C) and a second dual filter module (element 172 in FIG. 17C). The channels and chambers in the device are 30 µm deep. The first dual filter module comprised 2 filters comprising 120 pores each. Each pore had a cross section of 30 µm×12 µm, thereby having a physical pore size of 12 µm. The retentate chambers and filtrate chambers of the first dual filter module were designed such that the flow rate through each pore was about 0.28% of the flow rate at the inlet of the retentate chamber of the first dual filter module. The second dual filter module comprised 2 filters comprising 320 pores each. Each pore had a cross section of 30 µm×12 µm, thereby having a physical pore size of 12 µm. The retentate chambers and filtrate chambers of the second dual filter module were designed such that the flow rate through a pore was between about 0.10% and about 0.14% of the flow rate at the inlet of the retentate chamber of the second dual filter module. The device was 23 mm long, 24 mm wide, 0.6 mm thick, and a footprint of 552 mm² (23 mm×24 mm)

It is estimated that the retention size of the device was about 4 µm, which is significantly smaller than the physical pore size of 12 µm.

The device was fabricated in silicon using standard microfabrication techniques. Photolithography and deep silicon reactive etching were used to create the fluidic channels, chambers, and filter structures. The etch depth was 30 µm. The silicon substrate was sealed on the etched channel face to a glass wafer to form enclosed fluidic channels using anodic bonding. The bonded wafer was then diced into individual devices. The device was mechanically mated to a plastic enclosure comprising external sample, retentate, and filtrate reservoirs.

Human umbilical cord blood was used for samples in this example. The blood was collected from consenting adult women using cord blood collection bags (Fenwal Inc., Round Lake, Ill.). The cord blood collection bags contained citrate phosphate dextrose (CPD) as an anticoagulant. The blood was processed at room temperature within 6 hours from draw.

12 ml of cord blood with no further dilution was added to the device. The hematocrits of the cord blood feeds were in the range of 19% to 45%, and in average contained 2.8 billion red blood cells per ml. The hematocrit is the proportion of blood volume that is occupied by red blood cells. The blood was driven through the device by gravity and a head height of about 40 cm. The filtrate and the retentate were collected in a filtrate reservoir and a retentate reservoir, respectively. Leukocytes, CD34+ cells, and colony forming stem cells and progenitor cells were expected to be recovered as the retentate. After about 1 hour, the blood was completely processed through the device. The filtrate and the retentate were then measured and analyzed using an automated cell counter (Coulter AcT diff hematology analyzer, Beckman Coulter, Fullerton, Calif.) to calculate the leukocyte recovery yield. The viability of the recovered cells was measured immediately after the run using propidium iodide, a stain that permeated cells with compromised membranes, a hemacytometer, and a fluorescence microscope. The CD34+ cell recovery was measured using flow cytometry. To count the colony forming cells, the cord blood and the retentate were mixed with an ammonium chloride lysis solution (Stemcell Technologies, Vancouver, BC, Canada) to lyse the red blood cells, washed, and then cultured in a methylcellulose growth medium (Stemcell Technologies, Vancouver, BC, Canada) for 14 days using an incubator set at 37 degrees Celsius, 5% $CO_2$, and high humidity. After 14 days, the CFC-GM colonies were counted manually using an inverted microscope.

Results of the experiments are shown in FIGS. 35A-35C. Leukocytes, CD34+ cells, and colony forming cells (e.g. CFC-GM) were recovered in the retentates with recovery yields of about 88%, 87% and 92% respectively. The device reduced the cord blood volume by a factor of about 5.4, i.e. the retentate volumes were about 18.5% of the cord blood feed volume. With such a volume reduction factor, 100 ml of cord blood would have been reduced to 18.5 ml. The cell viabilities before and after processing were substantially identical, well within the measurement error, and were >99%. The processing throughput was about 11.4 ml/hr in average. This throughput is equivalent to processing about 9 million cells per second.

The "normalized processing speed" of the exemplary device is calculated as follows:

$$\text{Normalized processing speed} = \frac{9 \times 10^6 \text{ s}^{-1}}{(23 \text{ mm} \times 24 \text{ mm}) \times (0.03 \text{ mm})}$$
$$= 0.54 \times 10^6 \text{ s}^{-1} \text{ mm}^{-3}$$

Every cubic millimeter of channel and filter structure fabricated on this exemplary device contributed to the processing of 0.54 million cells per second.

This example demonstrated that the device utilized could concentrate cord blood stem cells and progenitor cells with very good recovery yield and cell viability. Specifically, each filtration unit comprised 880 pillars, and occupied a footprint of less than 6.4 mm$^2$ (i.e. a device footprint of 23 mm×24 mm divided by 87 filtration units). The hold up volume of a filtration module in the exemplary device was about 0.04 μl. With a channel depth of 30 μm, a device footprint of 552 mm$^2$ (23 mm×24 mm), and 87 filtration units on the device, the "filtration unit density" of the device was therefore $$\text{Filtration Unit Density} = \frac{87}{552 \text{ mm}^2 \times 0.03 \text{ mm}^2}$$
$$\cong 5,250 \text{ filtration units per cm}^3$$

The design efficiency index of the utilized device is calculated below.

Feed processing throughput: Q=11.4 ml/hr=3.17 mm$^3$/s

Characteristic channel depth: D=30 μm=0.03 mm

Device footprint: A=23 mm×24 mm=552 mm$^2$

Retention size: R=4 μm=0.004 mm

Shear rate: S=1900 s$^{-1}$ (calculated below)

The maximum shear rate in the device occurs at the surface of the retentate chamber close to its inlet. The maximum shear rate can be calculated using computer fluid dynamics, or can be estimated analytically as follows assuming that the flow profile is parabolic in the retentate chamber. From the fact that the device contained 87 filtration modules and that each retentate chamber had a known cross section of 130 μm×30 μm at the inlet, the average flow velocity <v> in the retentate chamber at the inlet was calculated to be $$\langle v \rangle = \frac{3.17 \text{ mm}^3/\text{s}}{87 \times (130 \text{ μm} \times 30 \text{ μm})} = 9.34 \text{ mm/s}$$

The shear rate at the surface of the retentate chamber, assuming a parabolic flow profile was therefore $$S \approx 6 \times \frac{\langle v \rangle}{30 \text{ μm}} \cong 1900 \text{ s}^{-1}$$

The design efficiency index (D.E.I.) of the exemplary device is therefore $$D.E.I. = \frac{Q}{ADSR^2}$$
$$\approx \frac{3.17 \text{ mm}^3/\text{s}}{552 \text{ mm}^2 \times 0.03 \text{ mm} \times 1900 \text{ s}^{-1} \times (0.004 \text{ mm})^2}$$
$$= 6.3 \text{ mm}^{-2}$$

Example 6

Labeling Isolated Cells

The exemplary device in Example 2 may serve to label subpopulations of cells having at least one specific antigen, using a carrier fluid comprising antibodies against the at least one specific antigen. The antibody may be conjugated to a fluorophore or a magnetic bead to label target cells fluorescently or magnetically. During the separation process, retentate cells are directed from the feed stream into the carrier fluid stream, and mixed with the antibodies. Retentate cells having the specific antigen are labeled and collected as the retentate. Optionally a wash solution may be introduced in the filtration modules of the device in the same manner as the carrier flow, to wash the cells as they flow through the modules. The separation process may be performed at a temperature favorable for specific antibody labeling. Subsequently, fluorescently labeled cells may be counted and characterized using a flow cytometer, and magnetically labeled cells may be isolated using a magnet. Antibodies which may be used for labeling subpopulations of leukocytes and other cells present in the blood include, anti-CD45, anti-CD34, anti-CD71, anti-CD138, anti-CD14, anti-CD15, anti-CD3, anti-CD4, anti-CD8, anti-CD19, anti-HLA, anti-GPA, anti-CD271, anti-CD43, anti-CD10, anti-CD33, anti-CD66, and anti-CD105 antibodies. The carrier fluid may comprise other reagents than antibodies to label, treat, alter, stain, wash, or even lyse the retentate cells may also be performed in a similar fashion. Possible reagents that may be used as the carrier flow may include nucleic acid stains, fixatives, freezing solutions, alkylating agents, antibodies, magnetic beads, enzymes, collagenase, lipase, DNase, substrates of certain enzymes, active derivatives of cyclophosphamide, growth factors, detergents, and lysis solutions. This example illustrates the use of a filtration device of the present disclosure to perform separation and cell labeling, treatment, alteration, staining, washing, or lysis in one step. Such a method is expected to be very useful in many applications, including isolation of CD34+ stem cells, isolation of circulating tumor cells, preparation of stromal vascular fractions, counting CD4+ cells, isolation of malignant plasma cells, detecting aldehyde dehydrogenase activities, separation of specific cells based on enzyme activities, isolation of specific cells based on surface antigens.

Other Embodiments

From the foregoing description, it will be apparent that variations and modifications may be made to the disclosure described herein to adopt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. A filtration device including at least one filtration unit, the at least one filtration unit comprising:
   a first sidewall;
   a second sidewall;
   a first fluid inlet defined between the first sidewall and the second sidewall, the first fluid inlet configured to receive a feed comprising a particle population and a fluid;
   a first row of pillars;
   a first plurality of pores defined by spacings between adjacent pillars in the first row of pillars;
   a first flow chamber defined between the first row of pillars and the second sidewall and including a first flow chamber inlet and a first retentate outlet, the first flow chamber configured to direct a first retentate including at least a portion of the particle population to the first retentate outlet;
   a second flow chamber defined between the first row of pillars and the first sidewall and including a first filtrate outlet, the second flow chamber configured to direct a first filtrate including at least a portion of the fluid to the first filtrate outlet;
   wherein a distance between the first row of pillars and the first sidewall proximate the first flow chamber inlet is smaller than a distance between the first row of pillars and the first sidewall proximate the first retentate outlet;
   a second row of pillars;
   a second plurality of pores defined by spacings between adjacent pillars in the second row of pillars; and
   a third flow chamber defined between the second row of pillars and the second sidewall, the third flow chamber including a third flow chamber inlet configured to receive the first retentate and the first filtrate and a second retentate outlet, the third flow chamber being configured to direct at least a portion of the particle population to the second retentate outlet, a distance between the second row of pillars and the first sidewall proximate the third flow chamber inlet being smaller than a distance between the third row of pillars and the first sidewall proximate the second retentate outlet.

2. The filtration device of claim 1, including a plurality of filtration units.

3. The filtration device of claim 1, wherein each filtration unit further includes a second fluid inlet disposed substantially equidistant from the first sidewall and the second sidewall.

4. The filtration device of claim 1, wherein each filtration unit further includes a third row of pillars disposed between the first flow chamber and the second sidewall, a distance between the third row of pillars and the second sidewall proximate the first flow chamber inlet being smaller than a distance between the third row of pillars and the first sidewall proximate the first retentate outlet, the third row of pillars configured to direct at least a portion of the particle population to the first retentate outlet, and wherein each filtration unit further includes a fourth row of pillars disposed between the third flow chamber and the second sidewall, a distance between the fourth row of pillars and the second sidewall proximate the third flow chamber inlet being smaller than a distance between the fourth row of pillars and the first sidewall proximate the second retentate outlet.

5. The filtration device of claim 4, wherein each filtration unit is substantially symmetric about a center line defined substantially equidistant from the first sidewall and the second sidewall, and wherein the first physical pore size and the second physical pore size are substantially identical.

6. The filtration device of claim 4, wherein each of the first row of pillars and the third row of pillars includes an upstream end and a downstream end, a spacing between the downstream end of the first row of pillars and the downstream end of the third row of pillars defining the first retentate outlet, the third flow chamber inlet disposed downstream of the first retentate outlet.

7. The filtration device of claim 1, wherein the particle population is a cell population.

8. The filtration device of claim 1, wherein the particle population is stem cells.

9. The filtration device of claim 1, wherein the feed is blood.

10. The filtration device of claim 1, wherein the feed is umbilical cord blood.

11. The filtration device of claim 1, wherein the feed is a stromal vascular fraction.

12. The filtration device of claim 1, wherein:
   each of the first plurality of pores has an effective pore size smaller than a first physical pore size, the first physical pore size defined by the spacings between the adjacent pillars in the first row of pillars; and
   each of the second plurality of pores has an effective pore size smaller than a second physical pore size, the second physical pore size defined by the spacings between the adjacent pillars in the second row of pillars.

13. The filtration device of claim 12, wherein the effective pore size of the first plurality of pores of the first row of pillars is smaller than at least one particle in the particle population.

14. A filtration device including at least one filtration unit, the at least one filtration unit comprising:
   a first sidewall;
   a second sidewall;
   a first fluid inlet defined between the first sidewall and the second sidewall, the first fluid inlet configured to receive a feed comprising a particle population and a fluid;
   a first row of pillars including an upstream end and a downstream end;
   a first plurality of pores defined by spacings between adjacent pillars in the first row of pillars;
   wherein a distance between the first row of pillars and the first sidewall proximate the upstream end of the first row of pillars is smaller than a distance between the first row of pillars and the first sidewall proximate the downstream end of the first row of pillars, and a first filtrate flow chamber free of pillars is defined extending between the first row of pillars and the first sidewall;
   a second row of pillars disposed downstream of the upstream end of the first row of pillars; and a second plurality of pores defined by spacings between adjacent pillars in the second row of pillars;
wherein a distance between the second row of pillars and the second sidewall proximate the upstream end of the second row of pillars is smaller than a distance between the second row of pillars and the second sidewall proximate the downstream end of the second row of pillars, and a second filtrate flow chamber free of pillars is defined extending between the second row of pillars and the second sidewall.

15. The filtration device of claim 14, wherein each filtration unit further includes a second inlet disposed substantially equidistant from the first sidewall and the second sidewall.

16. The filtration device of claim 14, wherein:
each of the first plurality of pores has an effective pore size smaller than a first physical pore size, the first physical pore size defined by the spacings between the adjacent pillars in the first row of pillars; and
each of the second plurality of pores has an effective pore size smaller than a second physical pore size, the second physical pore size defined by the spacings between the adjacent pillars in the second row of pillars.

17. A filtration system comprising:
a fluid line configured to receive a liquid suspension of cells comprising a target cell population suspended in a fluid;
a first collection chamber;
a second collection chamber; and
at least one cartridge comprising:
a cartridge inlet,
a first cartridge outlet fluidically connected to the first collection chamber,
a second cartridge outlet fluidically connected to the second collection chamber, and
at least one filtration unit, the at least one filtration unit having:
a filtration unit inlet fluidically connected to the cartridge inlet,
a first filtration unit outlet fluidically connected to the first cartridge outlet,
a second filtration unit outlet fluidically connected to the second cartridge outlet, and
a flow chamber configured to separate the target cell population from at least a portion of the fluid, to direct the target cell population to the first filtration unit outlet, and to direct the at least a portion of the fluid to the second filtration unit outlet, the flow chamber including:
a first sidewall,
a second sidewall,
a flow chamber inlet,
a flow chamber outlet including a filtrate outlet and a retentate outlet,
a first row of pillars,
a first plurality of pores defined by spacings between adjacent pillars in the first row of pillars, a distance between the first row of pillars and the first sidewall proximate the flow chamber inlet being smaller than a distance between the first row of pillars and the first sidewall proximate the flow chamber outlet,
a second row of pillars, a distance between the second row of pillars and the second sidewall proximate the flow chamber inlet being smaller than a distance between the second row of pillars and the second sidewall proximate the flow chamber outlet, a downstream end of the first row of pillars and a downstream end of the second row of pillars defining the retentate outlet, the retentate outlet being in fluid communication with the first filtration unit outlet,
a first filtrate chamber free of pillars extending from the first row of pillars to the first sidewall and occupying the volume between the first row of pillars to the first sidewall, and
a second filtrate chamber free of pillars extending from the second row of pillars to the second sidewall and occupying the volume between the second row of pillars to the second sidewall,
the first collection chamber, the second collection chamber, and the at least one cartridge forming a closed system.

18. The filtration system of claim 17, wherein each filtration unit is substantially symmetric about a center line defined equidistant from the first sidewall and the second sidewall.

19. The filtration system of claim 17, wherein each filtration unit further includes:
a third row of pillars including an upstream end and a downstream end, a distance between the third row of pillars and the first sidewall proximate the upstream end of the third row of pillars being smaller than a distance between the third row of pillars and the first sidewall proximate the downstream end of the third row of pillars, the third row of pillars positioned downstream of the first row of pillars.

20. The filtration system of claim 17, including a plurality of filtration units disposed on a surface in a high module density device.

21. The filtration system of claim 17, comprising a plurality of high module density devices each including a plurality of filtration units.

22. The filtration system of claim 17, wherein the at least one filtration unit further includes at least one carrier fluid inlet distinct from the filtration unit inlet.

23. The filtration system of claim 17, wherein each of the first plurality of pores has an effective pore size smaller than a first physical pore size, the first physical pore size defined by the spacings between the adjacent pillars in the first row of pillars.

24. A method for cell processing comprising:
introducing a feed sample comprising a viable target cell population and a nonviable cell population suspended in a fluid to the fluid line of the filtration system of claim 17;
driving the feed sample through the filtration system;
collecting the viable target cell population in the first collection chamber; and
collecting the portion of the nonviable cell population and the portion of the fluid in the second collection chamber.

25. The method of claim 24, wherein the filtration system includes at least one high module density device including a plurality of the at least one filtration units, the plurality of the at least one filtration units disposed on a surface of the at least one high module density device.

26. The method of claim 24, wherein driving the feed sample through the filtration system comprises driving the feed sample through the filtration system under the influence of gravity, and the method further comprises creating laminar flow conditions in the flow chamber.

27. The method of claim 24, wherein driving the feed sample through the filtration system comprises concurrently driving the feed sample through a plurality of high module density devices, each of the plurality of the high module density devices including a plurality of the at least one filtration units.

28. The method of claim 24, further comprising creating gentle flow conditions in the flow chamber which provide for about 99% of the target cell population collected in the first collection chamber to be viable.

29. The method of claim 24, wherein collecting the target cell population in the first collection chamber comprises:
directing the at least 75% of the target cell population to the first collection chamber; and
collecting the target cell population in the first collection chamber in a fluid volume of less than about 25% of the volume of the feed sample in the first collection chamber.

30. The method of claim 24, wherein the target cell population includes blood cells.

31. The method of claim 24, wherein the target cell population includes stem cells.

32. The method of claim 24, wherein the target cell population includes CD34+ cells.

33. The method of claim 24, wherein the target cell population includes cells derived from an adipose tissue.

34. The method of claim 24, wherein the target cell population includes umbilical cord blood cells.

35. A method for umbilical cord blood volume reduction, the method comprising:
introducing umbilical cord blood having an initial volume, a population of red blood cells and a viable population of a first type of nucleated cells into the filtration system of claim 17 within about six hours from draw
passing the umbilical cord blood through the filtration system;
collecting at least a portion of the population of red blood cells in the second collection chamber, and
collecting at least 75% of the first type of nucleated cells in a fluid volume of less than about 25% of the initial volume in the first collection chamber, greater than about 99% of the population of nucleated cells collected in the first collection chamber being viable.

36. The method of claim 35, further comprising drawing umbilical cord blood into a first receptacle, wherein introducing the umbilical cord blood into the filtration system comprises forming a closed system by connecting the first receptacle to the filtration system.

37. The method of claim 36, wherein the first receptacle contains a fluid.

38. The method of claim 36, wherein the first receptacle contains an additive.

39. The method of claim 36, wherein the first receptacle contains an anticoagulant.

40. The method of claim 35, wherein passing the umbilical cord blood through the filtration system comprises passing the umbilical cord blood through the filtration system under the influence of gravity.

41. The method of claim 35, wherein the first type of nucleated cells are CD34+ cells.

42. The method of claim 35, wherein the first type of nucleated cells is stem cells.

43. The method of claim 35, wherein the first collection chamber is a cryopreservation freezing bag.

44. The method of claim 35, wherein the fluid flow inside the flow chamber is laminar.

* * * * *